United States Patent
Deligny et al.

(10) Patent No.: US 10,669,286 B2
(45) Date of Patent: Jun. 2, 2020

(54) FUSED PENTACYCLIC IMIDAZOLE DERIVATIVES AS MODULATORS OF TNF ACTIVITY

(71) Applicants: UCB Biopharma SRL, Brussels (BE); Sanofi, Paris (FR)

(72) Inventors: Michael Louis Robert Deligny, Brussels (BE); Jag Paul Heer, Slough Berkshire (GB)

(73) Assignees: UCB Biopharma SRL, Brussels (BE); Sanofi, Paris (FR)

( * ) Notice: Subject to any disclaimer, the term of this patent is extended or adjusted under 35 U.S.C. 154(b) by 0 days.

(21) Appl. No.: 16/086,418

(22) PCT Filed: Mar. 31, 2017

(86) PCT No.: PCT/EP2017/057765
§ 371 (c)(1),
(2) Date: Sep. 19, 2018

(87) PCT Pub. No.: WO2017/167993
PCT Pub. Date: Oct. 5, 2017

(65) Prior Publication Data
US 2019/0119302 A1    Apr. 25, 2019

(30) Foreign Application Priority Data
Apr. 1, 2016 (EP) .................... 16163571

(51) Int. Cl.
| | | |
|---|---|---|
| C07D 487/04 | (2006.01) |
| C07D 519/00 | (2006.01) |
| C07D 487/18 | (2006.01) |
| C07D 487/22 | (2006.01) |
| A61P 25/28 | (2006.01) |
| A61P 37/04 | (2006.01) |
| A61P 9/00 | (2006.01) |
| A61P 3/10 | (2006.01) |
| A61P 35/00 | (2006.01) |

(52) U.S. Cl.
CPC ......... C07D 519/00 (2013.01); C07D 487/04 (2013.01); C07D 487/18 (2013.01); C07D 487/22 (2013.01); *A61P 3/10* (2018.01); *A61P 9/00* (2018.01); *A61P 25/28* (2018.01); *A61P 35/00* (2018.01); *A61P 37/04* (2018.01)

(58) Field of Classification Search
CPC .. C07D 487/04; C07D 487/18; A61K 31/428; A61K 31/4188

USPC .......... 540/520; 544/333; 546/43; 514/215, 514/256, 281
See application file for complete search history.

(56) References Cited

U.S. PATENT DOCUMENTS

2015/0152065 A1    6/2015    Brookings et al.

FOREIGN PATENT DOCUMENTS

| | | |
|---|---|---|
| WO | WO 2004/087720 | 10/2004 |
| WO | WO 2009/156091 | 12/2009 |
| WO | WO 2012/177707 | 2/2012 |
| WO | WO 2012/135082 | 10/2012 |
| WO | WO 2013/186229 | 12/2013 |
| WO | WO 2014/009295 | 1/2014 |
| WO | WO 2014/009296 | 1/2014 |
| WO | WO 2015/086525 | 6/2015 |
| WO | WO 2015/086526 | 6/2015 |
| WO | WO 2016/050975 | 4/2016 |

OTHER PUBLICATIONS

Tansey & Szymkowski, Drug Discovery Today, 2009, 14, 1082-1088.
Carneiro et al., J. Secual Medicine, 2010, 7, 3823-3834.
Wu et al., JAMA, 2013, 309, 2043-2044.
Hauwemeiren et al., J. Clin. Invest., 2013, 123, 2590-2603.
Eichman & Stambuli, 2009, J. Org. Chem., 2009, 74, 4005-4008.
Bahrami et al., J. Org. Chem., 2009, 74, 9287-9291.
Hilpert et al., Journal of medicinal Chemistry, 2013, 56(10), 3980-3995.
Armstrong et al., J. Org. Chem., 2013, 78, 10534.
Sakai et al., J. Org. Chem., 20 2007, 72, 5920-5922.
Okamura et al., Organic Letters, 2004, 6(8), 1305-1307.
Nagib & McMillan, Nature, 2011, 480, 224.
Bentley et al., Organic Process Research & Development, 2002, 6(2) 109-112.
Nam et al., Bio-org. Med. Chem., 2004, 12, 6255.
Lacko et al., Current Medicinal Chemistry, 2012, 19, 4699.

*Primary Examiner* — Deepak R Rao
(74) *Attorney, Agent, or Firm* — McDonnell Boehnen Hulbert & Berghoff LLP

(57) ABSTRACT

A series of substituted fused pentacyclic benzimidazole derivatives, and analogues thereof, being potent modulators of human TNFα activity, are accordingly of benefit in the treatment and/or prevention of various human ailments, including autoimmune and inflammatory disorders; neurological and neurodegenerative disorders; pain and nociceptive disorders; cardiovascular disorders; metabolic disorders; ocular disorders; and oncological disorders.

10 Claims, No Drawings

FUSED PENTACYCLIC IMIDAZOLE DERIVATIVES AS MODULATORS OF TNF ACTIVITY

This application is a US national stage application under 35 U.S.C. § 371 of International Application No. PCT/EP2017/057765, filed Mar. 31, 2017, which claims priority to European Application No. 16163571.9, filed Apr. 1, 2016.

The present invention relates to a class of fused pentacyclic imidazole derivatives, and to their use in therapy. More particularly, this invention is concerned with pharmacologically active substituted fused pentacyclic benzimidazole derivatives and analogues thereof. These compounds are modulators of the signalling of TNFα, and are accordingly of benefit as pharmaceutical agents, especially in the treatment of adverse inflammatory and autoimmune disorders, neurological and neurodegenerative disorders, pain and nociceptive disorders, cardiovascular disorders, metabolic disorders, ocular disorders, and oncological disorders.

TNFα is the prototypical member of the Tumour Necrosis Factor (TNF) superfamily of proteins that share a primary function of regulating cell survival and cell death. One structural feature common to all known members of the TNF superfamily is the formation of trimeric complexes that bind to, and activate, specific TNF superfamily receptors. By way of example, TNFα exists in soluble and transmembrane forms and signals through two receptors, known as TNFR1 and TNFR2, with distinct functional endpoints.

Various products capable of modulating TNFα activity are already commercially available. All are approved for the treatment of inflammatory and autoimmune disorders such as rheumatoid arthritis and Crohn's disease. All currently approved products are macromolecular and act by inhibiting the binding of human TNFα to its receptor. Typical macromolecular TNFα inhibitors include anti-TNFα antibodies; and soluble TNFα receptor fusion proteins. Examples of commercially available anti-TNFα antibodies include fully human antibodies such as adalimumab (Humira®) and golimumab (Simponi®), chimeric antibodies such as infliximab (Remicade®), and pegylated Fab' fragments such as certolizumab pegol (Cimzia®). An example of a commercially available soluble TNFα receptor fusion protein is etanercept (Enbrel®).

TNF superfamily members, including TNFα itself, are implicated in a variety of physiological and pathological functions that are believed to play a part in a range of conditions of significant medical importance (see, for example, M. G. Tansey & D. E. Szymkowski, *Drug Discovery Today*, 2009, 14, 1082-1088; and F. S. Carneiro et al., *J. Sexual Medicine*, 2010, 7, 3823-3834).

The compounds in accordance with the present invention, being potent modulators of human TNFα activity, are therefore beneficial in the treatment and/or prevention of various human ailments. These include autoimmune and inflammatory disorders; neurological and neurodegenerative disorders; pain and nociceptive disorders; cardiovascular disorders; metabolic disorders; ocular disorders; and oncological disorders.

In addition, the compounds in accordance with the present invention may be beneficial as pharmacological standards for use in the development of new biological tests and in the search for new pharmacological agents. Thus, in one embodiment, the compounds of this invention may be useful as radioligands in assays for detecting pharmacologically active compounds. In an alternative embodiment, certain compounds of this invention may be useful for coupling to a fluorophore to provide fluorescent conjugates that can be utilised in assays (e.g. a fluorescence polarisation assay) for detecting pharmacologically active compounds.

WO 2013/186229, WO 2014/009295 and WO 2014/009296 relate to fused bicyclic imidazole derivatives which are modulators of the signalling of TNFα.

WO 2015/086525 and WO 2015/086526 relate to fused tricyclic imidazole derivatives which are modulators of the signalling of TNFα.

Co-pending international patent application PCT/EP2015/072868, published on 7 Apr. 2016 as WO 2016/050975, relates to fused pentacyclic imidazole derivatives which are modulators of the signalling of TNFα.

None of the prior art available to date, however, discloses or suggests the precise structural class of fused pentacyclic imidazole derivatives as provided by the present invention.

The present invention provides a compound of formula (I) or an N-oxide thereof, or a pharmaceutically acceptable salt thereof:

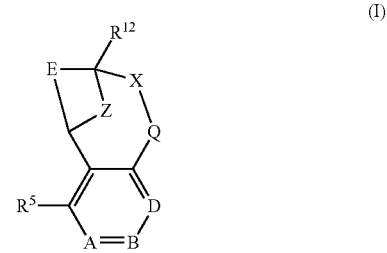

(I)

wherein

A represents N or C—R$^6$;

B represents N or C—R$^7$; and

D represents N or C—R$^8$, provided that at least one of A, B and D represents N;

—X-Q- represents —O—, —O—C(O)—, —C(O)—O—, —O—C(=CH—CN)—, —S—, —SO—, —SO$_2$—, —N(R$^g$)—, —N(R$^f$)—CO—, —CO—N(R$^f$)—, —N(R$^f$)—SO$_2$—, —SO$_2$—N(R$^F$)—, —S(O)(NR$^f$)—, —N(R$^F$)—C(S)—, —N=S(O)(CH$_3$)—, —O—C(=CH$_2$)— or —S(=N—CN)—; or —X-Q- represents —CH$_2$—CH$_2$—, —O—CH$_2$—, —CH$_2$—O—, —S—CH$_2$—, —SO—CH$_2$—, —SO$_2$—CH$_2$—, —CH$_2$—S—, —CH$_2$—SO—, —CH$_2$—SO$_2$—, —N(R$^g$)—CH$_2$—, —CH$_2$—N(R$^g$)—, —S(O)(NR$^f$)—CH$_2$— or —CH$_2$—S(O)(NR$^f$)—, any of which groups may be optionally substituted by one or more substituents;

Z represents methylene;

E represents a fused heteroaromatic ring system selected from the groups of formula (Ea), (Eb) and (Ec):

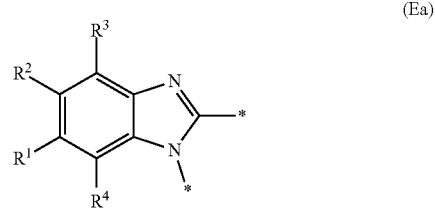

(Ea)

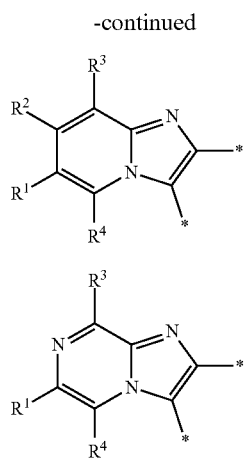

wherein the asterisks (*) represent the site of attachment of E to the remainder of the molecule;

$R^1$ represents hydrogen, halogen, cyano, trifluoromethyl, trifluoromethoxy, $-OR^a$, $-SR^a$, $-SOR^a$, $-SO_2R^a$, $-NR^bR^c$, $-NR^cCOR^d$, $-NR^cCO_2R^d$, $-NHCONR^bR^c$, $-NR^cSO_2R^e$, $-COR^d$, $-CO_2R^d$, $-CONR^bR^c$, $-SO_2NR^bR^c$, or $-S(O)(N-R^b)R^e$; or $R^1$ represents $C_{1-6}$ alkyl, $C_{3-7}$ cycloalkyl, $C_{4-7}$ cycloalkenyl, aryl, aryl($C_{1-6}$) alkyl, $C_{3-7}$ heterocycloalkyl, $C_{3-7}$ heterocycloalkenyl, heteroaryl, heteroaryl($C_{1-6}$)alkyl, ($C_{3-7}$)heterocycloalkyl($C_{1-6}$) alkyl-aryl-, ($C_{3-7}$)heterocycloalkenyl-aryl-, ($C_{3-7}$)cycloalkyl-heteroaryl-, ($C_{3-7}$)cycloalkyl-($C_{1-6}$)alkyl-heteroaryl-, ($C_{4-7}$)cycloalkenyl-heteroaryl-, ($C_{4-9}$)bicycloalkyl-heteroaryl-, ($C_{3-7}$)heterocycloalkyl-heteroaryl-, ($C_{3-7}$)heterocycloalkyl($C_{1-6}$)alkyl-heteroaryl-, ($C_{3-7}$)heterocycloalkenyl-heteroaryl-, ($C_{4-9}$)heterobicycloalkyl-heteroaryl- or ($C_{4-9}$)spiroheterocycloalkyl-heteroaryl-, any of which groups may be optionally substituted by one or more substituents;

$R^2$ represents hydrogen, halogen, cyano, nitro, hydroxy, trifluoromethyl, trifluoromethoxy or $-OR^a$; or $R^2$ represents $C_{1-6}$ alkyl or heteroaryl, either of which groups may be optionally substituted by one or more substituents;

$R^3$ and $R^4$ independently represent hydrogen, halogen or trifluoromethyl; or $C_{1-6}$ alkyl, which group may be optionally substituted by one or more substituents;

$R^5$ represents hydrogen, halogen, hydroxy, cyano, trifluoromethyl, difluoro-methoxy, trifluoromethoxy, $-OR^a$ or $C_{1-6}$ alkylsulphonyl; or $R^5$ represents $C_{1-6}$ alkyl, which group may be optionally substituted by one or more substituents;

$R^6$, $R^7$ and $R^8$ independently represent hydrogen, halogen, trifluoromethyl, $C_{1-6}$ alkyl or $C_{1-6}$ alkoxy;

$R^{12}$ represents hydrogen or $C_{1-6}$ alkyl;

$R^a$ represents $C_{1-6}$ alkyl, $C_{3-7}$ cycloalkyl, aryl, aryl($C_{1-6}$) alkyl, $C_{3-7}$ hetero-cycloalkyl, heteroaryl or heteroaryl($C_{1-6}$) alkyl, any of which groups may be optionally substituted by one or more substituents;

$R^b$ and $R^c$ independently represent hydrogen or trifluoromethyl; or $C_{1-6}$ alkyl, $C_{3-7}$ cycloalkyl, $C_{3-7}$ cycloalkyl ($C_{1-6}$)alkyl, aryl, aryl($C_{1-6}$)alkyl, $C_{3-7}$ heterocycloalkyl, $C_{3-7}$ heterocycloalkyl($C_{1-6}$)alkyl, heteroaryl or heteroaryl($C_{1-6}$) alkyl, any of which groups may be optionally substituted by one or more substituents; or $R^b$ and $R^c$, when taken together with the nitrogen atom to which they are both attached, represent a heterocyclic moiety selected from azetidin-1-yl, pyrrolidin-1-yl, oxazolidin-3-yl, isoxazolidin-2-yl, thiazolidin-3-yl, isothiazolidin-2-yl, piperidin-1-yl, morpholin-4-yl, thiomorpholin-4-yl, piperazin-1-yl, homopiperidin-1-yl, homomorpholin-4-yl, homopiperazin-1-yl, (imino)(oxo)thiazinan-4-yl, (oxo)thiazinan-4-yl and (dioxo)-thiazinan-4-yl, any of which groups may be optionally substituted by one or more substituents;

$R^d$ represents hydrogen; or $R^d$ represents $C_{1-6}$ alkyl, $C_{3-7}$ cycloalkyl, aryl, $C_{3-7}$ heterocycloalkyl or heteroaryl, any of which groups may be optionally substituted by one or more substituents;

$R^e$ represents $C_{1-6}$ alkyl, aryl or heteroaryl, any of which groups may be optionally substituted by one or more substituents;

$R^f$ represents hydrogen; or $R^f$ represents $C_{1-6}$ alkyl, $C_{3-7}$ cycloalkyl or $C_{3-7}$ heterocycloalkyl, any of which groups may be optionally substituted by one or more substituents; and $R^g$ represents hydrogen, $-SO_2R^a$, $-COR^d$ or $-CO_2R^d$; or $R^g$ represents $C_{1-6}$ alkyl, $C_{3-7}$ cycloalkyl, $C_{3-7}$ heterocycloalkyl or heteroaryl, any of which groups may be optionally substituted by one or more substituents.

The present invention also provides a compound of formula (I) as defined above or an N-oxide thereof, or a pharmaceutically acceptable salt thereof, for use in therapy.

The present invention also provides a compound of formula (I) as defined above or an N-oxide thereof, or a pharmaceutically acceptable salt thereof, for use in the treatment and/or prevention of disorders for which the administration of a modulator of TNFα function is indicated.

In another aspect, the present invention provides a compound of formula (I) as defined above or an N-oxide thereof, or a pharmaceutically acceptable salt thereof, for use in the treatment and/or prevention of an inflammatory or autoimmune disorder, a neurological or neurodegenerative disorder, pain or a nociceptive disorder, a cardiovascular disorder, a metabolic disorder, an ocular disorder, or an oncological disorder.

The present invention also provides the use of a compound of formula (I) as defined above or an N-oxide thereof, or a pharmaceutically acceptable salt thereof, for the manufacture of a medicament for the treatment and/or prevention of disorders for which the administration of a modulator of TNFα function is indicated.

In another aspect, the present invention provides the use of a compound of formula (I) as defined above or an N-oxide thereof, or a pharmaceutically acceptable salt thereof, for the manufacture of a medicament for the treatment and/or prevention of an inflammatory or autoimmune disorder, a neurological or neurodegenerative disorder, pain or a nociceptive disorder, a cardiovascular disorder, a metabolic disorder, an ocular disorder, or an oncological disorder.

The present invention also provides a method for the treatment and/or prevention of disorders for which the administration of a modulator of TNFα function is indicated which comprises administering to a patient in need of such treatment an effective amount of a compound of formula (I) as defined above or an N-oxide thereof, or a pharmaceutically acceptable salt thereof.

In another aspect, the present invention provides a method for the treatment and/or prevention of an inflammatory or autoimmune disorder, a neurological or neuro-degenerative disorder, pain or a nociceptive disorder, a cardiovascular disorder, a metabolic disorder, an ocular disorder, or an oncological disorder, which comprises administering to a patient in need of such treatment an effective amount of a compound of formula (I) as defined above or an N-oxide thereof, or a pharmaceutically acceptable salt thereof.

Where any of the groups in the compounds of formula (I) above is stated to be optionally substituted, this group may be unsubstituted, or substituted by one or more substituents. Typically, such groups will be unsubstituted, or substituted by one or two substituents.

The present invention includes within its scope salts of the compounds of formula (I) above. For use in medicine, the salts of the compounds of formula (I) will be pharmaceutically acceptable salts. Other salts may, however, be useful in the preparation of the compounds of use in the invention or of their pharmaceutically acceptable salts.

Standard principles underlying the selection and preparation of pharmaceutically acceptable salts are described, for example, in *Handbook of Pharmaceutical Salts: Properties, Selection and Use*, ed. P. H. Stahl & C. G. Wermuth, Wiley-VCH, 2002.

The present invention includes within its scope solvates of the compounds of formula (I) above. Such solvates may be formed with common organic solvents or water.

The present invention also includes within its scope co-crystals of the compounds of formula (I) above. The technical term "co-crystal" is used to describe the situation where neutral molecular components are present within a crystalline compound in a definite stoichiometric ratio. The preparation of pharmaceutical co-crystals enables modifications to be made to the crystalline form of an active pharmaceutical ingredient, which in turn can alter its physicochemical properties without compromising its intended biological activity (see *Pharmaceutical Salts and Co-crystals*, ed. J. Wouters & L. Quere, RSC Publishing, 2012).

Suitable alkyl groups which may be present on the compounds in accordance with the invention include straight-chained and branched $C_{1-6}$ alkyl groups, for example $C_{1-4}$ alkyl groups. Typical examples include methyl and ethyl groups, and straight-chained or branched propyl, butyl and pentyl groups. Suitable alkyl groups include methyl, ethyl, n-propyl, isopropyl, n-butyl, sec-butyl, isobutyl, tert-butyl, 2,2-dimethylpropyl and 3-methylbutyl. Derived expressions such as "$C_{1-6}$ alkoxy", "$C_{1-6}$ alkylthio", "$C_{1-6}$ alkylsulphonyl" and "$C_{1-6}$ alkylamino" are to be construed accordingly.

The term "$C_{3-7}$ cycloalkyl" as used herein refers to monovalent groups of 3 to 7 carbon atoms derived from a saturated monocyclic hydrocarbon, and may comprise benzo-fused analogues thereof. Suitable $C_{3-7}$ cycloalkyl groups include cyclopropyl, cyclobutyl, benzocyclobutenyl, cyclopentyl, indanyl, cyclohexyl and cycloheptyl.

The term "$C_{4-7}$ cycloalkenyl" as used herein refers to monovalent groups of 4 to 7 carbon atoms derived from a partially unsaturated monocyclic hydrocarbon. Suitable $C_{4-7}$ cycloalkenyl groups include cyclobutenyl, cyclopentenyl, cyclohexenyl and cycloheptenyl.

The term "$C_{4-9}$ bicycloalkyl" as used herein refers to monovalent groups of 4 to 9 carbon atoms derived from a saturated bicyclic hydrocarbon. Typical bicycloalkyl groups include bicyclo[3.1.0]hexanyl, bicyclo[4.1.0]heptanyl and bicyclo[2.2.2]octanyl.

The term "aryl" as used herein refers to monovalent carbocyclic aromatic groups derived from a single aromatic ring or multiple condensed aromatic rings. Suitable aryl groups include phenyl and naphthyl, preferably phenyl.

Suitable aryl($C_{1-6}$)alkyl groups include benzyl, phenylethyl, phenylpropyl and naphthylmethyl.

The term "$C_{3-7}$ heterocycloalkyl" as used herein refers to saturated monocyclic rings containing 3 to 7 carbon atoms and at least one heteroatom selected from oxygen, sulphur and nitrogen, and may comprise benzo-fused analogues thereof. Suitable heterocycloalkyl groups include oxetanyl, azetidinyl, tetrahydrofuranyl, dihydrobenzo-furanyl, dihydrobenzothienyl, pyrrolidinyl, indolinyl, isoindolinyl, oxazolidinyl, thiazolidinyl, isothiazolidinyl, imidazolidinyl, tetrahydropyranyl, chromanyl, dioxanyl, tetrahydrothiopyranyl, piperidinyl, 1,2,3,4-tetrahydroquinolinyl, 1,2,3,4-tetrahydro-isoquinolinyl, piperazinyl, 1,2,3,4-tetrahydroquinoxalinyl, hexahydro-[1,2,5]thiadiazolo-[2,3-a]pyrazinyl, homopiperazinyl, morpholinyl, benzoxazinyl, thiomorpholinyl, azepanyl, oxazepanyl, diazepanyl, thiadiazepanyl and azocanyl.

The term "$C_{3-7}$ heterocycloalkenyl" as used herein refers to monounsaturated or polyunsaturated monocyclic rings containing 3 to 7 carbon atoms and at least one heteroatom selected from oxygen, sulphur and nitrogen, and may comprise benzo-fused analogues thereof. Suitable heterocycloalkenyl groups include thiazolinyl, imidazolinyl, dihydropyranyl, dihydrothiopyranyl and 1,2,3,6-tetrahydropyridinyl.

The term "$C_{4-9}$ heterobicycloalkyl" as used herein corresponds to $C_{4-9}$ bicycloalkyl wherein one or more of the carbon atoms have been replaced by one or more heteroatoms selected from oxygen, sulphur and nitrogen. Typical heterobicycloalkyl groups include 3-azabicyclo[3.1.0]hexanyl, 2-oxa-5-azabicyclo[2.2.1]heptanyl, 6-azabicyclo[3.2.0]heptanyl, 3-azabicyclo[3.1.1]heptanyl, 3-azabicyclo[4.1.0]heptanyl, 2-oxabicyclo[2.2.2]octanyl, quinuclidinyl, 2-oxa-5-azabicyclo[2.2.2]octanyl, 3-azabicyclo[3.2.1]octanyl, 8-azabicyclo-[3.2.1]octanyl, 3-oxa-8-azabicyclo[3.2.1]octanyl, 3,8-diazabicyclo[3.2.1]octanyl, 3,6-diazabicyclo[3.2.2]nonanyl, 3-oxa-7-azabicyclo[3.3.1]nonanyl, 3,7-dioxa-9-azabicyclo-[3.3.1]nonanyl and 3,9-diazabicyclo[4.2.1]nonanyl.

The term "$C_{4-9}$ spiroheterocycloalkyl" as used herein refers to saturated bicyclic ring systems containing 4 to 9 carbon atoms and at least one heteroatom selected from oxygen, sulphur and nitrogen, in which the two rings are linked by a common atom.

Suitable spiroheterocycloalkyl groups include 5-azaspiro[2.3]hexanyl, 5-azaspiro[2.4]-heptanyl, 2-azaspiro[3.3]heptanyl, 2-oxa-6-azaspiro[3.3]heptanyl, 2-oxa-6-azaspiro[3.4]-octanyl, 2-oxa-6-azaspiro[3.5]nonanyl, 7-oxa-2-azaspiro[3.5]nonanyl, 2-oxa-7-azaspiro-[3.5]nonanyl and 2,4,8-triazaspiro[4.5]decanyl.

The term "heteroaryl" as used herein refers to monovalent aromatic groups containing at least 5 atoms derived from a single ring or multiple condensed rings, wherein one or more carbon atoms have been replaced by one or more heteroatoms selected from oxygen, sulphur and nitrogen. Suitable heteroaryl groups include furyl, benzofuryl, dibenzo furyl, thienyl, benzothienyl, thieno[2,3-c]pyrazolyl, thieno[3,4-b][1,4]dioxinyl, dibenzothienyl, pyrrolyl, indolyl, pyrrolo[2,3-b]pyridinyl, pyrrolo[3,2-c]pyridinyl, pyrrolo[3,4-b]pyridinyl, pyrazolyl, pyrazolo[1,5-a]pyridinyl, pyrazolo[3,4-d]pyrimidinyl, indazolyl, 4,5,6,7-tetrahydroindazolyl, oxazolyl, benzoxazolyl, isoxazolyl, thiazolyl, benzothiazolyl, isothiazolyl, imidazolyl, benzimidazolyl, imidazo[2,1-b]thiazolyl, imidazo[1,2-a]pyridinyl, imidazo[4,5-b]pyridinyl, purinyl, imidazo[1,2-a]pyrimidinyl, imidazo[1,2-a]pyrazinyl, oxadiazolyl, thiadiazolyl, triazolyl, [1,2,4]triazolo[1,5-a]-pyrimidinyl, benzotriazolyl, tetrazolyl, pyridinyl, quinolinyl, isoquinolinyl, naphthyridinyl, pyridazinyl, cinnolinyl, phthalazinyl, pyrimidinyl, quinazolinyl, pyrazinyl, quinoxalinyl, pteridinyl, triazinyl and chromenyl groups.

The term "halogen" as used herein is intended to include fluorine, chlorine, bromine and iodine atoms, typically fluorine, chlorine or bromine.

Where the compounds of formula (I) have one or more asymmetric centres, they may accordingly exist as enantiomers. Where the compounds in accordance with the invention possess two or more asymmetric centres, they may additionally exist as diastereomers. The invention is to be understood to extend to the use of all such enantiomers and diastereomers, and to mixtures thereof in any proportion, including racemates. Formula (I) and the formulae depicted hereinafter are intended to represent all individual stereoisomers and all possible mixtures thereof, unless stated or shown otherwise. In addition, compounds of formula (I) may exist as tautomers, for example keto ($CH_2C$=O)↔enol (CH=CHOH) tautomers or amide (NHC=O)↔hydroxyimine (N=COH) tautomers. Formula (I) and the formulae depicted hereinafter are intended to represent all individual tautomers and all possible mixtures thereof, unless stated or shown otherwise.

As will be appreciated, 2-oxo-(1H)-pyridinyl is a tautomer of 2-hydroxypyridinyl; and 2-oxo-(1H)-pyrimidinyl is a tautomer of 2-hydroxypyrimidinyl.

It is to be understood that each individual atom present in formula (I), or in the formulae depicted hereinafter, may in fact be present in the form of any of its naturally occurring isotopes, with the most abundant isotope(s) being preferred. Thus, by way of example, each individual hydrogen atom present in formula (I), or in the formulae depicted hereinafter, may be present as a $^1H$, $^2H$ (deuterium) or $^3H$ (tritium) atom, preferably $^1H$. Similarly, by way of example, each individual carbon atom present in formula (I), or in the formulae depicted hereinafter, may be present as a $^{12}C$, $^{13}C$ or $^{14}C$ atom, preferably $^{12}C$.

A particular sub-class of compounds in accordance with the present invention is represented by formula (IA) or an N-oxide thereof, or a pharmaceutically acceptable salt thereof:

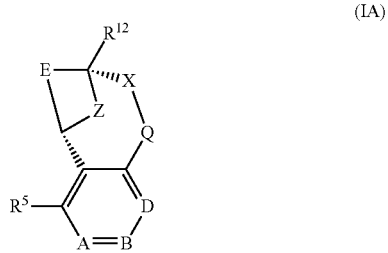

(IA)

wherein A, B, D, —X-Q-, Z, E, $R^5$ and $R^{12}$ are as defined above.

In a first embodiment, A represents N. In a second embodiment, A represents C—$R^6$.

In a first embodiment, B represents N. In a second embodiment, B represents C—$R^7$.

In a first embodiment, D represents N. In a second embodiment, D represents C—$R^8$.

Generally, at least one of A, B and D represents N. Suitably, one or two of A, B and D represents N. In one embodiment, one of A, B and D represents N. In another embodiment, two of A, B and D represent N.

In a first embodiment, A, B and D all represent N. In a second embodiment, A and B both represent N, and D represents C—$R^8$. In a third embodiment, A and D both represent N, and B represents C—$R^7$. In a fourth embodiment, A represents N, B represents C—$R^7$, and D represents C—$R^8$. In a fifth embodiment, A represents C—$R^6$, and B and D both represent N. In a sixth embodiment, A represents C—$R^6$, B represents N, and D represents C—$R^8$. In a seventh embodiment, A represents C—$R^6$, B represents C—$R^7$, and D represents N.

In a first embodiment, —X-Q- represents —O—. In a second embodiment, —X-Q-represents —O—C(O)—. In a third embodiment, —X-Q- represents —C(O)—O—. In a fourth embodiment, —X-Q- represents —O—C(=CH—CN)—. In a fifth embodiment, —X-Q- represents —S—. In a sixth embodiment, —X-Q- represents —SO—. In a seventh embodiment, —X-Q-represents —$SO_2$—. In an eighth embodiment, —X-Q- represents —N($R^g$)—. In a ninth embodiment, —X-Q- represents —N($R^f$)—CO—. In a tenth embodiment, —X-Q- represents —CO—N($R^f$)—. In an eleventh embodiment, —X-Q- represents —N($R^f$)—$SO_2$—. In a twelfth embodiment, —X-Q- represents —$SO_2$—N($R^f$)—. In a thirteenth embodiment, —X-Q-represents —S(O)(N$R^f$)—. In a fourteenth embodiment, —X-Q- represents optionally substituted —$CH_2$—$CH_2$—. In one aspect of that embodiment, —X-Q- represents —$CH_2$—$CH_2$—. In a fifteenth embodiment, —X-Q- represents optionally substituted —O—$CH_2$—. In one aspect of that embodiment, —X-Q- represents —O—$CH_2$—. In a sixteenth embodiment, —X-Q-represents optionally substituted —$CH_2$—O—. In one aspect of that embodiment, —X-Q-represents —$CH_2$—O—. In a seventeenth embodiment, —X-Q- represents optionally substituted —S—$CH_2$—. In one aspect of that embodiment, —X-Q- represents —S—$CH_2$—. In an eighteenth embodiment, —X-Q- represents optionally substituted —SO—$CH_2$—. In one aspect of that embodiment, —X-Q- represents —SO—$CH_2$—. In a nineteenth embodiment, —X-Q-represents optionally substituted —$SO_2$—$CH_2$—. In one aspect of that embodiment, —X-Q-represents —$SO_2$—$CH_2$—. In a twentieth embodiment, —X-Q- represents optionally substituted —$CH_2$—S—. In one aspect of that embodiment, X-Q- represents —$CH_2$—S—. In a twenty-first embodiment, —X-Q- represents optionally substituted —$CH_2$—SO—. In one aspect of that embodiment, —X-Q- represents —$CH_2$—SO—. In a twenty-second embodiment, —X-Q- represents optionally substituted —$CH_2$—$SO_2$—. In one aspect of that embodiment, —X-Q-represents —$CH_2$—$SO_2$—. In a twenty-third embodiment, —X-Q- represents optionally substituted —N($R^g$)—$CH_2$-. In one aspect of that embodiment, —X-Q- represents —N($R^g$)—$CH_2$-. In a twenty-fourth embodiment, —X-Q-represents optionally substituted —$CH_2$—N($R^g$)—. In one aspect of that embodiment, —X-Q- represents —$CH_2$—N($R^g$)—. In a twenty-fifth embodiment, —X-Q- represents optionally substituted —S(O)(N$R^f$)—$CH_2$—. In one aspect of that embodiment, —X-Q- represents —S(O)(N$R^f$)—$CH_2$—. In a twenty-sixth embodiment, —X-Q- represents optionally substituted —$CH_2$—S(O)(N$R^f$)—. In one aspect of that embodiment, —X-Q- represents —$CH_2$—S(O)(N$R^f$)—. In a twenty-seventh embodiment, —X-Q- represents —N($R^f$)—C(S)—. In a twenty-eighth embodiment, —X-Q- represents —N=S(O)($CH_3$)—. In a twenty-ninth embodiment, —X-Q- represents —O—C(=$CH_2$)—. In a thirtieth embodiment —X-Q- represents —S(=N—CN)—.

Typical examples of optional substituents on —X-Q- include halogen, $C_{1-6}$ alkyl, hydroxy($C_{1-6}$)alkyl, trifluoromethyl, $C_{2-6}$ alkylcarbonyl, carboxy and $C_{2-6}$ alkoxycarbonyl.

Typical examples of particular substituents on —X-Q- include fluoro, methyl, deuterated methyl, hydroxymethyl, hydroxyisopropyl, trifluoromethyl, acetyl, carboxy and ethoxycarbonyl.

Typically, —X-Q- represents —O—, —O—C(O)—, —O—C(=CH—CN)—, —S—, —SO—, —SO$_2$—, —N(R$^g$)—, —N(R$^f$)—CO—, —N(R$^f$)—SO$_2$—, —N(R$^f$)—C(S)—, —N=S(O)(CH$_3$)—, —O—C(=CH$_2$)— or —S(=N—CN)—; or —X-Q- represents —O—CH$_2$—, —CH$_2$—S—, —CH$_2$—SO—, —CH$_2$—SO$_2$— or —N(R$^g$)—CH$_2$-, any of which groups may be optionally substituted.

Suitably, —X-Q- represents —N(R$^g$)— or —N(R$^f$)—CO—.

Generally, E represents a fused heteroaromatic ring system of formula (Ea) or (Eb).

In a first embodiment, E represents a fused heteroaromatic ring system of formula (Ea).

In a second embodiment, E represents a fused heteroaromatic ring system of formula (Eb).

In a third embodiment, E represents a fused heteroaromatic ring system of formula (Ec).

Particular sub-classes of compounds in accordance with the present invention include the compounds of formula (IB), (IC) and (ID) and N-oxides thereof, and pharmaceutically acceptable salts thereof:

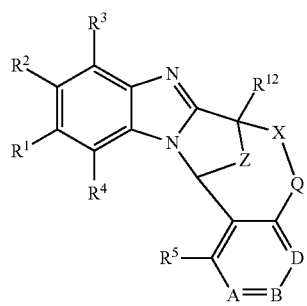

(IB)

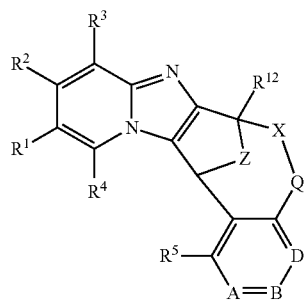

(IC)

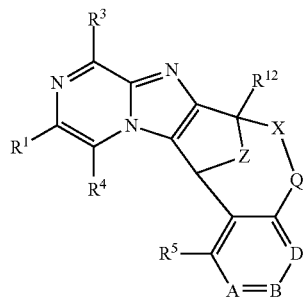

(ID)

wherein A, B, D, —X-Q-, Z, R$^1$, R$^2$, R$^3$, R$^4$, R$^5$ and R$^{12}$ are as defined above.

Particular sub-classes of compounds in accordance with the present invention include the compounds of formula (IB) and (IC) as defined above.

A particular sub-class of compounds in accordance with the present invention is represented by formula (IB) as defined above.

Generally, R$^1$ represents hydrogen, halogen or cyano; or R$^1$ represents aryl, C$_{3-7}$ heterocycloalkyl, C$_{3-7}$ heterocycloalkenyl, heteroaryl, heteroaryl-aryl-, (C$_{3-7}$)cycloalkyl-heteroaryl-, (C$_{4-9}$)bicycloalkyl-heteroaryl-, (C$_{3-7}$)heterocycloalkyl-heteroaryl-, (C$_{4-9}$)-heterobicycloalkyl-heteroaryl- or (C$_{4-9}$)spiroheterocycloalkyl-heteroaryl-, any of which groups may be optionally substituted by one or more substituents.

Typically, R$^1$ represents halogen; or R$^1$ represents C$_{3-7}$ heterocycloalkyl, heteroaryl, (C$_{3-7}$)cycloalkyl-heteroaryl-, (C$_{3-7}$)heterocycloalkyl-heteroaryl- or (C$_{4-9}$)-heterobicycloalkyl-heteroaryl-, any of which groups may be optionally substituted by one or more substituents.

Suitably, R$^1$ represents halogen; or R$^1$ represents heteroaryl, which group may be optionally substituted by one or more substituents.

More suitably, R$^1$ represents heteroaryl, which group may be optionally substituted by one or more substituents.

In a first embodiment, R$^1$ represents hydrogen.

In a second embodiment, R$^1$ represents halogen. In one aspect of that embodiment, R$^1$ represents fluoro. In another aspect of that embodiment, R$^1$ represents chloro.

In a third embodiment, R$^1$ represents cyano.

In a fourth embodiment, R$^1$ represents optionally substituted aryl. In one aspect of that embodiment, R$^1$ represents optionally substituted phenyl.

In fifth embodiment, R$^1$ represents optionally substituted C$_{3-7}$ heterocycloalkyl. In one aspect of that embodiment, R$^1$ represents optionally substituted azetidinyl.

In a sixth embodiment, R$^1$ represents optionally substituted (C$_{3-7}$)hetero-cycloalkenyl. In a first aspect of that embodiment, R$^1$ represents optionally substituted 1,2-dihydropyridinyl. In a second aspect of that embodiment, R$^1$ represents optionally substituted 1,2-dihydropyrimidinyl.

In a seventh embodiment, R$^1$ represents optionally substituted heteroaryl. In one aspect of that embodiment, R$^1$ represents optionally substituted pyridinyl. In another aspect of that embodiment, R$^1$ represents optionally substituted pyrimidinyl.

In an eighth embodiment, R$^1$ represents optionally substituted heteroaryl-aryl-. In one aspect of that embodiment, R$^1$ represents optionally substituted imidazolylphenyl-.

In a ninth embodiment, R$^1$ represents optionally substituted (C$_{3-7}$)cycloalkyl-heteroaryl-. In a first aspect of that embodiment, R$^1$ represents optionally substituted cyclohexylpyrazolyl-. In a second aspect of that embodiment, R$^1$ represents optionally substituted cyclopropylpyridinyl-. In a third aspect of that embodiment, R$^1$ represents optionally substituted cyclobutylpyridinyl-. In a fourth aspect of that embodiment, R$^1$ represents optionally substituted cyclopentylpyridinyl-. In a fifth aspect of that embodiment, R$^1$ represents optionally substituted cyclohexylpyridinyl-. In a sixth aspect of that embodiment, R$^1$ represents optionally substituted cyclopropylpyrimidinyl-. In a seventh aspect of that embodiment, R$^1$ represents optionally substituted cyclobutyl-pyrimidinyl-. In an eighth aspect of that embodiment, R$^1$ represents optionally substituted cyclopentylpyrimidinyl-. In a ninth aspect of that embodiment, R$^1$ represents optionally substituted cyclohexylpyrimidinyl-. In a tenth aspect of that embodiment, R$^1$ represents optionally substituted cyclohexylpyrazinyl-.

In a tenth embodiment, R$^1$ represents optionally substituted (C$_{4-9}$)bicycloalkyl-heteroaryl-.

In an eleventh embodiment, $R^1$ represents optionally substituted ($C_3$-7)-heterocycloalkyl-heteroaryl-. In a first aspect of that embodiment, $R^1$ represents substituted azetidinylpyrazolyl-. In a second aspect of that embodiment, $R^1$ represents optionally substituted pyrrolidinylpyridinyl-. In a third aspect of that embodiment, $R^1$ represents optionally substituted tetrahydropyranylpyridinyl-. In a fourth aspect of that embodiment, $R^1$ represents optionally substituted piperidinylpyridinyl-. In a fifth aspect of that embodiment, $R^1$ represents optionally substituted piperazinylpyridinyl-. In a sixth aspect of that embodiment, $R^1$ represents optionally substituted morpholinylpyridinyl-. In a seventh aspect of that embodiment, $R^1$ represents optionally substituted thiomorpholinylpyridinyl-. In an eighth aspect of that embodiment, $R^1$ represents optionally substituted diazepanylpyridinyl-. In a ninth aspect of that embodiment, $R^1$ represents optionally substituted oxetanylpyrimidinyl-. In a tenth aspect of that embodiment, $R^1$ represents optionally substituted azetidinylpyrimidinyl-. In an eleventh aspect of that embodiment, $R^1$ represents optionally substituted tetrahydrofuranyl-pyrimidinyl-. In a twelfth aspect of that embodiment, $R^1$ represents substituted tetrahydrothienyl-pyrimidinyl-. In a thirteenth aspect of that embodiment, $R^1$ represents optionally substituted pyrrolidinylpyrimidinyl-. In a fourteenth aspect of that embodiment, $R^1$ represents optionally substituted tetrahydropyranylpyrimidinyl-. In a fifteenth aspect of that embodiment, $R^1$ represents optionally substituted dioxanyl-pyrimidinyl-. In a sixteenth aspect of that embodiment, $R^1$ represents optionally substituted piperidinylpyrimidinyl-. In a seventeenth aspect of that embodiment, $R^1$ represents optionally substituted piperazinylpyrimidinyl-. In an eighteenth aspect of that embodiment, $R^1$ represents optionally substituted morpholinylpyrimidinyl-. In a nineteenth aspect of that embodiment, $R^1$ represents optionally substituted thiomorpholinylpyrimidinyl-. In a twentieth aspect of that embodiment, $R^1$ represents optionally substituted azepanylpyrimidinyl-. In a twenty-first aspect of that embodiment, $R^1$ represents optionally substituted oxazepanylpyrimidinyl-. In a twenty-second aspect of that embodiment, $R^1$ represents optionally substituted diazepanylpyrimidinyl-. In a twenty-third aspect of that embodiment, $R^1$ represents optionally substituted thiadiazepanylpyrimidinyl-. In a twenty-fourth aspect of that embodiment, $R^1$ represents optionally substituted oxetanylpyrazinyl-. In a twenty-fifth aspect of that embodiment, $R^1$ represents optionally substituted piperidinylpyrazinyl-.

In a twelfth embodiment, $R^1$ represents optionally substituted ($C_{4-9}$)-heterobicycloalkyl-heteroaryl-. In a first aspect of that embodiment, $R^1$ represents optionally substituted (2-oxa-5-azabicyclo[2.2.1]heptanyl)pyrimidinyl-. In a second aspect of that embodiment, $R^1$ represents optionally substituted (3-oxa-8-azabicyclo-[3.2.1]octanyl)pyrimidinyl-. In a third aspect of that embodiment, $R^1$ represents optionally substituted (3,6-diazabicyclo[3.2.2]nonanyl)pyrimidinyl-. In a fourth aspect of that embodiment, $R^1$ represents optionally substituted (3,7-dioxa-9-azabicyclo[3.3.1]-nonanyl)pyrimidinyl-.

In a thirteenth embodiment, $R^1$ represents optionally substituted ($C_{4-9}$)spiro-heterocycloalkyl-heteroaryl-.

Appositely, $R^1$ represents fluoro, chloro or cyano; or $R^1$ represents phenyl, azetidinyl, dihydropyridinyl, dihydropyrimidinyl, pyrazolyl, pyridinyl, pyrimidinyl, imidazolylphenyl, cyclopropylpyridinyl, cyclobutylpyridinyl, cyclobutylpyrimidinyl, cyclohexylpyridinyl, azetidinylpyrazolyl, oxetanylpyridinyl, azetidinylpyridinyl, pyrrolidinylpyridinyl, piperazinylpyridinyl, oxetanylpyrimidinyl, azetidinylpyrimidinyl, tetrahydrofuranylpyrimidinyl, tetrahydrothienylpyrimidinyl, pyrrolidinylpyrimidinyl, tetrahydropyranylpyrimidinyl, dioxanylpyrimidinyl, piperazinylpyrimidinyl, morpholinyl-pyrimidinyl, thiomorpholinylpyrimidinyl, diazepanylpyrimidinyl, (2-oxa-5-azabicyclo-[2.2.1]heptanyl)pyrimidinyl, (3-oxa-8-azabicyclo[3.2.1]octanyl)pyrimidinyl, (3,6-diazabicyclo[3.2.2]nonanyl)pyrimidinyl or (3,7-dioxa-9-azabicyclo[3.3.1]nonanyl)-pyrimidinyl, any of which groups may be optionally substituted by one or more substituents.

More typically, $R^1$ represents fluoro or chloro; or $R^1$ represents pyrimidinyl, cyclobutylpyrimidinyl, cyclopentylpyrimidinyl, cyclohexylpyrimidinyl, oxetanyl-pyrimidinyl, tetrahydrofuranylpyrimidinyl, pyrrolidinylpyrimidinyl, tetrahydropyranyl-pyrimidinyl, dioxanylpyrimidinyl or morpholinylpyrimidinyl, any of which groups may be optionally substituted by one or more substituents.

Still more typically, $R^1$ represents fluoro; or $R^1$ represents pyrimidinyl, which group may be optionally substituted by one or more substituents.

Illustratively, $R^1$ represents pyrimidinyl, which group may be optionally substituted by one or more substituents.

Typical examples of optional substituents on $R^1$ include one, two or three substituents independently selected from halogen, halo($C_{1-6}$)alkyl, cyano, cyano($C_{1-6}$)alkyl, nitro ($C_{1-6}$)alkyl, $C_{1-6}$ alkyl, phosphate($C_{1-6}$)alkyl, ($C_{1-6}$)alkylphosphate($C_{1-6}$)alkyl, phosphate($C_{1-6}$)alkoxy($C_{1-6}$)alkyl, sulphate($C_{1-6}$)alkyl, difluoromethyl, trifluoromethyl, trifluoroethyl, $C_{2-6}$ alkenyl, hydroxy, hydroxy($C_{1-6}$)alkyl, $C_{1-6}$ alkoxy, ($C_{1-6}$)alkoxy($C_{1-6}$)-alkyl, trifluoroethoxy, carboxy ($C_{3-7}$)cycloalkyloxy, $C_{1-6}$ alkylthio, $C_{1-6}$ alkylsulphonyl, ($C_{1-6}$)alkylsulphonyl($C_{1-6}$)alkyl, oxo, amino, amino($C_{1-6}$) alkyl, $C_{1-6}$ alkylamino, di($C_{1-6}$)-alkylamino, di($C_{1-6}$)alkylamino($C_{1-6}$)alkyl, ($C_{1-6}$)alkoxy($C_{1-6}$)alkylamino, N—[($C_{1-6}$)alkyl]-N-[hydroxy($C_{1-6}$)alkyl]amino, ($C_{2-6}$)alkylcarbonylamino($C_{1-6}$)alkyl, ($C_{2-6}$)alkoxycarbonyl-amino ($C_{1-6}$)alkyl, $C_{1-6}$ alkylsulphinylamino, $C_{1-6}$ alkylsulphonylamino, N—[($C_{1-6}$)alkyl]-N—[($C_{1-6}$)alkylsulphonyl]amino, bis[($C_{1-6}$)alkylsulphonyl]amino, ($C_{1-6}$) alkylsulphonylamino-($C_{1-6}$)alkyl, N—[($C_{1-6}$)alkyl]-N-[carboxy($C_{1-6}$)alkyl]amino, carboxy($C_{3-7}$)cycloalkylamino, carboxy($C_{3-7}$)cycloalkyl($C_{1-6}$)alkylamino, imino, formyl, $C_{2-6}$ alkylcarbonyl, ($C_{2-6}$)alkyl-carbonyloxy($C_{1-6}$)alkyl, carboxy, carboxy($C_{1-6}$)alkyl, $C_{2-6}$ alkoxycarbonyl, $C_{2-6}$ alkoxycarbonyl($C_{1-6}$)alkyl, morpholinyl($C_{1-6}$)alkoxycarbonyl, $C_{2-6}$ alkoxycarbonylmethylidenyl, aminocarbonyl, aminosulphonyl, ($C_{1-6}$)alkylsulphoximinyl and [($C_{1-6}$)alkyl][N—($C_{1-6}$)-alkyl]sulphoximinyl.

Illustrative examples of optional substituents on $R^1$ include one, two or three substituents independently selected from halogen, cyano, $C_{1-6}$ alkyl, difluoromethyl, hydroxy ($C_{1-6}$)alkyl, oxo, amino and amino($C_{1-6}$)alkyl.

Particular examples of optional substituents on $R^1$ include one, two or three substituents independently selected from hydroxy($C_{1-6}$)alkyl and amino($C_{1-6}$)alkyl.

Typical examples of particular substituents on $R^1$ include one, two or three substituents independently selected from fluoro, chloro, fluoromethyl, fluoroisopropyl, cyano, cyanoethyl, cyanoisopropyl, nitromethyl, methyl, ethyl, isopropyl, isopropylmethyl, phosphate-isopropyl, ethylphosphate-isopropyl, phosphate-methoxyisopropyl, sulphate-isopropyl, difluoromethyl, trifluoromethyl, trifluoroethyl, ethenyl, hydroxy, hydroxymethyl, hydroxyisopropyl, hydroxyisobutyl, methoxy, isopropoxy, methoxy-isopropyl, trifluoroethoxy, carboxycyclobutyloxy, methylthio, methylsulphonyl, methyl-sulphonylmethyl, methylsulphonylethyl, oxo, amino, aminomethyl, aminoisopropyl, methylamino, dimethylamino, dimethylaminoisopropyl, methoxyethylamino, N-(hydroxyethyl)-N-(methyl)amino, acetylaminomethyl, acetylaminoisopropyl, methoxy-carbonylaminoisopropyl, (tert-butoxycarbonyl)aminoisopropyl, (tert-butyl)sulphinylamino, methylsulphonylamino, (tert-butyl)sulphonylamino, N-methyl-N-(methyl-sulphonyl)amino, bis(methylsulphonyl)amino, methylsulphonylaminoisopropyl, N-(carboxyethyl)-N-(methyl)amino, carboxycyclopentylamino, carboxycyclopropylmethyl-amino, imino, formyl, acetyl, (tert-butyl)carbonyl, acetoxyisopropyl, carboxy, carboxy-methyl, carboxyethyl, methoxycarbonyl, ethoxycarbonyl, n-butoxycarbonyl, tert-butoxy-carbonyl, methoxycarbonylmethyl, ethoxycarbonylmethyl, ethoxycarbonylethyl, morpholinylethoxycarbonyl, ethoxycarbonylmethylidenyl, aminocarbonyl, amino-sulphonyl, methylsulphoximinyl and (methyl)(N-methyl)sulphoximinyl.

Illustrative examples of particular substituents on $R^1$ include one, two or three substituents independently selected from fluoro, cyano, methyl, difluoromethyl, hydroxyisopropyl, oxo, amino and aminoisopropyl.

Suitable examples of particular substituents on $R^1$ include one, two or three substituents independently selected from hydroxyisopropyl and aminoisopropyl.

In a particular embodiment, $R^1$ is substituted by hydroxy($C_{1-6}$)alkyl. In one aspect of that embodiment, $R^1$ is substituted by hydroxyisopropyl, especially 2-hydroxyprop-2-yl.

Illustrative values of $R^1$ include fluoro, chloro, cyano, (methyl)(methylthio)phenyl, methylsulphonylphenyl, (methyl)(methylsulphonyl)phenyl, methylsulphoximinylphenyl, (hydroxyisopropyl)azetidinyl, methylpyrazolyl, hydroxyisopropylpyridinyl, (hydroxyisopropyl)(methyl)pyridinyl, methoxypyridinyl, oxopyridinyl, (methyl)(oxo)-pyridinyl, cyanoisopropylpyrimidinyl, phosphate-isopropylpyrimidinyl, sulphate-isopropylpyrimidinyl, hydroxyisopropylpyrimidinyl, (hydroxyisopropyl)(methyl)-pyrimidinyl, (dimethyl)(hydroxyisopropyl)pyrimidinyl, (difluoromethyl)-(hydroxyisopropyl)pyrimidinyl, (hydroxyisopropyl)(trifluoromethyl)pyrimidinyl, hydroxyisobutylpyrimidinyl, methoxyisopropylpyrimidinyl, oxopyrimidinyl, aminoisopropylpyrimidinyl, (dimethylamino)isopropylpyrimidinyl, acetylaminoisopropyl-pyrimidinyl, (methoxycarbonyl)aminoisopropylpyrimidinyl, (tert-butoxycarbonyl)amino-isopropylpyrimidinyl, (methylsulphonyl)aminoisopropylpyrimidinyl, methyl-sulphoximinylpyridinyl, (dimethyl)imidazolylphenyl, methylsulphonylcyclopropyl-pyridinyl, aminocyclobutylpyridinyl, (tert-butyl)sulphinylaminocyclobutylpyridinyl, (dihydroxy)(methyl)cyclobutylpyrimidinyl, amino cyclobutylpyrimidinyl, (amino)(cyano)-cyclobutylpyrimidinyl, (amino)(difluoromethyl)cyclobutylpyrimidinyl, aminocyclopentyl-pyrimidinyl, (difluoro)(hydroxy)cyclohexylpyrimidinyl, (dihydroxy)(methyl)cyclohexyl-pyrimidinyl, (amino)(difluoro)cyclohexylpyrimidinyl, (methylsulphonyl)azetidinyl-pyrazolyl, aminooxetanylpyridinyl, (tert-butyl)sulphinylaminooxetanylpyridinyl, (tert-butyl)sulphonylaminooxetanylpyridinyl, pyrrolidinylpyridinyl, (hydroxy)pyrrolidinyl-pyridinyl, (tert-butoxycarbonyl)(hydroxy)pyrrolidinylpyridinyl, piperazinylpyridinyl, (methylsulphonyl)piperazinylpyridinyl, (hydroxy)oxetanylpyrimidinyl, (amino)oxetanyl-pyrimidinyl, (difluoro)azetidinylpyrimidinyl, (cyano)(methyl)azetidinylpyrimidinyl, (hydroxy)(methyl)azetidinylpyrimidinyl, (hydroxy)(trifluoromethyl)azetidinylpyrimidinyl, [(hydroxy)(trifluoromethyl)azetidinyl](methyl)pyrimidinyl, (hydroxyisopropyl)-(tetrahydrofuranyl)pyrimidinyl, aminotetrahydrofuranylpyrimidinyl, (hydroxy)-tetrahydrothienylpyrimidinyl, (hydroxy)(oxo)tetrahydrothienylpyrimidinyl, (hydroxy)-(dioxo)tetrahydrothienylpyrimidinyl, pyrrolidinylpyrimidinyl, methylpyrrolidinyl-pyrimidinyl, tetrahydropyranylpyrimidinyl, aminotetrahydropyranylpyrimidinyl, (amino)(dimethyl)dioxanylpyrimidinyl, (hydroxyisopropyl)piperidinylpyrimidinyl, (aminoisopropyl)piperidinylpyrimidinyl, (oxo)piperazinylpyrimidinyl, morpholinyl-pyrimidinyl, methylmorpholinylpyrimidinyl, aminomorpholinylpyrimidinyl, thiomorpholinylpyrimidinyl, (oxo)thiomorpholinylpyrimidinyl, (dioxo)thiomorpholinyl-pyrimidinyl, (amino)(dioxo)thiomorpholinylpyrimidinyl, (oxo)diazepanylpyrimidinyl, hydroxyisopropyl-(3-azabicyclo[3.1.0]hexanyl)pyrimidinyl, (2-oxa-5-azabicyclo[2.2.1]-heptanyl)pyrimidinyl, (3-oxa-8-azabicyclo[3.2.1]octanyl)pyrimidinyl, (oxo)(3,6-diazabicyclo[3.2.2]nonanyl)pyrimidinyl and (3,7-dioxa-9-azabicyclo[3.3.1]nonanyl)-pyrimidinyl.

Typical values of $R^1$ include fluoro, chloro, hydroxyisopropylpyrimidinyl, aminoisopropylpyrimidinyl, aminocyclobutylpyrimidinyl, (amino)(cyano)cyclobutyl-pyrimidinyl, (amino)(difluoromethyl)cyclobutylpyrimidinyl, aminocyclopentyl-pyrimidinyl, (amino)(difluoro)cyclohexylpyrimidinyl, (amino)oxetanylpyrimidinyl, aminotetrahydrofuranylpyrimidinyl, pyrrolidinylpyrimidinyl, methylpyrrolidinyl-pyrimidinyl, aminotetrahydropyranylpyrimidinyl, (amino)(dimethyl)dioxanylpyrimidinyl, (hydroxyisopropyl)piperidinylpyrimidinyl, (aminoisopropyl)piperidinylpyrimidinyl, morpholinylpyrimidinyl, methylmorpholinylpyrimidinyl, aminomorpholinylpyrimidinyl, (dioxo)thiomorpholinylpyrimidinyl, (amino)(dioxo)thiomorpholinylpyrimidinyl and hydroxyisopropyl-(3-azabicyclo[3.1.0]hexanyl)pyrimidinyl.

Selected values of $R^1$ include fluoro and hydroxyisopropylpyrimidinyl.

In a particular embodiment, $R^1$ represents hydroxyisopropylpyrimidinyl, especially 2-(2-hydroxypropan-2-yl)pyrimidin-5-yl.

Generally, $R^2$ represents hydrogen, halogen, trifluoromethyl, trifluoromethoxy or —$OR^a$; or $R^2$ represents $C_{1-6}$ alkyl or heteroaryl, either of which groups may be optionally substituted by one or more substituents.

Typically, $R^2$ represents hydrogen or halogen; or $R^2$ represents heteroaryl, which group may be optionally substituted by one or more substituents.

Appositely, $R^2$ represents halogen; or $R^2$ represents heteroaryl, which group may be optionally substituted by one or more substituents.

Suitably, $R^2$ represents hydrogen or halogen.

In a first embodiment, $R^2$ represents hydrogen. In a second embodiment, $R^2$ represents halogen. In one aspect of that embodiment, $R^2$ represents fluoro. In another aspect of that embodiment, $R^2$ represents chloro. In a third embodiment, $R^2$ represents cyano. In a fourth embodiment, $R^2$ represents nitro. In a fifth embodiment, $R^2$ represents hydroxy. In a sixth embodiment, $R^2$ represents trifluoromethyl. In a seventh embodiment, $R^2$ represents trifluoromethoxy. In an eighth embodiment, $R^2$ represents —$OR^a$. In a ninth embodiment, $R^2$ represents optionally substituted $C_{1-6}$ alkyl. In a first aspect of that embodiment, $R^2$ represents methyl. In a second aspect of that embodiment, $R^2$ represents ethyl. In a tenth embodiment, $R^2$ represents optionally substituted heteroaryl. In a first aspect of that embodiment, $R^2$ represents optionally substituted pyrimidinyl.

Typical examples of optional substituents on $R^2$ include one, two or three substituents independently selected from hydroxy($C_{1-6}$)alkyl and $C_{2-6}$ alkoxycarbonyl.

Suitable examples of optional substituents on $R^2$ include one, two or three substituents independently selected from hydroxy($C_{1-6}$)alkyl.

Typical examples of particular substituents on $R^2$ include one, two or three substituents independently selected from hydroxyisopropyl and ethoxycarbonyl.

Suitable examples of particular substituents on $R^2$ include one, two or three substituents independently selected from hydroxyisopropyl.

Typical values of $R^2$ include hydrogen, fluoro, chloro, trifluoromethyl, trifluoromethoxy, —$OR^a$, methyl, ethoxycarbonylethyl and hydroxyisopropylpyrimidinyl.

Suitable values of $R^2$ include hydrogen, fluoro and hydroxyisopropylpyrimidinyl.

Particular values of $R^2$ include fluoro and hydroxyisopropylpyrimidinyl.

Illustrative values of $R^2$ include hydrogen and fluoro.

Typically, $R^3$ represents hydrogen, halogen or $C_{1-6}$ alkyl.

In a first embodiment, $R^3$ represents hydrogen. In a second embodiment, $R^3$ represents halogen. In one aspect of that embodiment, $R^3$ represents fluoro. In a third embodiment, $R^3$ represents optionally substituted $C_{1-6}$ alkyl. In one aspect of that embodiment, $R^3$ represents methyl. In another aspect of that embodiment, $R^3$ represents ethyl.

Typically, $R^4$ represents hydrogen, halogen or $C_{1-6}$ alkyl.

In a first embodiment, $R^4$ represents hydrogen. In a second embodiment, $R^4$ represents halogen. In one aspect of that embodiment, $R^4$ represents fluoro. In a third embodiment, $R^4$ represents optionally substituted $C_{1-6}$ alkyl. In one aspect of that embodiment, $R^4$ represents methyl. In another aspect of that embodiment, $R^4$ represents ethyl.

Generally, $R^5$ represents halogen, cyano, difluoromethoxy, trifluoromethoxy, —$OR^a$ or $C_{1-6}$ alkylsulphonyl; or $R^5$ represents $C_{1-6}$ alkyl, which group may be optionally substituted by one or more substituents.

Typically, $R^5$ represents difluoromethoxy or —$OR^a$.

In a first embodiment, $R^5$ represents hydrogen. In a second embodiment, $R^5$ represents halogen. In one aspect of that embodiment, $R^5$ represents fluoro. In another aspect of that embodiment, $R^5$ represents chloro. In a third embodiment, $R^5$ represents hydroxy. In a fourth embodiment, $R^5$ represents cyano. In a fifth embodiment, $R^5$ represents trifluoromethyl. In a sixth embodiment, $R^5$ represents difluoromethoxy. In a seventh embodiment, $R^5$ represents trifluoromethoxy. In an eighth embodiment, $R^5$ represents —$OR^a$. In one aspect of that embodiment, $R^5$ represents methoxy. In a ninth embodiment, $R^5$ represents $C_{1-6}$ alkylsulphonyl. In one aspect of that embodiment, $R^5$ represents methylsulphonyl. In a tenth embodiment, $R^5$ represents optionally substituted $C_{1-6}$ alkyl. In one aspect of that embodiment, $R^5$ represents methyl. In another aspect of that embodiment, $R^5$ represents ethyl.

Appositely, $R^5$ represents difluoromethoxy or methoxy.

Generally, $R^6$ represents hydrogen, halogen or trifluoromethyl.

In a first embodiment, $R^6$ represents hydrogen. In a second embodiment, $R^6$ represents halogen. In one aspect of that embodiment, $R^6$ represents fluoro. In another aspect of that embodiment, $R^6$ represents chloro. In a third embodiment, $R^6$ represents trifluoromethyl. In a fourth embodiment, $R^6$ represents $C_{1-6}$ alkyl. In one aspect of that embodiment, $R^6$ represents methyl. In another aspect of that embodiment, $R^6$ represents ethyl. In a fifth embodiment, $R^6$ represents $C_{1-6}$ alkoxy. In one aspect of that embodiment, $R^6$ represents methoxy.

Generally, $R^7$ represents hydrogen or trifluoromethyl.

In a first embodiment, $R^7$ represents hydrogen. In a second embodiment, $R^7$ represents halogen. In one aspect of that embodiment, $R^7$ represents fluoro. In another aspect of that embodiment, $R^7$ represents chloro. In a third embodiment, $R^7$ represents trifluoromethyl. In a fourth embodiment, $R^7$ represents $C_{1-6}$ alkyl. In one aspect of that embodiment, $R^7$ represents methyl. In another aspect of that embodiment, $R^7$ represents ethyl. In a fifth embodiment, $R^7$ represents $C_{1-6}$ alkoxy. In one aspect of that embodiment, $R^7$ represents methoxy.

Generally, $R^8$ represents hydrogen or trifluoromethyl.

In a first embodiment, $R^8$ represents hydrogen. In a second embodiment, $R^8$ represents halogen. In one aspect of that embodiment, $R^8$ represents fluoro. In another aspect of that embodiment, $R^8$ represents chloro. In a third embodiment, $R^8$ represents trifluoromethyl. In a fourth embodiment, $R^8$ represents $C_{1-6}$ alkyl. In one aspect of that embodiment, $R^8$ represents methyl. In another aspect of that embodiment, $R^8$ represents ethyl. In a fifth embodiment, $R^8$ represents $C_{1-6}$ alkoxy. In one aspect of that embodiment, $R^8$ represents methoxy.

Typically, $R^{12}$ represents hydrogen or methyl.

In a first embodiment, $R^{12}$ represents hydrogen. In a second embodiment, $R^{12}$ represents $C_{1-6}$ alkyl. In one aspect of that embodiment, $R^{12}$ represents methyl. In another aspect of that embodiment, $R^{12}$ represents ethyl.

Typical examples of suitable substituents which may be present on $R^a$, $R^b$, $R^c$, $R^d$ or $R^e$, or on the heterocyclic moiety —$NR^bR^c$, include halogen, $C_{1-6}$ alkyl, $C_{1-6}$ alkoxy, difluoromethoxy, trifluoromethoxy, $C_{1-6}$ alkoxy($C_{1-6}$)alkyl, $C_{1-6}$ alkylthio, $C_{1-6}$ alkyl-sulphinyl, $C_{1-6}$ alkylsulphonyl, hydroxy, hydroxy($C_{1-6}$)alkyl, amino($C_{1-6}$)alkyl, cyano, trifluoromethyl, oxo, $C_{2-6}$ alkylcarbonyl, carboxy, $C_{2-6}$ alkoxycarbonyl, $C_{2-6}$ alkylcarbonyl-oxy, amino, $C_{1-6}$ alkylamino, di($C_{1-6}$)alkylamino, phenylamino, pyridinylamino, $C_{2-6}$ alkyl-carbonylamino, $C_{2-6}$ alkylcarbonylamino($C_{1-6}$)alkyl, $C_{2-6}$ alkoxycarbonylamino, $C_{1-6}$ alkyl-sulphonylamino, aminocarbonyl, $C_{1-6}$ alkylaminocarbonyl and di($C_{1-6}$)alkylaminocarbonyl.

Typical examples of specific substituents which may be present on $R^a$, $R^b$, $R^c$, $R^d$ or $R^e$, or on the heterocyclic moiety —$NR^bR^c$, include fluoro, chloro, bromo, methyl, ethyl, isopropyl, methoxy, isopropoxy, difluoromethoxy, trifluoromethoxy, methoxymethyl, methylthio, ethylthio, methylsulphinyl, methylsulphonyl, hydroxy, hydroxymethyl, hydroxyethyl, aminomethyl, cyano, trifluoromethyl, oxo, acetyl, carboxy, methoxy-carbonyl, ethoxycarbonyl, tert-butoxycarbonyl, acetoxy, amino, methylamino, ethylamino, dimethylamino, phenylamino, pyridinylamino, acetylamino, tert-butoxycarbonylamino, acetylaminomethyl, methylsulphonylamino, aminocarbonyl, methylaminocarbonyl and dimethylaminocarbonyl.

Suitably, $R^a$ represents $C_{1-6}$ alkyl, aryl($C_{1-6}$)alkyl or heteroaryl($C_{1-6}$)alkyl, any of which groups may be optionally substituted by one or more substituents.

Selected values of $R^a$ include methyl, ethyl, benzyl and isoindolylpropyl, any of which groups may be optionally substituted by one or more substituents.

Selected examples of suitable substituents on $R^a$ include $C_{1-6}$ alkoxy and oxo.

Selected examples of specific substituents on $R^a$ include methoxy and oxo.

In one embodiment, $R^a$ represents optionally substituted $C_{1-6}$ alkyl. In one aspect of that embodiment, $R^a$ ideally represents unsubstituted $C_{1-6}$ alkyl, especially methyl. In another aspect of that embodiment, $R^a$ ideally represents substituted $C_{1-6}$ alkyl, e.g. methoxyethyl. In another embodiment, $R^a$ represents optionally substituted aryl. In one aspect of that embodiment, $R^a$ represents unsubstituted aryl, especially phenyl. In another aspect of that embodiment, $R^a$ represents monosubstituted aryl, especially methylphenyl. In another embodiment, $R^a$ represents optionally substituted aryl($C_{1-6}$)alkyl, ideally unsubstituted aryl($C_{1-6}$)alkyl, especially benzyl. In a further embodiment, $R^a$ represents optionally substituted heteroaryl. In a further embodiment, $R^a$ represents optionally substituted heteroaryl($C_{1-6}$)alkyl, e.g. dioxoisoindolylpropyl.

Specific values of $R^a$ include methyl, methoxyethyl, benzyl and dioxoisoindolyl-propyl.

In a particular aspect, $R^b$ represents hydrogen or trifluoromethyl; or $C_{1-6}$ alkyl, $C_{3-7}$ cycloalkyl, $C_{3-7}$ cycloalkyl($C_{1-6}$)alkyl, aryl, aryl($C_{1-6}$)alkyl, $C_{3-7}$ heterocycloalkyl, $C_{3-7}$ heterocycloalkyl($C_{1-6}$)alkyl, heteroaryl or heteroaryl($C_{1-6}$)alkyl, any of which groups may be optionally substituted by one or more substituents.

Selected values of $R^b$ include hydrogen; or $C_{1-6}$ alkyl, aryl($C_{1-6}$)alkyl, $C_{3-7}$ heterocycloalkyl or $C_{3-7}$ heterocycloalkyl($C_{1-6}$)alkyl, any of which groups may be optionally substituted by one or more substituents.

Typical values of $R^b$ include hydrogen and $C_{1-6}$ alkyl.

Illustratively, $R^b$ represents hydrogen or trifluoromethyl; or methyl, ethyl, n-propyl, isopropyl, n-butyl, 2-methylpropyl, tert-butyl, pentyl, hexyl, cyclopropyl, cyclobutyl, cyclopentyl, cyclohexyl, cyclopropylmethyl, cyclobutylmethyl, cyclopentylmethyl, cyclohexylmethyl, phenyl, benzyl, phenylethyl, azetidinyl, tetrahydrofuryl, tetrahydrothienyl, pyrrolidinyl, piperidinyl, homopiperidinyl, morpholinyl, azetidinylmethyl, tetrahydrofurylmethyl, pyrrolidinylmethyl, pyrrolidinylethyl, pyrrolidinylpropyl, thiazolidinylmethyl, imidazolidinylethyl, piperidinylmethyl, piperidinylethyl, tetrahydroquinolinylmethyl, piperazinylpropyl, morpholinylmethyl, morpholinylethyl, morpholinylpropyl, pyridinyl, indolylmethyl, pyrazolylmethyl, pyrazolylethyl, imidazolylmethyl, imidazolylethyl, benzimidazolylmethyl, triazolylmethyl, pyridinylmethyl or pyridinylethyl, any of which groups may be optionally substituted by one or more substituents.

Representative values of $R^b$ include hydrogen; or methyl, ethyl, n-propyl, benzyl, pyrrolidinyl or morpholinylpropyl, any of which groups may be optionally substituted by one or more substituents.

Selected examples of suitable substituents on $R^b$ include $C_{1-6}$ alkoxy, $C_{1-6}$ alkylthio, $C_{1-6}$ alkylsulphinyl, $C_{1-6}$ alkylsulphonyl, hydroxy, cyano, $C_{2-6}$ alkoxycarbonyl, di-($C_{1-6}$)alkylamino and $C_{2-6}$ alkoxycarbonylamino.

Selected examples of specific substituents on $R^b$ include methoxy, methylthio, methylsulphinyl, methylsulphonyl, hydroxy, cyano, tert-butoxycarbonyl, dimethylamino and tert-butoxycarbonylamino.

Specific values of $R^b$ include hydrogen, methyl, methoxyethyl, methylthioethyl, methylsulphinylethyl, methylsulphonylethyl, hydroxyethyl, cyanoethyl, dimethylamino-ethyl, tert-butoxycarbonylaminoethyl, dihydroxypropyl, benzyl, pyrrolidinyl, tert-butoxycarbonylpyrrolidinyl and morpholinylpropyl.

In one embodiment, $R^b$ represents hydrogen. In another embodiment, $R^b$ represents $C_{1-6}$ alkyl, especially methyl.

Selected values of $R^c$ include hydrogen; or $C_{1-6}$ alkyl, $C_{3-7}$ cycloalkyl or $C_{3-7}$ heterocycloalkyl, any of which groups may be optionally substituted by one or more substituents.

In a particular aspect, $R^c$ represents hydrogen, $C_{1-6}$ alkyl or $C_{3-7}$ cycloalkyl.

Representative values of $R^c$ include hydrogen; or methyl, cyclobutyl, cyclopentyl, cyclohexyl, tetrahydropyranyl and piperidinyl, any of which groups may be optionally substituted by one or more substituents.

Selected examples of suitable substituents on $R^e$ include $C_{2-6}$ alkylcarbonyl and $C_{2-6}$ alkoxycarbonyl.

Selected examples of specific substituents on $R^c$ include acetyl and tert-butoxycarbonyl.

Specific values of $R^c$ include hydrogen, methyl, cyclobutyl, cyclopentyl, cyclohexyl, tetrahydropyranyl, acetylpiperidinyl and tert-butoxycarbonylpiperidinyl, Suitably, $R^c$ represents hydrogen or $C_{1-6}$ alkyl. In one embodiment, $R^c$ is hydrogen.

In another embodiment, $R^c$ represents $C_{1-6}$ alkyl, especially methyl or ethyl, particularly methyl. In a further embodiment, $R^c$ represents $C_{3-7}$ cycloalkyl, e.g. cyclopropyl, cyclobutyl, cyclopentyl or cyclohexyl.

Alternatively, the moiety —$NR^bR^c$ may suitably represent azetidin-1-yl, pyrrolidin-1-yl, oxazolidin-3-yl, isoxazolidin-2-yl, thiazolidin-3-yl, isothiazolidin-2-yl, piperidin-1-yl, morpholin-4-yl, thiomorpholin-4-yl, piperazin-1-yl, homopiperidin-1-yl, homomorpholin-4-yl or homopiperazin-1-yl, any of which groups may be optionally substituted by one or more substituents.

Selected examples of suitable substituents on the heterocyclic moiety —$NR^bR^c$ include $C_{1-6}$ alkyl, $C_{1-6}$ alkylsulphonyl, hydroxy, hydroxy($C_{1-6}$)alkyl, amino($C_{1-6}$)alkyl, cyano, oxo, $C_{2-6}$ alkylcarbonyl, carboxy, $C_{2-6}$ alkoxycarbonyl, amino, $C_{2-6}$ alkylcarbonyl-amino, $C_{2-6}$ alkylcarbonylamino($C_{1-6}$)alkyl, $C_{2-6}$ alkoxycarbonylamino, $C_{1-6}$ alkyl-sulphonylamino and aminocarbonyl.

Selected examples of specific substituents on the heterocyclic moiety —$NR^bR^c$ include methyl, methylsulphonyl, hydroxy, hydroxymethyl, aminomethyl, cyano, oxo, acetyl, carboxy, ethoxycarbonyl, amino, acetylamino, acetylaminomethyl, tert-butoxy-carbonylamino, methylsulphonylamino and aminocarbonyl.

Specific values of the moiety —$NR^bR^c$ include azetidin-1-yl, hydroxyazetidin-1-yl, hydroxymethylazetidin- 1-yl, (hydroxy)(hydroxymethyl)azetidin- 1-yl, aminomethyl-azetidin-1-yl, cyanoazetidin- 1-yl, carboxyazetidin- 1-yl, amino azetidin- 1-yl, aminocarbonylazetidin-1-yl, pyrrolidin-1-yl, aminomethylpyrro lidin- l-yl, oxopyrrolidin- 1-yl, acetylaminomethylpyrrolidin-1-yl, tert-butoxycarbonylaminopyrrolidin-1-yl, oxo-oxazolidin-3-yl, hydroxyisoxazolidin-2-yl, thiazolidin-3-yl, oxothiazolidin-3-yl, dioxo-isothiazolidin-2-yl, piperidin-1-yl, hydroxypiperidin-1-yl, hydroxymethylpiperidin-1-yl, aminopiperidin- 1-yl, acetylaminopiperidin-1-yl, tert-butoxycarbonylaminopiperidin-1-yl, methylsulphonylaminopiperidin-1-yl, morpholin-4-yl, piperazin-1-yl, methylpiperazin-1-yl, methylsulphonylpiperazin-1-yl, oxopiperazin-1-yl, acetylpiperazin-1-yl, ethoxycarbonylpiperazin-1-yl and oxohomopiperazin- 1-yl.

Suitably, $R^d$ represents hydrogen; or $C_{1-6}$ alkyl, aryl or heteroaryl, any of which groups may be optionally substituted by one or more substituents.

Selected examples of suitable values for $R^d$ include hydrogen, methyl, ethyl, isopropyl, 2-methylpropyl, tert-butyl, cyclopropyl, cyclobutyl, phenyl, thiazolidinyl, thienyl, imidazolyl and thiazolyl, any of which groups may be optionally substituted by one or more substituents.

Selected examples of suitable substituents on $R^d$ include halogen, $C_{1-6}$ alkyl, $C_{1-6}$ alkoxy, oxo, $C_{2-6}$ alkylcarbonyloxy and di($C_{1-6}$)alkylamino.

Selected examples of particular substituents on $R^d$ include fluoro, methyl, methoxy, oxo, acetoxy and dimethylamino.

In one embodiment, $R^d$ represents hydrogen. In another embodiment, $R^d$ represents optionally substituted $C_{1-6}$ alkyl. In one aspect of that embodiment, $R^d$ ideally represents unsubstituted $C_{1-6}$ alkyl, e.g. methyl, ethyl, isopropyl, 2-methylpropyl or tert-butyl, especially methyl. In another aspect of that embodiment, $R^d$ ideally represents substituted $C_{1-6}$ alkyl, e.g. substituted methyl or substituted ethyl, including acetoxymethyl, dimethylaminomethyl and trifluoroethyl. In another embodiment, $R^d$ represents optionally substituted aryl. In one aspect of that embodiment, $R^d$ represents unsubstituted aryl, especially phenyl. In another aspect of that embodiment, $R^d$ represents monosubstituted aryl, especially methylphenyl. In a further aspect of that embodiment, $R^d$ represents disubstituted aryl, e.g. dimethoxyphenyl. In a further embodiment, $R^d$ represents optionally substituted heteroaryl, e.g. thienyl, chlorothienyl, methylthienyl, methylimidazolyl or thiazolyl. In another embodiment, $R^d$ represents optionally substituted $C_{3-7}$ cycloalkyl, e.g. cyclopropyl or cyclobutyl. In a further embodiment, $R^d$ represents optionally substituted $C_{3-7}$ heterocycloalkyl, e.g. thiazolidinyl or oxo-thiazolidinyl.

Selected examples of specific values for $R^d$ include hydrogen, methyl, acetoxy-methyl, dimethylaminomethyl, ethyl, trifluoroethyl, isopropyl, 2-methylpropyl, tert-butyl, cyclopropyl, cyclobutyl, phenyl, dimethoxyphenyl, thiazolidinyl, oxothiazolidinyl, thienyl, chlorothienyl, methylthienyl, methylimidazolyl and thiazolyl.

Suitably, $R^e$ represents $C_{1-6}$ alkyl or aryl, either of which groups may be optionally substituted by one or more substituents.

Selected examples of suitable substituents on $R^e$ include $C_{1-6}$ alkyl, especially methyl.

In one embodiment, $R^e$ represents optionally substituted $C_{1-6}$ alkyl, ideally unsubstituted $C_{1-6}$ alkyl, e.g. methyl or propyl, especially methyl. In another embodiment, $R^e$ represents optionally substituted aryl. In one aspect of that embodiment, $R^e$ represents unsubstituted aryl, especially phenyl. In another aspect of that embodiment, $R^e$ represents monosubstituted aryl, especially methylphenyl. In a further embodiment, $R^e$ represents optionally substituted heteroaryl.

Selected values of $R^e$ include methyl, propyl and methylphenyl.

Typical examples of optional substituents on $R^f$ include one, two or three substituents independently selected from hydroxy and carboxy.

Generally, $R^f$ represents hydrogen or $C_{1-6}$ alkyl.

In a first embodiment, $R^f$ represents hydrogen. In a second embodiment, $R^f$ represents $C_{1-6}$ alkyl. In a first aspect of that embodiment, $R^f$ represents methyl. In a second aspect of that embodiment, $R^f$ represents ethyl. In a third aspect of that embodiment, $R^f$ represents ethyl.

Typical values of $R^f$ include hydrogen, methyl, ethyl and isopropyl.

Generally, $R^g$ represents hydrogen, —$SO_2R^a$, —$COR^d$ or —$CO_2R^d$; or $R^g$ represents $C_{1-6}$ alkyl or heteroaryl, either of which groups may be optionally substituted by one or more substituents.

Typical examples of optional substituents on $R^g$ include one, two or three substituents independently selected from halogen, trifluoromethyl, $C_{1-6}$ alkyl, $C_{4-9}$ heterobicycloalkyl, hydroxy, $C_{1-6}$ alkoxy, $C_{1-6}$ alkylsulphonyl, carboxy and $C_{2-6}$ alkoxycarbonyl.

Typical examples of optional substituents on $R^g$ include one, two or three substituents independently selected from fluoro, chloro, trifluoromethyl, methyl, 3,7-dioxa-9-azabicyclo[3.3.1]nonan-9-yl, hydroxy, methoxy, methylsulphonyl, carboxy and ethoxycarbonyl.

In a first embodiment, $R^g$ represents hydrogen. In a second embodiment, $R^g$ represents —$SO_2R^a$. In a third embodiment, $R^g$ represents —$COR^d$. In a fourth embodiment, $R^g$ represents —$CO_2R^d$. In a fifth embodiment, $R^g$ represents optionally substituted $C_{1-6}$ alkyl. In a first aspect of that embodiment, $R^g$ represents optionally substituted methyl. In a second aspect of that embodiment, $R^g$ represents optionally substituted ethyl. In a third aspect of that embodiment, $R^g$ represents optionally substituted isopropyl. In a sixth embodiment, $R^g$ represents optionally substituted $C_{3-7}$ cycloalkyl. In a seventh embodiment, $R^g$ represents optionally substituted $C_{3-7}$ heterocycloalkyl. In an eighth embodiment, $R^g$ represents optionally substituted heteroaryl. In one aspect of that embodiment, $R^g$ represents optionally substituted pyrimidinyl.

Illustrative values of $R^g$ include hydrogen and methyl.

One sub-group of the compounds of formula (IB) above is represented by the compounds of formula (IIA) and N-oxides thereof, and pharmaceutically acceptable salts thereof:

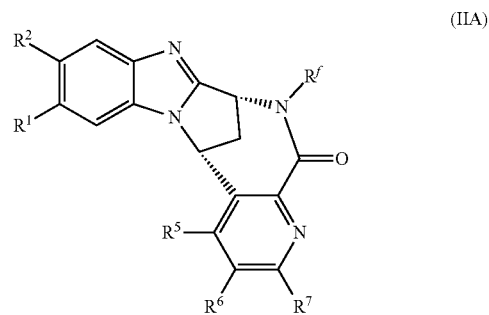

(IIA)

wherein $R^1$, $R^2$, $R^5$, $R^6$, $R^7$ and $R^f$ are as defined above.

A particular subset of the compounds of formula (IIA) above is represented by the compounds of formula (IIA-1) and N-oxides thereof, and pharmaceutically acceptable salts thereof:

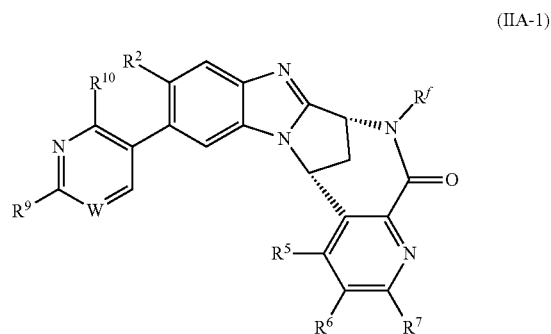

(IIA-1)

wherein
W represents N, CH or CF;
$R^9$ represents hydroxy($C_{1-6}$)alkyl or amino($C_{1-6}$)alkyl;
$R^{10}$ represents hydrogen or $C_{1-6}$ alkyl; and
$R^2$, $R^5$, $R^6$, $R^7$ and $R^f$ are as defined above.
Generally, W represents N or CH.
Suitably, W represents N or CF.
In one embodiment, W represents N. In another embodiment, W represents CH. In a further embodiment, W represents CF.
Typically, $R^g$ represents hydroxyisopropyl or aminoisopropyl.
Typical values of $R^g$ include 2-hydroxyprop-2-yl and 2-aminoprop-2-yl.

In one embodiment, $R^g$ represents hydroxy($C_{1-6}$)alkyl. In a particular aspect of that embodiment, $R^g$ represents hydroxyisopropyl, especially 2-hydroxyprop-2-yl.

In another embodiment, $R^g$ represents amino($C_{1-6}$)alkyl. In a particular aspect of that embodiment, $R^g$ represents aminoisopropyl, especially 2-aminoprop-2-yl.

Typically, $R^{10}$ represents hydrogen or methyl.

In one embodiment, $R^{10}$ represents hydrogen. In another embodiment, $R^{10}$ represents $C_{1-6}$ alkyl. In one aspect of that embodiment, $R^{10}$ represents methyl.

Another subset of the compounds of formula (IIA) above is represented by the compounds of formula (IIA-2) and N-oxides thereof, and pharmaceutically acceptable salts thereof:

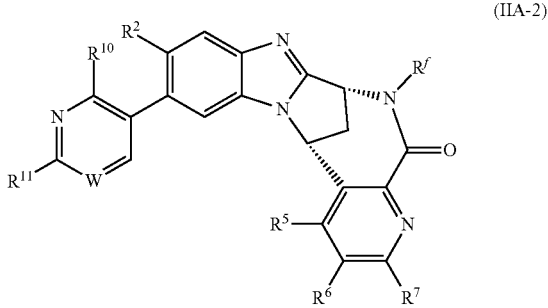

(IIA-2)

wherein
$R^{11}$ represents a group of formula (a), (b), (c), (d), (e), (f) or (g):

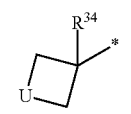 (a)

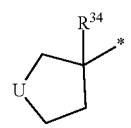 (b)

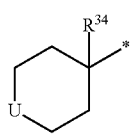 (c)

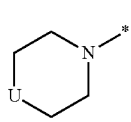 (d)

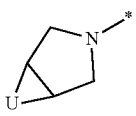 (e)

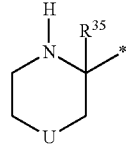 (f)

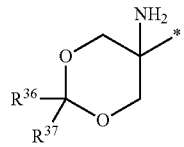 (g)

in which the asterisk (*) represents the site of attachment to the remainder of the molecule;

U represents O, S, S(O), S(O)$_2$, S(O)(NR$^b$), N(R$^{31}$) or C(R$^{32}$)(R$^{33}$);

$R^{31}$ represents hydrogen, cyano($C_{1-6}$)alkyl, $C_{1-6}$ alkyl, trifluoromethyl, trifluoro-ethyl, $C_{1-6}$ alkylsulphonyl, ($C_{1-6}$) alkylsulphonyl($C_{1-6}$)alkyl, formyl, $C_{2-6}$ alkylcarbonyl, carboxy, carboxy($C_{1-6}$)alkyl, $C_{2-6}$ alkoxycarbonyl, $C_{2-6}$ alkoxycarbonyl($C_{1-6}$)alkyl, tetrazolyl($C_{1-6}$)alkyl, aminocarbonyl, $C_{1-6}$ alkylaminocarbonyl, di($C_{1-6}$)alkylamino-carbonyl, aminosulphonyl, $C_{1-6}$ alkylaminosulphonyl or di($C_{1-6}$)alkylaminosulphonyl; $R^{32}$ represents hydrogen, halogen, cyano, hydroxy, hydroxy($C_{1-6}$)alkyl, $C_{1-6}$ alkylsulphonyl, formyl, carboxy, carboxy($C_{1-6}$)alkyl, $C_{2-6}$ alkoxycarbonyl, $C_{2-6}$ alkoxycarbonyl($C_{1-6}$)alkyl, aminosulphonyl, ($C_{1-6}$)alkylsulphoximinyl, [($C_{1-6}$)alkyl][N—($C_{1-6}$)alkyl]sulphoximinyl, ($C_{1-6}$)alkylsulphonylaminocarbonyl, ($C_{2-6}$)alkylcarbonylamino-sulphonyl, ($C_{1-6}$)alkoxyaminocarbonyl, tetrazolyl or hydroxyoxadiazolyl;

$R^{33}$ represents hydrogen, halogen, $C_{1-6}$ alkyl, difluoromethyl, trifluoromethyl, hydroxy, hydroxy($C_{1-6}$)alkyl, $C_{1-6}$ alkoxy, amino or carboxy;

$R^{34}$ represents hydrogen, halogen, halo($C_{1-6}$)alkyl, hydroxy, $C_{1-6}$ alkoxy, $C_{1-6}$ alkylthio, $C_{1-6}$ alkylsulphinyl, $C_{1-6}$ alkylsulphonyl, amino, $C_{1-6}$ alkylamino, di($C_{1-6}$)alkylamino, ($C_{2-6}$)alkylcarbonylamino, ($C_{2-6}$)alkylcarbonylamino($C_{1-6}$)alkyl, ($C_{1-6}$)alkyl-sulphonylamino or ($C_{1-6}$) alkylsulphonylamino($C_{1-6}$)alkyl;

$R^{35}$ represents hydrogen or $C_{1-6}$ alkyl;

$R^{36}$ and $R^{37}$ independently represent $C_{1-6}$ alkyl; or $R^{36}$ and $R^{37}$, when taken together with the carbon atom to which they are both attached, represent $C_{3-7}$ cycloalkyl; and W, $R^2$, $R^5$, $R^6$, $R^7$, $R^{10}$, $R^b$ and $R^f$ are as defined above.

Generally, U represents O, S(O)$_2$, N(R$^{31}$) or C(R$^{32}$)(R$^{33}$).

Typically, U represents O, N(R$^{31}$) or C(R$^{32}$)(R$^{33}$).

In a first embodiment, U represents O. In a second embodiment, U represents S. In a third embodiment, U represents S(O). In a fourth embodiment, U represents S(O)$_2$. In a fifth embodiment, U represents S(O)(NR$^b$). In a sixth embodiment, U represents N(R$^{31}$). In a seventh embodiment, U represents C(R$^{32}$)(R$^{33}$).

Typical values of $R^{31}$ include hydrogen, cyanoethyl, methyl, ethyl, isopropyl, trifluoromethyl, trifluoroethyl, methylsulphonyl, methylsulphonylethyl, formyl, acetyl, carboxy, carboxymethyl, carboxyethyl, methoxycarbonyl, ethoxycarbonyl, tert-butoxy-carbonyl, ethoxycarbonylmethyl, ethoxycarbonylethyl, tetrazolylmethyl, aminocarbonyl, methylaminocarbonyl, dimethylaminocarbonyl, aminosulphonyl, methylaminosulphonyl and dimethylaminosulphonyl.

Suitably, $R^{31}$ represents hydrogen or $C_{1-6}$ alkyl.

Suitable values of $R^{31}$ include hydrogen and methyl.

In a first embodiment, $R^{31}$ represents hydrogen. In a second embodiment, $R^{31}$ represents $C_{1-6}$ alkyl, especially methyl.

Typical values of $R^{32}$ include hydrogen, fluoro, cyano, hydroxy, hydroxymethyl, methylsulphonyl, formyl, carboxy, carboxymethyl, carboxyethyl, methoxycarbonyl, ethoxycarbonyl, tert-butoxycarbonyl, methoxycarbonylmethyl, methoxycarbonylethyl, ethoxycarbonylmethyl, ethoxycarbonylethyl, aminosulphonyl, methylsulphoximinyl, (methyl)(N-methyl)sulphoximinyl, methylsulphonylaminosulphonyl, acetylaminosulphonyl, methoxyaminocarbonyl, tetrazolyl and hydroxyoxadiazolyl.

Suitably, $R^{32}$ represents hydrogen, halogen or cyano.

Suitable values of $R^{32}$ include hydrogen, fluoro and cyano.

In a first embodiment, $R^{32}$ represents hydrogen. In a second embodiment, $R^{32}$ represents halogen, especially fluoro. In a third embodiment, $R^{32}$ represents cyano.

Generally, $R^{33}$ represents hydrogen, halogen, $C_{1-6}$ alkyl, difluoromethyl or trifluoromethyl.

Typical values of $R^{33}$ include hydrogen, fluoro, methyl, ethyl, isopropyl, difluoromethyl, trifluoromethyl, hydroxy, hydroxymethyl, methoxy, amino and carboxy.

Suitably, $R^{33}$ represents hydrogen, halogen or difluoromethyl.

Suitable values of $R^{33}$ include hydrogen, fluoro and difluoromethyl.

In a first embodiment, $R^{33}$ represents hydrogen. In a second embodiment, $R^{33}$ represents halogen. In one aspect of that embodiment, $R^{33}$ represents fluoro. In a third embodiment, $R^{33}$ represents $C_{1-6}$ alkyl. In a first aspect of that embodiment, $R^{33}$ represents methyl. In a second aspect of that embodiment, $R^{33}$ represents ethyl. In a third aspect of that embodiment, $R^{33}$ represents isopropyl. In a fourth embodiment, $R^{33}$ represents difluoromethyl. In a fifth embodiment, $R^{33}$ represents trifluoromethyl. In a sixth embodiment, $R^{33}$ represents hydroxy. In a seventh embodiment, $R^{33}$ represents hydroxy($C_{1-6}$)alkyl. In one aspect of that embodiment, $R^{33}$ represents hydroxymethyl. In an eighth embodiment, $R^{33}$ represents $C_{1-6}$ alkoxy. In one aspect of that embodiment, $R^{33}$ represents methoxy. In a ninth embodiment, $R^{33}$ represents amino. In a tenth embodiment, $R^{33}$ represents carboxy.

In a first embodiment, $R^{34}$ represents hydrogen. In a second embodiment, $R^{34}$ represents halogen. In one aspect of that embodiment, $R^{34}$ represents fluoro. In a third embodiment, $R^{34}$ represents halo($C_{1-6}$)alkyl. In one aspect of that embodiment, $R^{34}$ represents fluoromethyl. In a fourth embodiment, $R^{34}$ represents hydroxy. In a fifth embodiment, $R^{34}$ represents $C_{1-6}$ alkoxy, especially methoxy. In a sixth embodiment, $R^{34}$ represents $C_{1-6}$ alkylthio, especially methylthio. In a seventh embodiment, $R^{34}$ represents $C_{1-6}$ alkylsulphinyl, especially methylsulphinyl. In an eighth embodiment, $R^{34}$ represents $C_{1-6}$ alkylsulphonyl, especially methylsulphonyl. In a ninth embodiment, $R^{34}$ represents amino. In a tenth embodiment, $R^{34}$ represents $C_{1-6}$ alkylamino, especially methylamino. In an eleventh embodiment, $R^{34}$ represents di($C_{1-6}$)alkylamino, especially dimethylamino. In a twelfth embodiment, $R^{34}$ represents ($C_{2-6}$)alkylcarbonylamino, especially acetylamino. In a thirteenth embodiment, $R^{34}$ represents ($C_{2-6}$)alkylcarbonylamino($C_{1-6}$)alkyl, especially acetylaminomethyl. In a fourteenth embodiment, $R^{34}$ represents ($C_{1-6}$)alkylsulphonyl-amino, especially methylsulphonylamino. In a fifteenth embodiment, $R^{34}$ represents ($C_{1-6}$)alkylsulphonylamino($C_{1-6}$)alkyl, especially methylsulphonylaminomethyl.

Suitably, $R^{34}$ represents hydrogen or amino.

Suitable values of $R^{35}$ include hydrogen and methyl.

In a first embodiment, $R^{35}$ represents hydrogen. In a second embodiment, $R^{35}$ represents $C_{1-6}$ alkyl, especially methyl.

Suitably, $R^{36}$ represents methyl or ethyl, especially methyl.

Suitably, $R^{37}$ represents methyl or ethyl, especially methyl.

Alternatively, $R^{36}$ and $R^{37}$, when taken together with the carbon atom to which they are both attached, may suitably represent cyclopropyl, cyclobutyl, cyclopentyl, cyclohexyl or cycloheptyl.

Another sub-group of the compounds of formula (IB) above is represented by the compounds of formula (IIB) and N-oxides thereof, and pharmaceutically acceptable salts thereof:

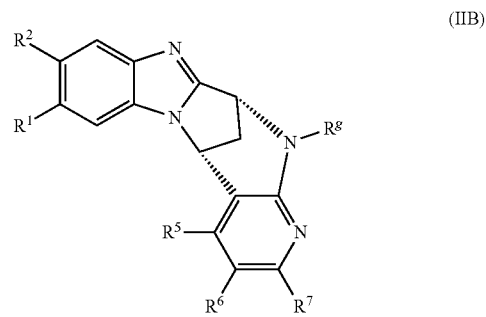

(IIB)

wherein $R^1$, $R^2$, $R^5$, $R^6$, $R^7$ and $R^g$ are as defined above.

A particular subset of the compounds of formula (IIB) above is represented by the compounds of formula (IIB-1) and N-oxides thereof, and pharmaceutically acceptable salts thereof:

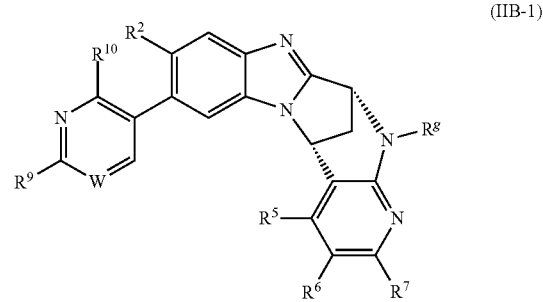

(IIB-1)

wherein W, $R^2$, $R^5$, $R^6$, $R^7$, $R^g$, $R^{10}$ and $R^g$ are as defined above.

Another subset of the compounds of formula (IIB) above is represented by the compounds of formula (IIB-2) and N-oxides thereof, and pharmaceutically acceptable salts thereof:

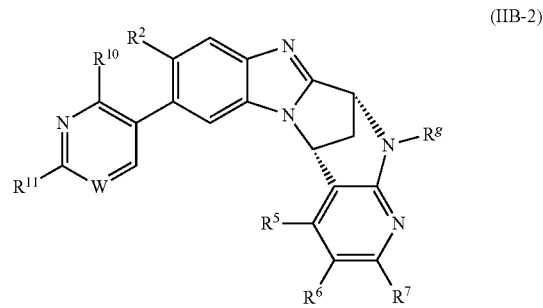

(IIB-2)

wherein W, $R^2$, $R^5$, $R^6$, $R^7$, $R^{10}$, $R^{11}$ and $R^g$ are as defined above.

Specific novel compounds in accordance with the present invention include each of the compounds whose preparation is described in the accompanying Examples, and pharmaceutically acceptable salts thereof.

The compounds in accordance with the present invention are beneficial in the treatment and/or prevention of various human ailments. These include autoimmune and inflammatory disorders; neurological and neurodegenerative disorders; pain and nociceptive disorders; cardiovascular disorders; metabolic disorders; ocular disorders; and oncological disorders.

Inflammatory and autoimmune disorders include systemic autoimmune disorders, autoimmune endocrine disorders and organ-specific autoimmune disorders. Systemic autoimmune disorders include systemic lupus erythematosus (SLE), psoriasis, psoriatic arthropathy, vasculitis, inflammatory myopathy (including polymyositis, dermatomyositis and inclusion body myositis), scleroderma, multiple sclerosis, systemic sclerosis, ankylosing spondylitis, rheumatoid arthritis, non-specific inflammatory arthritis, juvenile inflammatory arthritis, juvenile idiopathic arthritis (including oligoarticular and polyarticular forms thereof), anaemia of chronic disease (ACD), Still's disease (juvenile and/or adult onset), Behçet's disease and Sjögren's syndrome. Autoimmune endocrine disorders include thyroiditis. Organ-specific autoimmune disorders include Addison's disease, haemolytic or pernicious anaemia, acute kidney injury (AKI; including cisplatin-induced AKI), diabetic nephropathy (DN), obstructive uropathy (including cisplatin-induced obstructive uropathy), glomerulonephritis (including Goodpasture's syndrome, immune complex-mediated glomerulonephritis and antineutrophil cytoplasmic antibodies (ANCA)-associated glomerulonephritis), lupus nephritis (LN), minimal change disease, Graves' disease, idiopathic thrombocytopenic purpura, inflammatory bowel disease (including Crohn's disease, ulcerative colitis, indeterminate colitis and pouchitis), pemphigus, atopic dermatitis, autoimmune hepatitis, primary biliary cirrhosis, autoimmune pneumonitis, autoimmune carditis, myasthenia gravis, spontaneous infertility, osteoporosis, osteopenia, erosive bone disease, chondritis, cartilage degeneration and/or destruction, fibrosing disorders (including various forms of hepatic and pulmonary fibrosis), asthma, rhinitis, chronic obstructive pulmonary disease (COPD), respiratory distress syndrome, sepsis, fever, muscular dystrophy (including Duchenne muscular dystrophy), organ transplant rejection (including kidney allograft rejection), scleritis (including giant cell arteritis scleritis), Takayasu arteritis, hidradenitis suppurativa, pyoderma gangrenosum, sarcoidosis, polymyalgia rheumatic and axial spondyloarthritis.

Neurological and neurodegenerative disorders include Alzheimer's disease, Parkinson's disease, Huntington's disease, ischaemia, stroke, amyotrophic lateral sclerosis, spinal cord injury, head trauma, seizures and epilepsy.

Cardiovascular disorders include thrombosis, cardiac hypertrophy, hypertension, irregular contractility of the heart (e.g. during heart failure), and sexual disorders (including erectile dysfunction and female sexual dysfunction). Modulators of TNFα function may also be of use in the treatment and/or prevention of myocardial infarction (see J. J. Wu et al., *JAMA*, 2013, 309, 2043-2044).

Metabolic disorders include diabetes (including insulin-dependent diabetes mellitus and juvenile diabetes), dyslipidemia and metabolic syndrome.

Ocular disorders include retinopathy (including diabetic retinopathy, proliferative retinopathy, non-proliferative retinopathy and retinopathy of prematurity), macular oedema (including diabetic macular oedema), age-related macular degeneration (ARMD), vascularisation (including corneal vascularisation and neovascularisation), retinal vein occlusion, and various forms of uveitis (including iritis) and keratitis Oncological disorders, which may be acute or chronic, include proliferative disorders, especially cancer, and cancer-associated complications (including skeletal complications, cachexia and anaemia). Particular categories of cancer include haematological malignancy (including leukaemia and lymphoma) and non-haematological malignancy (including solid tumour cancer, sarcoma, meningioma, glioblastoma multiforme, neuroblastoma, melanoma, gastric carcinoma and renal cell carcinoma). Chronic leukaemia may be myeloid or lymphoid. Varieties of leukaemia include lymphoblastic T cell leukaemia, chronic myelogenous leukaemia (CML), chronic lymphocytic/lymphoid leukaemia (CLL), hairy-cell leukaemia, acute lymphoblastic leukaemia (ALL), acute myelogenous leukaemia (AML), myelodysplastic syndrome, chronic neutrophilic leukaemia, acute lymphoblastic T cell leukaemia, plasmacytoma, immunoblastic large cell leukaemia, mantle cell leukaemia, multiple myeloma, acute megakaryoblastic leukaemia, acute megakaryocytic leukaemia, promyelocytic leukaemia and erythroleukaemia. Varieties of lymphoma include malignant lymphoma, Hodgkin's lymphoma, non-Hodgkin's lymphoma, lymphoblastic T cell lymphoma, Burkitt's lymphoma, follicular lymphoma, MALT1 lymphoma and marginal zone lymphoma. Varieties of non-haematological malignancy include cancer of the prostate, lung, breast, rectum, colon, lymph node, bladder, kidney, pancreas, liver, ovary, uterus, cervix, brain, skin, bone, stomach and muscle. Modulators of TNFα function may also be used to increase the safety of the potent anticancer effect of TNF (see F. V. Hauwermeiren et al., *J. Clin. Invest.*, 2013, 123, 2590-2603).

The present invention also provides a pharmaceutical composition which comprises a compound in accordance with the invention as described above, or a pharmaceutically acceptable salt or solvate thereof, in association with one or more pharmaceutically acceptable carriers.

Pharmaceutical compositions according to the invention may take a form suitable for oral, buccal, parenteral, nasal, topical, ophthalmic or rectal administration, or a form suitable for administration by inhalation or insufflation.

For oral administration, the pharmaceutical compositions may take the form of, for example, tablets, lozenges or capsules prepared by conventional means with pharmaceutically acceptable excipients such as binding agents (e.g. pregelatinised maize starch, polyvinylpyrrolidone or hydroxypropyl methyl cellulose); fillers (e.g. lactose, microcrystalline cellulose or calcium hydrogenphosphate); lubricants (e.g. magnesium stearate, talc or silica); disintegrants (e.g. potato starch or sodium glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents, emulsifying agents, non-aqueous vehicles or preservatives. The preparations may also contain buffer salts, flavouring agents, colouring agents or sweetening agents, as appropriate.

Preparations for oral administration may be suitably formulated to give controlled release of the active compound.

For buccal administration, the compositions may take the form of tablets or lozenges formulated in conventional manner.

The compounds of formula (I) may be formulated for parenteral administration by injection, e.g. by bolus injection or infusion. Formulations for injection may be presented in unit dosage form, e.g. in glass ampoules or multi-dose containers, e.g. glass vials. The compositions for injection may take such forms as suspensions, solutions or emulsions in oily or aqueous vehicles, and may contain formulatory agents such as suspending, stabilising, preserving and/or dispersing agents. Alternatively, the active ingredient may be in powder form for constitution with a suitable vehicle, e.g. sterile pyrogen-free water, before use.

In addition to the formulations described above, the compounds of formula (I) may also be formulated as a depot preparation. Such long-acting formulations may be administered by implantation or by intramuscular injection.

For nasal administration or administration by inhalation, the compounds according to the present invention may be conveniently delivered in the form of an aerosol spray presentation for pressurised packs or a nebuliser, with the use of a suitable propellant, e.g. dichlorodifluoromethane, fluorotrichloromethane, dichlorotetrafluoroethane, carbon dioxide or other suitable gas or mixture of gases.

The compositions may, if desired, be presented in a pack or dispenser device which may contain one or more unit dosage forms containing the active ingredient. The pack or dispensing device may be accompanied by instructions for administration.

For topical administration the compounds of use in the present invention may be conveniently formulated in a suitable ointment containing the active component suspended or dissolved in one or more pharmaceutically acceptable carriers. Particular carriers include, for example, mineral oil, liquid petroleum, propylene glycol, polyoxyethylene, polyoxypropylene, emulsifying wax and water. Alternatively, the compounds of use in the present invention may be formulated in a suitable lotion containing the active component suspended or dissolved in one or more pharmaceutically acceptable carriers. Particular carriers include, for example, mineral oil, sorbitan monostearate, polysorbate 60, cetyl esters wax, cetearyl alcohol, benzyl alcohol, 2-octyldodecanol and water.

For ophthalmic administration the compounds of use in the present invention may be conveniently formulated as micronized suspensions in isotonic, pH-adjusted sterile saline, either with or without a preservative such as a bactericidal or fungicidal agent, for example phenylmercuric nitrate, benzylalkonium chloride or chlorhexidine acetate. Alternatively, for ophthalmic administration compounds may be formulated in an ointment such as petrolatum.

For rectal administration the compounds of use in the present invention may be conveniently formulated as suppositories. These can be prepared by mixing the active component with a suitable non-irritating excipient which is solid at room temperature but liquid at rectal temperature and so will melt in the rectum to release the active component. Such materials include, for example, cocoa butter, beeswax and polyethylene glycols.

The quantity of a compound of use in the invention required for the prophylaxis or treatment of a particular condition will vary depending on the compound chosen and the condition of the patient to be treated. In general, however, daily dosages may range from around 10 ng/kg to 1000 mg/kg, typically from 100 ng/kg to 100 mg/kg, e.g. around 0.01 mg/kg to 40 mg/kg body weight, for oral or buccal administration, from around 10 ng/kg to 50 mg/kg body weight for parenteral administration, and from around 0.05 mg to around 1000 mg, e.g. from around 0.5 mg to around 1000 mg, for nasal administration or administration by inhalation or insufflation.

If desired, a compound in accordance with the present invention may be co-administered with another pharmaceutically active agent, e.g. an anti-inflammatory molecule.

The compounds of formula (I) above may be prepared by a process which comprises the intramolecular cyclisation of an intermediate of formula (III):

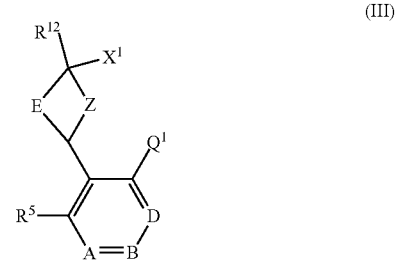

(III)

wherein
X$^1$ represents hydroxy, —SH, —CH$_2$OH, —CO$_2$H, —NHR$^f$, —NHR$^g$, —C(O)—NHR$^f$, Y or —CH$_2$—Y;
Q$^1$ represents hydrogen, halogen, hydroxy, amino, —SR$^i$, —CO$_2$H, —CH$_2$—Y, —CO—R or —CH(OH)CF$_3$;
Y represents a suitable leaving group;
R$^i$ represents hydrogen, methyl, —CH$_2$CO$_2$CH$_2$CH$_3$ or —(CH$_2$)$_2$CO$_2$CH$_2$CH(CH$_2$CH$_3$)[(CH$_2$)$_3$CH$_3$];
R$^j$ represents hydrogen or methyl; and
A, B, D, Z, E, R$^5$, R$^{12}$, R$^f$ and R$^g$ are as defined above.

Suitably, the leaving group Y represents halogen or (C$_{1-6}$)alkylsulphonyloxy.

Appositely, Y represents bromo or methylsulphonyloxy.

The compounds of formula (I) wherein R$^{12}$ represents hydrogen and —X-Q-represents —O— may be prepared by the intramolecular cyclization of an intermediate of formula (III) wherein R$^{12}$ represents hydrogen, X$^1$ represents a leaving group Y, e.g. halogen, preferably bromo, and Q$^1$ represents hydroxy, in the presence of a base, for example sodium hydride or silver carbonate.

Alternatively, the compounds of formula (I) wherein R$^{12}$ represents hydrogen and —X-Q- represents —O— may be prepared by the intramolecular cyclization of an intermediate of formula (III) wherein R$^{12}$ represents hydrogen, X$^1$ represents hydroxy and Q$^1$ represents a leaving group Y, e.g. halogen, preferably bromo, in the presence of a base, e.g. an inorganic base such as cesium carbonate, and copper iodide, at an elevated temperature.

The compounds of formula (I) wherein R$^{12}$ represents hydrogen and —X-Q-represents —O—C(=CH—CN)— may be prepared by the intramolecular cyclization of an intermediate of formula (III) wherein R$^{12}$ represents hydrogen, X$^1$ represents hydroxy and Q$^1$ represents —CO$_2$H, in the presence of cyanomethylenetributylphosphorane.

The reaction is conveniently performed at an elevated temperature in a suitable solvent, e.g. toluene.

The resulting compounds may be transformed into the corresponding compounds of formula (I) wherein R$^{12}$ represents hydrogen and —X-Q- represents —O—C(O)— by treatment with a base, e.g. potassium hydroxide.

Alternatively, the compounds of formula (I) wherein $R^{12}$ represents hydrogen and —X-Q- represents —O—C(O)— may be prepared by the intramolecular cyclization of an intermediate of formula (III) wherein $R^{12}$ represents hydrogen, $X^1$ represents hydroxy and $Q^1$ represents —$CO_2H$, in the presence of an acid, e.g. a mineral acid, in a suitable solvent.

The compounds of formula (I) wherein $R^{12}$ represents hydrogen and —X-Q-represents —C(O)—O— may be prepared by the intramolecular cyclization of an intermediate of formula (III) wherein $R^{12}$ represents hydrogen, $X^1$ represents —$CO_2H$ and $Q^1$ represents hydroxy, in the presence of thionyl chloride, or alternatively by using a suitable coupling reagent according to methods known to the person skilled in the art.

The compounds of formula (I) wherein $R^{12}$ represents hydrogen and —X-Q-represents —S— may be prepared by the intramolecular cyclization of an intermediate of formula (III) wherein $X^1$ represents —SH and $Q^1$ represents halogen, in the presence of a transition metal catalyst, according to a method analogous to that described by Stambuli J. et al. in *J. Org. Chem.*, 2009, 74, 4005-4008.

Alternatively, the compounds of formula (I) wherein $R^{12}$ represents hydrogen and —X-Q- represents —S— may be prepared in a two-step procedure which comprises: (i) reacting an intermediate of formula (III) wherein $R^{12}$ represents hydrogen, $X^1$ represents hydroxy and $Q^1$ represents —$(CH_2)_2CO_2CH_2CH(CH_2CH_3)[(CH_2)_3CH_3]$ with methane-sulphonyl chloride in the presence of a base, e.g. N,N-diisopropylethylamine, in a suitable solvent, e.g. tetrahydrofuran, to afford the corresponding compound wherein $X^1$ represents a leaving group Y, in which Y is a mesylate moiety; followed by (ii) intramolecular cyclization of the compound thereby obtained by treatment with sodium ethoxide.

The compounds of formula (I) wherein $R^{12}$ represents hydrogen and —X-Q-represents —N($R^g$)— may be prepared by the intramolecular cyclization of an intermediate of formula (III) wherein $R^{12}$ represents hydrogen, $X^1$ represents —$NHR^g$ and $Q^1$ represents halogen, in the presence of a transition metal catalyst, according to methods known to the person skilled in the art.

The intramolecular cyclization may be accomplished by utilizing palladium(II) acetate in the presence of (±)-2,2'-bis(diphenylphosphino)- 1,1'-binaphthalene (BINAP) or 4,5-bis(diphenylphosphino)-9,9-dimethylxanthene (Xantphos). The reaction may conveniently be effected in the presence of base, e.g. potassium carbonate or cesium carbonate, in a suitable solvent, e.g. toluene or 1,4-dioxane, at an elevated temperature.

Alternatively, the compounds of formula (I) wherein $R^{12}$ represents hydrogen and —X-Q- represents —N($R^g$)—, in which $R^g$ represents hydrogen, may be prepared by the intramolecular cyclization of an intermediate of formula (III) wherein $R^{12}$ represents hydrogen, $X^1$ is a leaving group Y, e.g. methylsulphonyloxy, and $Q^1$ represents amino. The reaction is conveniently effected in a three-step procedure which comprises: (i) protecting the amino group $Q^1$ with a suitable N-protecting group, e.g. tert-butoxy-carbonyl, according to methods known to the person skilled in the art; (ii) intramolecular cyclization by addition of a suitable base, e.g. sodium hydride, in a suitable solvent, e.g. N,N-dimethylformamide; and (iii) removal of the N-protecting group by methods known from the art.

The compounds of formula (I) wherein $R^{12}$ represents hydrogen and —X-Q-represents —N($R^g$)—, in which $R^g$ represents —$SO_2R^a$, —$COR^d$, —$CO_2R^d$ or optionally substituted heteroaryl, may be prepared by the intramolecular cyclization of an intermediate of formula (III) wherein $R^{12}$ represents hydrogen, $X^1$ represents —$NHR^g$ and $Q^1$ represents halogen. The reaction is conveniently effected by addition of a suitable base, e.g. cesium acetate, and cuprous iodide in a suitable solvent, e.g. dimethyl sulfoxide, at an elevated temperature.

The compounds of formula (I) wherein —X-Q- represents —N($R^f$)—C(O)— may be prepared by the intramolecular cyclization of an intermediate of formula (III) wherein $X^1$ represents —$NHR^f$ and $Q^1$ is halogen, preferably chloro, in the presence of carbon monoxide and a transition metal catalyst.

The cyclization is generally effected at an elevated temperature under an elevated pressure of carbon monoxide. The reaction is conveniently carried out in a suitable solvent, e.g. 1,4-dioxane, dimethyl sulfoxide or N,N-dimethylacetamide.

Moreover, the cyclization will generally be performed in the presence of a base, e.g. an inorganic base such as sodium carbonate or potassium carbonate, or by activation using molecular sieves.

The transition metal catalyst of use in the above reaction is suitably selected from dichloro[1,3-bis(dicyclohexylphosphino)propane]palladium(II), dichloro[9,9-dimethyl-4,5-bis (diphenylphosphino)xanthene]palladium(II) and 2,2-dichloro-1,1,3,3-tetra-cyclohexyl-$1\lambda^5,3\lambda^5$-palladocyclohexane. Alternatively, a solution of palladium (II) acetate and 4,5-bis(diphenylphosphino)-9,9-dimethylxanthene (Xantphos) in a suitable solvent may be used.

In a variant procedure, the reaction may be performed using molybdenum hexacarbonyl as an alternative source of carbon monoxide.

Alternatively, the compounds of formula (I) wherein —X-Q- represents —N($R^f$)—C(O)—, in which $R^f$ represents hydrogen, may be prepared by the intramolecular cyclization of an intermediate of formula (III) wherein $X^1$ represents —$NHR^f$, in which $R^f$ represents hydrogen, and $Q^1$ is —COOH, in the presence of 4-methylmorpholine and (1-cyano-2-ethoxy-2-oxoethylidenaminooxy)dimethyl-amino-morpholino-carbenium hexafluorophosphate (COMU®). The reaction is conveniently effected in acetonitrile.

The compounds of formula (I) wherein $R^{12}$ represents hydrogen and —X-Q-represents —C(O)—N($R^f$)— may be prepared by the intramolecular cyclization of an intermediate of formula (III) wherein $R^{12}$ represents hydrogen, $X^1$ is —C(O)—NH(R') and $Q^1$ is halogen, preferably bromine, in the presence of a suitable coupling reagent, according to methods known to the person skilled in the art.

Alternatively, the compounds of formula (I) wherein $R^{12}$ represents hydrogen and —X-Q- represents —C(O)—N ($R^f$)—, in which $R^f$ represents hydrogen, may be prepared by the intramolecular cyclization of an intermediate of formula (III) wherein $R^{12}$ represents hydrogen, $X^1$ represents —$CO_2H$ and $Q^1$ represents amino. The reaction may conveniently be effected in the presence of a suitable coupling agent, e.g. 1-ethyl-3-(3-dimethylamino-propyl)carbodiimide (EDC), according to methods known to the person skilled in the art.

The compounds of formula (I) wherein $R^{12}$ represents hydrogen and —X-Q-represents —N($R^f$)—$SO_2$— may be prepared by the intramolecular cyclization of an intermediate of formula (III) wherein $R^{12}$ represents hydrogen, $X^1$ represents —$NHR^f$ and $Q^1$ represents —SH, in the presence of hydrogen peroxide and thionyl chloride, according to a method analogous to that described by K. Bahrami, M. M. Khodaei & M. Soheilizad in *J. Org. Chem.*, 2009, 74, 9287-9291.

The reaction is conveniently performed at room temperature in a suitable solvent, e.g. an apolar solvent such as acetonitrile, and in the presence of an organic base, e.g. pyridine.

In an analogous procedure, the compounds of formula (I) wherein $R^{12}$ represents hydrogen and —X-Q- represents —$SO_2$—N($R^f$)—, in which $R^f$ represents hydrogen, may be prepared from an intermediate of formula (III) wherein $R^{12}$ represents hydrogen, $X^1$ represents —SH and $Q^1$ represents amino. The reaction is conveniently effected by first protecting the amino group of $Q^1$ with a suitable N-protecting group according to methods known to the person skilled in the art; which N-protecting group can be removed once the cyclization is accomplished, again by methods known from the art.

The compounds of formula (I) wherein $R^{12}$ represents hydrogen and —X-Q-represents —$CH_2$—$CH_2$— may be prepared by a two-step procedure which comprises: (i) the intramolecular cyclization of an intermediate of formula (III) wherein $R^{12}$ represents hydrogen, $X^1$ represents —$CH_2$—$CO_2H$ and $Q^1$ represents hydrogen, typically by applying Friedel Crafts reaction conditions, e.g. by treatment with polyphosphoric acid; and (ii) reduction of the resulting compound, wherein —X-Q- represents —$CH_2$—C(O)—, according to methods known to the person skilled in the art.

The compounds of formula (I) wherein $R^{12}$ represents hydrogen and —X-Q-represents —O—$CH_2$— or —S—$CH_2$— may be prepared by the intramolecular cyclization of an intermediate of formula (III) wherein $R^{12}$ represents hydrogen, $X^1$ represents hydroxy or —SH respectively, and $Q^1$ represents —$CH_2$—Y, in which the leaving group Y is suitably halogen, preferably bromo, in the presence of a suitable base, according to methods known to the person skilled in the art.

The compounds of formula (I) wherein $R^{12}$ represents hydrogen and —X-Q-represents —$CH_2$—O— may be prepared by the intramolecular cyclization of an intermediate of formula (III) wherein $R^{12}$ represents hydrogen, $X^1$ represents —$CH_2$—OH and $Q^1$ represents halogen, preferably bromo. The reaction is conveniently effected in the presence of a suitable transition metal catalyst, e.g. a palladium(II) or copper(II) catalyst, according to methods known to the person skilled in the art.

The compounds of formula (I) wherein $R^{12}$ represents hydrogen and —X-Q-represents —$CH_2$—S— may be prepared by the intramolecular cyclization of an intermediate of formula (III) wherein $R^{12}$ represents hydrogen, $X^1$ is —$CH_2$—Y, in which the leaving group Y is suitably halogen, and $Q^1$ represents —SH, in the presence of suitable base, according to methods known to the person skilled in the art.

The compounds of formula (I) wherein $R^{12}$ represents hydrogen and —X-Q-represents —$CH_2$—N($R^g$)—, in which $R^g$ represents hydrogen, may be prepared by the intramolecular cyclization of an intermediate of formula (III) wherein $R^{12}$ represents hydrogen, $X^1$ is —$CH_2$—Y, in which the leaving group Y is suitably methylsulphonyloxy, and $Q^1$ represents amino. The reaction is conveniently effected in a three-step procedure which comprises: (i) protecting the amino group $Q^1$ with a suitable N-protecting group, e.g. tert-butoxycarbonyl, according to methods known to the person skilled in the art; (ii) intramolecular cyclization by addition of a suitable base, e.g. sodium hydride, in a suitable solvent, e.g. N,N-dimethylformamide; and (iii) removal of the N-protecting group by methods known from the art.

The compounds of formula (I) wherein $R^{12}$ represents hydrogen and —X-Q-represents —N($R^g$)—$CH_2$— or —N($R^g$)—CH($CH_3$)—, in which $R^g$ represents hydrogen, may be prepared by a two-step procedure involving: (i) the intramolecular cyclization of an intermediate of formula (III) wherein $R^{12}$ represents hydrogen, $X^1$ represents —NH($R^g$), in which $R^g$ represents hydrogen, and $Q^1$ represents formyl or acetyl respectively, by treatment with an acid, e.g. trifluoroacetic acid, in a suitable solvent, e.g. dichloromethane; and (ii) reduction of the compound thereby obtained with an appropriate reducing agent, e.g. polymer-supported cyanoborohydride or borane-dimethylsulphide complex, in a suitable solvent, e.g. tetrahydrofuran, or a mixture of tetrahydrofuran and ethanol.

The compounds of formula (I) wherein $R^{12}$ represents hydrogen and —X-Q-represents —N($R^g$)—CH($CF_3$)—, in which $R^g$ represents hydrogen, may be prepared by a variant two-step procedure involving: (i) the intramolecular cyclization of an intermediate of formula (III) wherein $R^{12}$ represents hydrogen, $X^1$ represents —NH($R^g$), in which $R^g$ represents hydrogen, and $Q^1$ represents formyl, by treatment with an acid, e.g. trifluoroacetic acid, in a suitable solvent, e.g. dichloromethane; and (ii) reacting the compound thereby obtained with (trifluoromethyl)trimethyl silane, in the presence of trifluoroacetic acid and potassium hydrogen fluoride, in a suitable solvent, e.g. N,N-dimethylformamide.

The compounds of formula (I) wherein $R^{12}$ represents hydrogen and —X-Q-represents —N=S(O)($CH_3$)— may be prepared by a two-step procedure involving: (i) the intramolecular cyclization of an intermediate of formula (III) wherein $R^{12}$ represents hydrogen, $X^1$ represents —NH($R^g$), in which $R^g$ represents hydrogen, and $Q^1$ represents —$SCH_3$, by treatment with bromine in dichloromethane; and (ii) oxidation, e.g. with 3-chloroperoxybenzoic acid.

The compounds of formula (I) wherein $R^{12}$ represents hydrogen and —X-Q-represents —O—CH($CF_3$)— may be prepared by the intramolecular cyclization of an intermediate of formula (III) wherein $R^{12}$ represents hydrogen, $X^1$ represents hydroxy and $Q^1$ represents —CH(OH)$CF_3$. The reaction is conveniently effected using (cyano-methylene)tributylphosphorane, at an elevated temperature in a suitable solvent, e.g. tetrahydrofuran.

The compounds of formula (I) wherein $R^{12}$ represents hydrogen and —X-Q-represents —O—C(=$CH_2$)— may be prepared by the intramolecular cyclization of an intermediate of formula (III) wherein $R^{12}$ represents hydrogen, $X^1$ represents halogen, e.g. bromo, and $Q^1$ represents —CO—$R^j$, in which $R^j$ represents methyl. The reaction is conveniently effected in the presence of a base, e.g. sodium hydride, in a suitable solvent, e.g. tetrahydrofuran, at low temperature.

The intermediates of formula (III) wherein E represents a group of formula (Ea) as defined above, $R^{12}$ represents hydrogen and $X^1$ represents hydroxy, may be prepared by a process which comprises the intramolecular cyclization and desilylation of an intermediate of formula (IV):

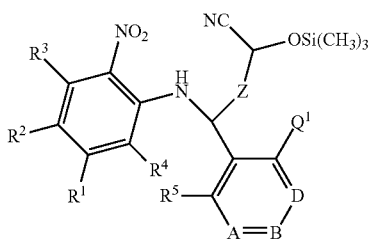

(IV)

wherein A, B, D, Z, R$^1$, R$^2$, R$^3$, R$^4$, R$^5$ and Q$^1$ are as defined above.

The reaction is suitably performed in the presence of tin(II) chloride at an elevated temperature in a polar solvent, e.g. ethanol.

The intermediates of formula (IV) as defined above may be prepared by reacting intermediate (V):

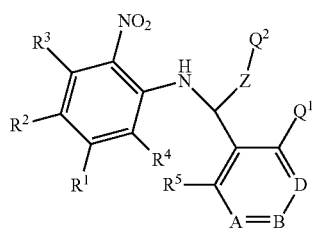

(V)

wherein Q$^2$ represents —C(O)—H, and A, B, D, Z, R$^1$, R$^2$, R$^3$, R$^4$, R$^5$ and Q$^1$ are as defined above; with zinc iodide and trimethylsilyl cyanide in the presence of a base, e.g. triethylamine.

Typically, the intermediate of formula (V) wherein Q$^2$ represents —C(O)—H may be prepared from the corresponding compound wherein Q$^2$ represents —CO$_2$R$^h$, in which R$^h$ represents C$_{1-6}$ alkyl, e.g. methyl or ethyl, by reduction with a conventional reducing agent, e.g. a metal hydride such as diisobutylaluminium hydride (DIBAL-H).

The intermediates of formula (V) wherein Q$^2$ represents —CO$_2$R$^h$ may be obtained by reacting an intermediate of formula (VI) with an intermediate of formula (VII):

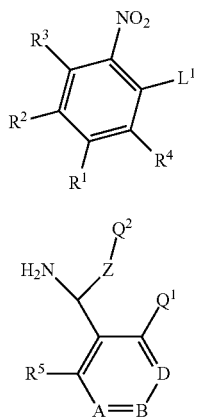

(VI)

(VII)

wherein A, B, D, Z, R$^1$, R$^2$, R$^3$, R$^4$, R$^5$, Q$^1$ and Q$^2$ are as defined above, and L$^1$ represents a suitable leaving group.

The leaving group L$^1$ is suitably a halogen atom, for example fluorine or bromine.

The reaction is conveniently performed in the presence of a base, e.g. an inorganic base such as potassium carbonate, in a suitable solvent, e.g. an apolar solvent such as acetonitrile, at an elevated temperature.

The intermediates of formula (VII) may be prepared by a multi-step process starting from an intermediate of formula (VIII):

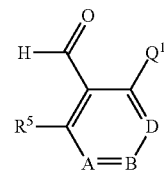

(VIII)

wherein A, B, D, R$^5$ and Q$^1$ are as defined above; which process comprises the following steps:

(i) reaction of intermediate (VIII) with (S)-tert-butylsulfinamide in the presence of K$_3$PO$_4$/K$_2$HPO$_4$ in a suitable solvent, e.g. tetrahydrofuran;

(ii) reacting the compound obtained from step (i) with a compound of formula L$^2$-Z-Q$^2$, wherein Z and Q$^2$ are as defined above and L$^2$ is a suitable leaving group, e.g. halogen, such as bromine, and activated zinc metal dust prepared according to conditions described by H. Hilpert et al. in *Journal of Medicinal Chemistry*, 2013, 56(10), 3980-3995, typically in the presence of a transition metal salt, e.g. copper(I) chloride, optionally at an elevated temperature; and (iii) reaction with a strong mineral acid, e.g. hydrochloric acid.

The intermediates of formula (VIII) wherein R$^5$ represents halogen, e.g. chloro, may be transformed into the corresponding intermediate of formula (VIII) wherein R$^5$ represents difluoromethoxy by a two-step process which comprises: (i) reaction with potassium hydroxide in water at low temperature; and (ii) reaction with diethyl (bromodifluoromethyl)phosphonate at low temperature.

The intermediates of formula (III) wherein E represents a group of formula (Ea) as defined above, R$^{12}$ represents hydrogen and —X$^1$ represents —NH(R$^g$), in which R$^g$ represents hydrogen, may be prepared by a process which comprises the reduction, intramolecular cyclization and desulfination of an intermediate of formula (IVa):

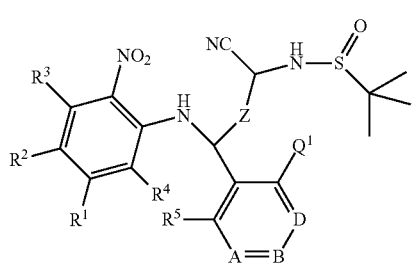

(IVa)

wherein A, B, D, Z, R$^1$, R$^2$, R$^3$, R$^4$, R$^5$ and Q$^1$ are as defined above.

The reaction is conveniently performed in the presence of tin(II) chloride, with the addition of a strong acid, e.g. hydrochloric acid, at an elevated temperature in a suitable solvent, e.g. ethanol.

Alternatively, the transformation may be effected by a procedure involving: (i) reduction using hydrogen gas under pressure, in the presence of zinc bromide and a hydrogenation catalyst, e.g. platinum on charcoal; and (ii) addition of a strong acid, e.g. hydrochloric acid, at an elevated temperature in a suitable solvent, e.g. ethanol.

The intermediates of formula (IVa) may be prepared by a multi-step process starting from an intermediate of formula (Va):

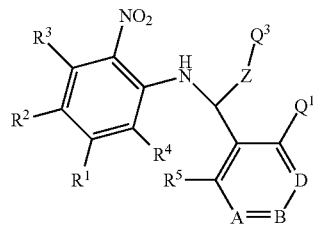
(Va)

wherein A, B, D, Z, $R^1$, $R^2$, $R^3$, $R^4$, $R^5$ and $Q^1$ are as defined above, and $Q^3$ represents —CH=CH$_2$; which process comprises the following steps:

(i) reacting intermediate (Va) with sodium periodate, in the presence of potassium dioxido(dioxo)osmium hydrate and a base, e.g. N,N-dimethylpyridinyl-4-amine or 2,6-dimethylpyridine, followed by addition of sodium thiosulfate, to afford the corresponding intermediate of formula (Va) wherein $Q^3$ represents —CH=O;

(ii) reacting the compound thereby obtained with (R)-2-methylpropane-2-sulfinamide in the presence of a transition metal catalyst, e.g. titanium(IV) isopropoxide, in a suitable solvent, e.g. dichloromethane, to afford the corresponding intermediate of formula (Va) wherein $Q^3$ represents —CH=N—S(=O)—C(CH$_3$)$_3$; and (iii) reacting the compound thereby obtained with sodium cyanide in the presence of scandium triflate in a suitable solvent, e.g. tetrahydrofuran.

The intermediates of formula (Va) as defined above may be prepared by reacting an intermediate of formula (VI) as defined above with an intermediate of formula (VIIa):

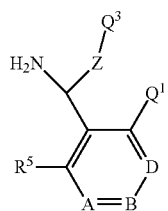
(VIIa)

wherein A, B, D, Z, $R^5$, $Q^1$ and $Q^3$ are as defined above; under conditions analogous to those described above for the preparation of the intermediates of formula (V).

The intermediates of formula (VIIa) may be prepared from the intermediates of formula (VIII) by a process analogous to that described above for the preparation of the intermediates of formula (VII).

The intermediates of formula (III) wherein E represents a group of formula (Eb) or (Ec) as defined above, $R^{12}$ represents hydrogen and $X^1$ represents hydroxy may be prepared from an intermediate of formula (IIIA):

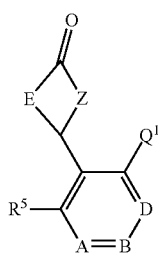
(IIIA)

wherein A, B, D, Z, E, $R^5$ and $Q^1$ are as defined above; by reduction of the carbonyl moiety according to methods known to the person skilled in the art.

The intermediates of formula (III) wherein E represents a group of formula (Eb) or (Ec) as defined above, $R^{12}$ represents methyl and $X^1$ represents —NH(R'), in which $R^f$ represents hydrogen, may be prepared from an intermediate of formula (IIIA) utilising the following sequence of steps:

(i) reacting an intermediate of formula (IIIA) with 2-methylpropane-2-sulfinamide in the presence of titanium (IV) isopropoxide in a solvent, e.g. tetrahydrofuran;

(ii) adding a solution of methylmagnesium bromide, at low temperature, in a suitable solvent, e.g. dichloromethane; and (iii) removing the tert-butylsulphinyl moiety by treatment with a strong acid, e.g. hydrochloric acid, in a suitable solvent, e.g. 1,4-dioxane.

The intermediates of formula (IIIA) may be prepared by the intramolecular cyclization of an intermediate of formula (IX):

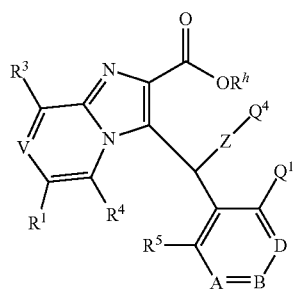
(IX)

wherein V is N or C—$R^2$, $Q^4$ is an electron-withdrawing group, preferably an ester moiety, and A, B, D, Z, $R^1$, $R^2$, $R^3$, $R^4$, $R^5$, $R^h$ and $Q^1$ are as defined above; in the presence of a base.

The reaction may conveniently be effected in a suitable solvent at an elevated temperature.

The intermediates of formula (IX) may be prepared by reacting an intermediate of formula (X) with an intermediate of formula (XI):

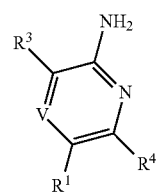
(X)

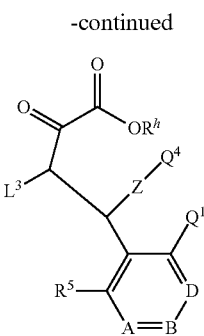

(XI)

wherein A, B, D, V, Z, $R^1$, $R^3$, $R^4$, $R^5$, $R^h$, $Q^1$ and $Q^4$ are as defined above, and $L^3$ represents a suitable leaving group.

The leaving group $L^3$ is typically a halogen atom, e.g. bromo.

The reaction is conveniently effected at an elevated temperature in a suitable solvent, e.g. a $C_{1-4}$ alkanol such as ethanol, or an ether such as 1,4-dioxane or 1,2-dimethoxyethane, typically in the presence of magnesium sulphate.

Alternatively, the intermediates of formula (IX) wherein Z is methylene and $Q^4$ is —$CO_2H$ may be prepared by reacting an intermediate of formula (VIII) as defined above with an intermediate of formula (XII):

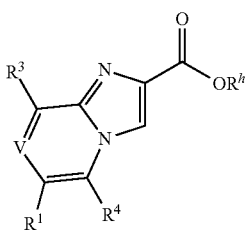

(XII)

wherein V, $R^1$, $R^3$, $R^4$ and $R^h$ are as defined above; in the presence of Meldrum's acid, according to a method analogous to that described in WO 2009/156091; or by M. Kerr et al. in *J. Org. Chem.*, 2013, 78, 10534.

The reaction is conveniently effected at an elevated temperature in a suitable solvent, e.g. acetonitrile, in the presence of proline and magnesium sulphate.

Where they are not commercially available, the starting materials of formula (VI), (VIII), (X), (XI) and (XII) may be prepared by methods analogous to those described in the accompanying Examples, or by standard methods well known from the art.

The intermediates of formula (III) wherein $X^1$ represents amino may be prepared from a corresponding intermediate of formula (III) wherein $X^1$ is hydroxy by a stepwise procedure which comprises: (i) treatment with diphenyl phosphoryl azide and 1,8-diaza-bicyclo[5.4.0]undec-7-ene in a suitable solvent, e.g. tetrahydrofuran; and (ii) subsequent aza-Wittig reaction using triphenylphosphine in a suitable solvent, e.g. a mixture of water and toluene.

The intermediates of formula (III) wherein E represents a group of formula (Eb) or (Ec) as defined above, $R^{12}$ is hydrogen, and $X^1$ represents amino, may be prepared from an intermediate of formula (IIIA) by reaction with a $C_{1-6}$ alkylsulfinamide, e.g. (R)-2-methyl-propane-2-sulfinamide, in the presence of a transition metal catalyst, e.g. titanium (IV) ethoxide, in a suitable solvent, e.g. dichloromethane, followed by reduction with a suitable reducing agent, e.g. sodium borohydride, in a suitable solvent, e.g. tetrahydrofuran, and subsequent removal of the sulfinyl moiety, typically by treatment with a mineral acid, e.g. hydrochloric acid.

The intermediates of formula (III) wherein $X^1$ represents Y or —$CH_2$—Y, in which Y represents a leaving group, e.g. halogen or ($C_{1-6}$)alkylsulphonyloxy, may be prepared from an intermediate of formula (III) wherein $X^1$ is hydroxy or —$CH_2OH$ respectively according to standard methods known to the person skilled in the art.

The intermediates of formula (III) wherein $X^1$ represents —SH may be prepared from an intermediate of formula (III) wherein $X^1$ is hydroxy or a leaving group Y according to standard methods known to the person skilled in the art.

The intermediates of formula (III) wherein $X^1$ represents —$CO_2H$ may be prepared by hydrolysis of a corresponding intermediate of formula (III) wherein $X^1$ represents cyano according to standard methods known to the person skilled in the art.

The intermediates of formula (III) wherein $X^1$ represents cyano may be prepared by nucleophilic substitution of an intermediate of formula (III) wherein $X^1$ represents a leaving group Y, in which Y represents ($C_{1-6}$)alkylsulphonyloxy, according to standard methods known to the person skilled in the art.

The intermediates of formula (III) wherein $X^1$ represents —$CH_2OH$ may be prepared by reduction of the corresponding intermediate of formula (III) wherein $X^1$ represents —$CO_2H$ by treatment with a suitable reducing reagent, e.g. $BH_3$.

The intermediates of formula (III) wherein $X^1$ represents —$NH(R^g)$, in which $R^g$ represents —$COR^d$, may be prepared by reacting a compound of formula (III) wherein $X^1$ represents —$NH_2$ with a compound of formula $R^d$—$CO_2H$ in the presence of a base, e.g. N,N-diisopropylethylamine, and a coupling agent, e.g. N-[(dimethylamino)-1H-1,2,3-triazolo-[4,5-b]pyridin-1-ylmethylene]-N-ethylethanaminium hexafluorophosphate N-oxide (HATU), in a suitable solvent, e.g. N,N-dimethylformamide.

The intermediates of formula (III) wherein $Q^1$ represents formyl may be prepared from an intermediate of formula (III) wherein $Q^1$ represents halogen, e.g. bromine, by a stepwise process involving: (i) reaction with potassium vinylfluoroborate in the presence of a base and a transition metal catalyst; and (ii) reaction with sodium periodate and osmium tetraoxide in the presence of a suitable solvent, e.g. a cyclic ether such as 1,4-dioxane. In step (i), suitable bases include inorganic bases such as cesium carbonate; and suitable transition metal catalysts include 1,1'-bis(diphenylphosphino)ferrocene-palladium(II) dichloride-dichloromethane complex.

The intermediates of formula (III) wherein $Q^1$ represents acetyl may be prepared from an intermediate of formula (III) wherein $Q^1$ represents halogen, e.g. bromine, by a stepwise process involving: (i) reaction with tributyl(1-ethoxyvinyl)tin in the presence of bis(triphenylphosphine)palladium(II) dichloride in a suitable solvent, e.g. toluene, at an elevated temperature; and (ii) reaction with an acid, e.g. p-toluenesulphonic acid.

The intermediates of formula (III) wherein $Q^1$ represents —$S(CH_2)_2CO_2CH_2CH(CH_2CH_3)[(CH_2)_3CH_3]$ may be prepared from an intermediate of formula (III) wherein $Q^1$ represents halogen, e.g. bromine, by reaction with 3-mercapto-propionic acid 2-ethyl ester in the presence of a suitable transition metal catalyst, e.g. tris(benzylideneacetone)dipalladium(0) and 4,5-bis(diphenylphosphino)-9,9-dimethyl-xanthene, in a suitable solvent, e.g. 1,4-dioxane, at an elevated temperature.

Similarly, the intermediates of formula (III) wherein $Q^1$ represents —SCH$_2$CO$_2$CH$_2$CH$_3$ may be prepared from intermediates of formula (III) wherein $Q^1$ represents halogen, e.g. bromine, by reaction with ethyl thioglycolate in the presence of a suitable transition metal catalyst, e.g. tris(benzylideneacetone)dipalladium(0) and 4,5-bis(diphenylphosphino)-9,9-dimethylxanthene, in a suitable solvent, e.g. 1,4-dioxane, at an elevated temperature.

The intermediates of formula (III) wherein $Q^1$ represents —SCH$_3$ may be prepared from an intermediate of formula (III) wherein $Q^1$ represents halogen, e.g. bromine, by a process which involves treatment with sodium thiomethoxide in a suitable solvent, e.g. dimethyl sulphoxide, at an elevated temperature.

The intermediates of formula (III) wherein $Q^1$ represents —CH(OH)CF$_3$ may be prepared from an intermediate of formula (III) wherein $Q^1$ represents —C(O)H by reaction with tetrabutylammonium fluoride, followed by (trifluoromethyl)trimethylsilane, in a suitable solvent, e.g. tetrahydrofuran.

It will be understood that any compound of formula (I) initially obtained from any of the above processes may, where appropriate, subsequently be elaborated into a further compound of formula (I) by techniques known from the art.

By way of example, a compound of formula (I) wherein —X-Q- represents —O—CH$_2$— may be prepared by reduction of a corresponding compound of formula (I) wherein —X-Q-represents —O—C(O)— according to the method described in Sakai et al., *J. Org. Chem.*, 2007, 72, 5920-5922.

A compound of formula (I) wherein —X-Q- represents —N(R$^g$)—CH$_2$— may be prepared in a similar fashion from a corresponding compound of formula (I) wherein —X-Q- represents —N(R$^f$)—CO—; or under any other lactam reduction conditions known to the person skilled in the art.

A compound of formula (I) wherein —X-Q- represents —S—, —CH$_2$—S— or —S—CH$_2$— may be transformed into the corresponding compound of formula (I) wherein —X-Q-represents —SO—, —SO$_2$—, —CH$_2$—SO—, —CH$_2$—SO$_2$—, —SO—CH$_2$— or —SO$_2$—CH$_2$—, by performing an oxidation reaction according to methods known to the person skilled in the art.

A compound of formula (I) wherein —X-Q- represents —SO—, —CH$_2$—SO— or —SO—CH$_2$— may be transformed into the corresponding compound of formula (I) wherein —X-Q-represents —S(O)(NH)—, —CH$_2$—S(O)(NH)— or —S(O)(NH)—CH$_2$— respectively by a method analogous to that described in Okamura, H. et al., *Organic Letters*, 2004, 6(8), 1305-1307.

A compound of formula (I) wherein —X-Q- represents —S— may be transformed into the corresponding compound of formula (I) wherein —X-Q- represents —S(=N—CN)— by reaction with iodobenzene diacetate in the presence of cyanamide. The reaction is conveniently effected in acetonitrile.

A compound of formula (I) wherein —X-Q- represents —N(R$^f$)—C(O)— may be converted into the corresponding compound of formula (I) wherein —X-Q- represents —N(R$^f$)—C(S)— by treatment with Lawesson's reagent according to methods known to the person skilled in the art.

A compound of formula (I) wherein —X-Q- represents —NH— may be transformed into the corresponding compound of formula (I) wherein —X-Q- represents —N(R$^g$)—, in which R$^g$ represents —COR$^d$, by reaction with a compound of formula R$^d$—COCl in a suitable solvent, e.g. dichloromethane.

A compound of formula (I) or (III) wherein R$^f$ or R$^g$ represents hydrogen may be transformed into the corresponding compound of formula (I) or (III) wherein R$^f$ or R$^g$ represents optionally substituted C$_{1-6}$ alkyl, or its deuterated equivalent, by reaction with the appropriate optionally substituted C$_{1-6}$ alkyl halide or deuterated equivalent thereof, e.g. a C$_{1-6}$ alkyl iodide or its deuterated equivalent, in the presence of a base, e.g. cesium carbonate or potassium bis(trimethylsilyl)amide (KHMDS), in a suitable solvent, e.g. N,N-dimethylformamide or tetrahydrofuran.

A compound of formula (I) or (III) wherein R$^f$ or R$^g$ represents hydrogen may be transformed into the corresponding compound of formula (I) or (III) wherein R$^f$ or R$^g$ represents acetyl by reaction with acetic anhydride in the presence of base, e.g. pyridine, in a suitable solvent, e.g. dichloromethane.

A compound of formula (I) or (III) wherein R$^f$ or R$^g$ represents hydrogen may be transformed into the corresponding compound of formula (I) or (III) wherein R$^f$ or R$^g$ represents methyl by reaction with formaldehyde in a suitable solvent, e.g. 2,2,2-trifluoroethanol, followed by reaction with a suitable reducing agent, e.g. sodium borohydride.

A compound of formula (I) or (III) wherein R$^f$ or R$^g$ represents hydrogen may be transformed into the corresponding compound of formula (I) or (III) wherein R$^f$ or R$^g$ represents C$_{1-6}$ alkylsulphonyl by treatment with the appropriate C$_{1-6}$ alkylsulphonyl halide, e.g. methanesulphonyl chloride, in the presence of a suitable base, e.g. N,N-diisopropylethylamine or triethylamine, in a suitable solvent, e.g. dichloromethane.

A compound of formula (I) or (III) which contains a hydroxy group may be alkylated by treatment with the appropriate alkyl halide in the presence of a base, e.g. sodium hydride, or silver oxide.

A compound of formula (I) or (III) which contains hydroxy may be converted into the corresponding fluoro-substituted compound by treatment with diethylaminosulfur trifluoride (DAST) or bis(2-methoxyethyl)aminosulfur trifluoride (BAST). A compound of formula (I) which contains hydroxy may be converted into the corresponding difluoro-substituted compound via a two-step procedure which comprises: (i) treatment with an oxidising agent, e.g. manganese dioxide; and (ii) treatment of the carbonyl-containing compound thereby obtained with DAST.

A compound of formula (I) or (III) which contains an N—H moiety may be alkylated by treatment with the appropriate alkyl halide, typically at an elevated temperature in an organic solvent such as acetonitrile; or at ambient temperature in the presence of a base, e.g. potassium hydroxide, in a suitable solvent, e.g. tetrahydrofuran, in the presence of tetrabutylammonium bromide; or at an elevated temperature in the presence of a base, e.g. sodium hydride, with or without tetrabutylammonium iodate, in a suitable solvent, e.g. tetrahydrofuran; or at elevated temperature in the presence of an alkali metal carbonate such as potassium carbonate or cesium carbonate, in a suitable solvent, e.g. a dipolar aprotic solvent such as N,N-dimethylformamide. A compound of formula (I) which contains an N—H moiety may be methylated by treatment with formaldehyde in the presence of a reducing agent, e.g. sodium triacetoxyborohydride.

A compound of formula (I) or (III) which contains an N—H moiety may be acylated by treatment with the appropriate acid chloride, e.g. acetyl chloride, or with the appropriate carboxylic acid anhydride, e.g. acetic anhydride, typically at ambient temperature in the presence of a base, e.g. an organic base such as triethylamine.

A compound of formula (I) or (III) which contains an N—H moiety may be converted into the corresponding compound wherein the nitrogen atom is substituted by $C_{1-6}$ alkylsulphonyl, e.g. methylsulphonyl, by treatment with the appropriate $C_{1-6}$ alkylsulphonyl chloride, e.g. methanesulphonyl chloride, or with the appropriate $C_{1-6}$ alkylsulphonic acid anhydride, e.g. methanesulphonic anhydride, typically at ambient temperature in the presence of a base, e.g. an organic base such as triethylamine or N,N-diisopropylethylamine.

A compound of formula (I) or (III) which contains an N—H moiety may be converted into the corresponding compound wherein the nitrogen atom is substituted by $C_{1-6}$ alkoxycarbonyl, e.g. methoxycarbonyl, by treatment with the corresponding $C_{1-6}$ alkoxycarbonyl halide in the presence of a base, e.g. potassium carbonate, in a suitable solvent, e.g. N,N-dimethylformamide.

A compound of formula (I) or (III) substituted by amino (—$NH_2$) may be converted into the corresponding compound substituted by $C_{1-6}$ alkylsulphonylamino, e.g. methylsulphonylamino, or bis[($C_{1-6}$)alkylsulphonyl]amino, e.g. bis(methylsulphonyl)amino, by treatment with the appropriate $C_{1-6}$ alkylsulphonyl halide, e.g. a $C_{1-6}$ alkylsulphonyl chloride such as methanesulphonyl chloride, in the presence of a suitable base, e.g. N,N-diisopropylethylamine, in a suitable solvent, e.g. dichloromethane.

Thus, a compound of formula (I) or (III) substituted by amino may be transformed into the corresponding compound substituted by —$NHSO_2R^e$ by treatment with a compound of formula $R^e$—$SO_2Cl$.

Similarly, a compound of formula (I) substituted by hydroxy (—OH) may be converted into the corresponding compound substituted by $C_{1-6}$ alkylsulphonyloxy, e.g. methylsulphonyloxy, by treatment with the appropriate $C_{1-6}$ alkylsulphonyl halide, e.g. a $C_{1-6}$ alkylsulphonyl chloride such as methanesulphonyl chloride.

A compound of formula (I) or (III) containing the moiety —S— may be converted into the corresponding compound containing the moiety —S(O)— by treatment with 3-chloroperoxybenzoic acid. Likewise, a compound of formula (I) or (III) containing the moiety —S(O)— may be converted into the corresponding compound containing the moiety —$S(O)_2$— by treatment with 3-chloroperoxybenzoic acid. Alternatively, a compound of formula (I) containing the moiety —S— may be converted into the corresponding compound containing the moiety —$S(O)_2$— by treatment with Oxone® (potassium peroxymonosulfate).

A compound of formula (I) or (III) containing an aromatic nitrogen atom may be converted into the corresponding N-oxide derivative by treatment with 3-chloroperoxy-benzoic acid.

A compound of formula (I) or (III) which contains a carbonyl (C═O) moiety may be converted into the corresponding compound containing a CH(OH) functionality by treatment with a suitable borohydride reagent, e.g. lithium tri-sec-butyl borohydride or sodium borohydride, in a suitable solvent e.g. tetrahydrofuran.

A compound of formula (I) or (III) wherein $R^1$ represents halogen, e.g. bromo, may be converted into the corresponding compound wherein $R^1$ represents an optionally substituted aryl or heteroaryl moiety by treatment with the appropriately substituted aryl or heteroaryl boronic acid or a cyclic ester thereof formed with an organic diol, e.g. pinacol, 1,3-propanediol or neopentyl glycol. The reaction is typically effected at an elevated temperature in the presence of a transition metal catalyst, e.g. [1,1'-bis(diphenyl-phosphino)ferrocene]dichloropalladium(II), tetrakis(triphenylphosphine)palladium(0), bis[3-(diphenylphosphinyl)cyclopenta-2,4-dien-1-yl]iron-dichloropalladium-dichloromethane complex, or tris(dibenzylideneacetone)dipalladium(0) and tricyclohexyl-phosphonium tetrafluoroborate, and a base, e.g. an inorganic base such as sodium carbonate, potassium carbonate or cesium carbonate, or potassium phosphate, in a suitable solvent, e.g. 1,4-dioxane or a mixture of 1,4-dioxane and water.

A compound of formula (I) wherein $R^1$ represents 2-oxo-(1H)-pyridinyl may be obtained by treatment of the corresponding compound wherein $R^1$ represents 2-methoxy-pyridinyl with pyridine hydrochloride at an elevated temperature.

A compound of formula (I) or (III) wherein $R^1$ represents an ester moiety may be obtained by reacting the corresponding compound wherein $R^1$ is halogen, e.g. chloro, with a base, e.g. sodium carbonate, and the appropriate alcohol in the presence of carbon monoxide and a transition metal catalyst, typically [1,3-bis(dicyclohexylphosphino)-propane]palladium(II).

A compound of formula (I) or (III) wherein $R^1$ represents cyano may be obtained by reacting the corresponding compound of formula (I) or (III) wherein $R^1$ is halogen, e.g. chloro, with zinc cyanide in the presence of a transition metal catalyst, e.g. tetrakis-(triphenylphosphine)palladium (0), in a suitable solvent, e.g. N,N-dimethylformamide.

In general, a compound of formula (I) containing a —C═C— functionality may be converted into the corresponding compound containing a —CH—CH— functionality by catalytic hydrogenation, typically by treatment with a hydrogenation catalyst, e.g. palladium on charcoal, under an atmosphere of hydrogen gas, optionally in the presence of a base, e.g. an alkali metal hydroxide such as sodium hydroxide.

A compound of formula (I) containing an ester moiety, e.g. a $C_{2-6}$ alkoxycarbonyl group such as methoxycarbonyl or ethoxycarbonyl, may be converted into the corresponding compound containing a carboxy (—$CO_2H$) moiety by treatment with an acid, e.g. a mineral acid such as hydrochloric acid.

A compound of formula (I) containing an ester moiety, e.g. a $C_{2-6}$ alkoxycarbonyl group such as methoxycarbonyl or ethoxycarbonyl, may alternatively be converted into the corresponding compound containing a carboxy (—$CO_2H$) moiety by treatment with a base, e.g. an alkali metal hydroxide selected from lithium hydroxide, sodium hydroxide and potassium hydroxide; or an organic base such as sodium methoxide or sodium ethoxide.

A compound of formula (I) containing a carboxy (—$CO_2H$) moiety may be converted into the corresponding compound containing an amide moiety by treatment with the appropriate amine in the presence of a condensing agent such as 1-ethyl-3-(3-dimethyl-aminopropyl)carbodiimide.

A compound of formula (I) containing a carbonyl (C═O) moiety may be converted into the corresponding compound containing a —C($CH_3$)(OH)— moiety by treatment with methylmagnesium bromide. Similarly, a compound of formula (I) containing a carbonyl (C═O) moiety may be converted into the corresponding compound containing a —C($CF_3$)(OH)— moiety by treatment with (trifluoromethyl)trimethylsilane and cesium fluoride. A compound of formula (I) containing a carbonyl (C═O) moiety may be converted into the corresponding compound containing a —C(CH$_2$NO$_2$)(OH)— moiety by treatment with nitromethane.

A compound of formula (I) containing a hydroxymethyl moiety may be converted into the corresponding compound containing a formyl (—CHO) moiety by treatment with an oxidising agent such as Dess-Martin periodinane. A compound of formula (I) containing a hydroxymethyl moiety may be converted into the corresponding compound containing a carboxy moiety by treatment with an oxidising agent such as tetrapropylammonium perruthenate.

A compound of formula (I) containing an aryl or heteroaryl moiety may be transformed into the corresponding compound, wherein a hydrogen atom in the aryl or heteroaryl moiety has been replaced by chloro or bromo, by reaction with N-chloro-succinimide or N-bromosuccinimide respectively in a suitable solvent, e.g. N,N-dimethyl-formamide, according to methods known to the person skilled in the art.

A compound of formula (I) containing an aryl moiety bearing a difluoromethoxy group may be transformed into the corresponding compound, wherein the difluoromethoxy group in the aryl moiety has been replaced by a hydroxy group, by reaction with sodium bis(trimethylsilyl)amide (NaHMDS) in a suitable solvent, e.g. tetrahydrofuran.

A compound of formula (I) containing an aryl or heteroaryl moiety may be transformed into the corresponding compound, wherein a hydrogen atom in the aryl or heteroaryl moiety has been replaced by trifluoromethyl, by a stepwise procedure which comprises: (i) treatment with trifluoroacetic acid in a suitable solvent, e.g. acetonitrile; and (ii) addition of trifluoromethanesulphonyl chloride, followed by [4,4'-bis(tert-butyl)-2,2'-bipyridine]bis {3,5-difluoro-2-[5-(trifluoromethyl)pyridin-2-yl]phenyl}iridium (III) hexafluorophosphate, according to conditions analogous to those described by McMillan et al. in *Nature*, 2011, 480, 224.

A compound of formula (I) substituted by phosphate (C$_{1-6}$)alkyl may be prepared from the corresponding compound substituted by hydroxy(C$_{1-6}$)alkyl by a stepwise procedure which comprises: (i) treatment with dibenzyl N,N-diisopropylphosphoramidite in a suitable solvent, e.g. dichloromethane, followed by treatment with hydrogen peroxide; and (ii) hydrogenolysis, e.g. using hydrogen gas under pressure, in the presence of a suitable catalyst, e.g. palladium on charcoal, according to a method analogous to those described by S. P. Green et al. in *Organic Process Research & Development*, 2002, 6, 109-112. A compound of formula (I) substituted by a salt of phosphate(C$_{1-6}$)alkyl may be prepared by performing step (ii) in the presence of a suitable alkali metal base or alkaline earth metal base. Similarly, an isolated compound of formula (I) substituted by phosphate-(C$_{1-6}$)alkyl may be converted into the corresponding compound substituted by a salt of phosphate(C$_{1-6}$)alkyl by treatment with an appropriate base, e.g. an alkali metal base, or an alkaline earth metal base, or ammonia, or an organic amine, in a suitable solvent according to methods known to the person skilled in the art. Suitable alkali metal bases include sodium hydroxide and potassium hydroxide. Suitable alkaline earth metal bases include calcium hydroxide. Suitable organic amines include triethylamine.

A compound of formula (I) substituted by (C$_{1-6}$)alkylphosphate(C$_{1-6}$)alkyl may be prepared from the corresponding compound substituted by hydroxy(C$_{1-6}$)alkyl by a stepwise procedure which comprises: (i) reacting cyanoethyl phosphoramidite with the appropriate C$_{1-6}$ alkanol in the presence of a base, e.g. N,N-diisopropylethylamine, in a suitable solvent, e.g. dichloromethane; (ii) addition of the relevant compound of formula (I) substituted by hydroxy (C$_{1-6}$)alkyl in a suitable solvent, e.g. dichloromethane; and (iii) oxidation and subsequent treatment with a suitable base, according to a method analogous to those described by Nam, N—H. et al. in *Bio-org. Med. Chem.*, 2004, 12, 6255; and in WO 2012/177707.

A compound of formula (I) substituted by sulphate(C$_{1-6}$) alkyl may be prepared by treatment of the corresponding compound substituted by hydroxy(C$_{1-6}$)alkyl with pyridine: sulphur trioxide complex, according to a method analogous to that described by E. Lacko et al. in *Current Medicinal Chemistry*, 2012, 19, 4699; or by treatment with chlorosulphonic acid in the presence of triethylamine, according to a method analogous to that described in WO 2004/087720.

A compound of formula (I) substituted by phosphatemethoxy(C$_{1-6}$)alkyl may be prepared by reacting the corresponding compound substituted by hydroxy(C$_{1-6}$)alkyl with a suitable base, e.g. sodium hydride, in a suitable solvent, e.g. 1,2-dimethoxyethane, followed by addition of chloromethyl di-tert-butylphosphate, with subsequent dealkylation at an elevated temperature, according to a method analogous to that described in WO 2012/135082.

Where a mixture of products is obtained from any of the processes described above for the preparation of compounds according to the invention, the desired product can be separated therefrom at an appropriate stage by conventional methods such as preparative HPLC; or column chromatography utilising, for example, silica and/or alumina in conjunction with an appropriate solvent system.

Where the above-described processes for the preparation of the compounds according to the invention give rise to mixtures of stereoisomers, these isomers may be separated by conventional techniques. In particular, where it is desired to obtain a particular enantiomer of a compound of formula (I) this may be produced from a corresponding mixture of enantiomers using any suitable conventional procedure for resolving enantiomers. Thus, for example, diastereomeric derivatives, e.g. salts, may be produced by reaction of a mixture of enantiomers of formula (I), e.g. a racemate, and an appropriate chiral compound, e.g. a chiral base. The diastereomers may then be separated by any convenient means, for example by crystallisation, and the desired enantiomer recovered, e.g. by treatment with an acid in the instance where the diastereomer is a salt. In another resolution process a racemate of formula (I) may be separated using chiral HPLC. Moreover, if desired, a particular enantiomer may be obtained by using an appropriate chiral intermediate in one of the processes described above. Alternatively, a particular enantiomer may be obtained by performing an enantiomer-specific enzymatic biotransformation, e.g. an ester hydrolysis using an esterase, and then purifying only the enantiomerically pure hydrolysed acid from the unreacted ester antipode. Chromatography, recrystallisation and other conventional separation procedures may also be used with intermediates or final products where it is desired to obtain a particular geometric isomer of the invention. Alternatively the non-desired enantiomer may be racemized into the desired enantiomer, in the presence of an acid or a base, according to methods known to the person skilled in the art, or according to methods described in the accompanying Examples.

During any of the above synthetic sequences it may be necessary and/or desirable to protect sensitive or reactive groups on any of the molecules concerned. This may be achieved by means of conventional protecting groups, such as those described in *Protective Groups in Organic Chem-*

*istry*, ed. J. F. W. McOmie, Plenum Press, 1973; and T. W. Greene & P. G. M. Wuts, *Protective Groups in Organic Synthesis*, John Wiley & Sons, $3^{rd}$ edition, 1999. The protecting groups may be removed at any convenient subsequent stage utilising methods known from the art.

Compounds in accordance with the present invention potently neutralise the activity of TNFα in a commercially available HEK-293 derived reporter cell line known as HEK-Blue™ CD40L. This is a stable HEK-293 transfected cell line expressing SEAP (secreted embryonic alkaline phosphatase) under the control of the IFNβ minimal promoter fused to five NF-κB binding sites. Secretion of SEAP by these cells is stimulated in a concentration-dependent manner by TNFα. When tested in the HEK-293 bioassay, also referred to herein as the reporter gene assay, compounds of the present invention exhibit an $IC_{50}$ value of 50 μM or less, generally of 20 μM or less, usually of 5 μM or less, typically of 1 μM or less, suitably of 500 nM or less, ideally of 100 nM or less, and preferably of 25 nM or less (the skilled person will appreciate that a lower $IC_{50}$ figure denotes a more active compound).

Certain compounds in accordance with the present invention potently inhibit the binding of a fluorescence conjugate to TNFα when tested in the fluorescence polarisation assay described herein. Indeed, when tested in that assay, compounds of the present invention exhibit an $IC_{50}$ value of 50 μM or less, generally of 20 μM or less, usually of 5 M or less, typically of 1 μM or less, suitably of 500 nM or less, ideally of 100 nM or less, and preferably of 25 nM or less (as before, the skilled person will appreciate that a lower $IC_{50}$ figure denotes a more active compound).

The compounds of the Examples have been tested in one or both of the assays described below.

Fluorescence Polarisation Assay
Preparation of Compound (A)
1-(2,5-Dimethylbenzyl)-6-[4-(piperazin- 1-ylmethyl)phenyl]-2-(pyridin-4-yl-methyl)-1H-benzimidazole—hereinafter referred to as "Compound (A)"—can be prepared by the procedure described in Example 499 of WO 2013/186229; or by a procedure analogous thereto.

Preparation of Fluorescence Conjugate

Compound (A) (27.02 mg, 0.0538 mmol) was dissolved in DMSO (2 mL). 5 (–6) Carboxy-fluorescein succinimyl ester (24.16 mg, 0.0510 mmol) (Invitrogen catalogue number: C1311) was dissolved in DMSO (1 mL) to give a bright yellow solution. The two solutions were mixed at room temperature, the mixture turning red in colour. The mixture was stirred at room temperature. Shortly after mixing a 20 μL aliquot was removed and diluted in a 80:20 mixture of AcOH:H$_2$O for LC-MS analysis on the 1200RR-6140 LC-MS system. The chromatogram showed two closely eluting peaks at retention times of 1.42 and 1.50 minutes, both with mass $(M+H)^+=860.8$ amu, corresponding to the two products formed with the 5- and 6-substituted carboxyfluorescein group. A further peak at retention time 2.21 minutes had a mass of $(M+H)^+=502.8$ amu, corresponding to Compound (A). No peak was observed for unreacted 5(-6) carboxyfluorescein succinimyl ester. The peak areas were 22.0%, 39.6% and 31.4% for the three signals, indicating a 61.6% conversion to the two isomers of the desired fluorescence conjugate at that time-point. Further 20 μL aliquots were extracted after several hours and then after overnight stirring, diluted as before and subjected to LC-MS analysis. The percentage conversion was determined as 79.8% and 88.6% respectively at these time-points. The mixture was purified on a UV-directed preparative HPLC system. The pooled purified fractions were freeze-dried to remove excess solvent. After freeze-drying, an orange solid (23.3 mg) was recovered, equivalent to 0.027 mmol of fluorescence conjugate, corresponding to an overall yield of 53% for the reaction and preparative HPLC purification.

Inhibition of Binding of Fluorescence Conjugate to TNFα

Compounds were tested at 10 concentrations starting from 25 μM in a final assay concentration of 5% DMSO, by pre-incubation with TNF for 60 minutes at ambient temperature in 20 mM Tris, 150 mM NaCl, 0.05% Tween 20, before addition of the fluorescence conjugate and a further incubation for 20 hours at ambient temperature. The final concentrations of TNFα and the fluorescence conjugate were 10 nM and 10 nM respectively in a total assay volume of 25 μL. Plates were read on a plate reader capable of detecting fluorescence polarisation (e.g. an Analyst HT plate reader; or an Envision plate reader). An $IC_{50}$ value was calculated using XLfit™ (4 parameter logistic model) in ActivityBase.

When tested in the fluorescence polarisation assay, compounds of the accompanying Examples were found to exhibit $IC_{50}$ values of 50 μM or better.

When tested in the fluorescence polarisation assay, compounds of the accompanying Examples exhibit $IC_{50}$ values generally in the range of about 0.01 nM to about 50 μM, usually in the range of about 0.01 nM to about 20 μM, typically in the range of about 0.01 nM to about 5 μM, suitably in the range of about 0.01 nM to about 1 μM, ideally in the range of about 0.01 nM to about 500 nM, appositely in the range of about 0.01 nM to about 100 nM, and preferably in the range of about 0.01 nM to about 25 nM.

Reporter Gene Assay
Inhibition of TNFα-induced NF-κB activation

Stimulation of HEK-293 cells by TNFα leads to activation of the NF-κB pathway. The reporter cell line used to determine TNFα activity was purchased from InvivoGen. HEK-Blue™ CD40L is a stable HEK-293 transfected cell line expressing SEAP (secreted embryonic alkaline phosphatase) under the control of the IFNβ minimal promoter fused to five NF-κB binding sites. Secretion of SEAP by these cells is stimulated in a dose-dependent manner by TNFα, with an EC50 of 0.5 ng/mL for human TNFα. Compounds were diluted from 10 mM DMSO stocks (final assay concentration 0.3% DMSO) to generate a 10-point 3-fold serial dilution curve (e.g. 30,000 nM to 2 nM final concentration). Diluted compound was preincubated with TNFα for 60 minutes prior to addition to a 384-well microtitre plate and incubated for 18 h. The final TNFα concentration in the assay plate was 0.5 ng/mL. SEAP activity was determined in the supernatant using a colorimetric substrate, e.g. QUANTI-Blue™ or HEK-Blue™ Detection media (InvivoGen). Percentage inhibitions for compound dilutions were calculated between a DMSO control and maximum inhibition (by excess control compound) and an $IC_{50}$ value calculated using XLfit™ (4 parameter logistic model) in ActivityBase.

When tested in the reporter gene assay, the compounds of the accompanying Examples were all found to exhibit $IC_{50}$ values of 50 μM or better.

When tested in the reporter gene assay, compounds of the accompanying Examples exhibit $IC_{50}$ values generally in the range of about 0.01 nM to about 50 μM, usually in the range of about 0.01 nM to about 20 μM, typically in the range of about 0.01 nM to about 5 μM, suitably in the range of about 0.01 nM to about 1 μM, appositely in the range of about 0.01 nM to about 500 nM, ideally in the range of about 0.01 nM to about 100 nM, and preferably in the range of about 0.01 nM to about 25 nM.

The following Examples illustrate the preparation of compounds according to the invention.

EXAMPLES

Abbreviations
 DCM: dichloromethane EtOAc: ethyl acetate
 DMF: N,N-dimethylformamide MeOH: methanol
 DMSO: dimethyl sulfoxide THF: tetrahydrofuran
 h: hour r.t.: room temperature
 M: mass RT: retention time
 HPLC: High Performance Liquid Chromatography
 LCMS: Liquid Chromatography Mass Spectrometry
 ES+: Electrospray Positive Ionisation
Analytical Conditions
 All NMR spectra were obtained either at 300 MHz or at 400 MHz.
 All reactions involving air- or moisture-sensitive reagents were performed under a nitrogen atmosphere using dried solvents and glassware.
LCMS Data Determination
Method 1 for all Analytical LCMS Performed in Basic Conditions (LCMS Basic)
 A QDA Waters simple quadrupole mass spectrometer is used for LC-MS analysis.
 This spectrometer is equipped with an ESI source and an UPLC Acquity Classic with diode array detector (210 to 400 nm).
 Data are acquired in a full MS scan from m/z 50 to 1000 in positive mode with an acidic elution.
 The reverse phase separation is carried out at 45° C. on a Waters Acquity UPLC BEH C18 1.7 μm (2.1×50 mm) column for basic elution.
Gradient Elution is Performed with:
 H$_2$O/acetonitrile/ammonium formate (95/5/63 mg/L)+50 μL NH$_4$OH (solvent A) Acetonitrile/H$_2$O/ammonium formate (95/5/63 mg/L)+50 μL NH$_4$OH (solvent B)
Gradient Program:
 HPLC flow rate: 0.6 mL/minute to 0.7 mL/minute
 Injection volume: 1 μL
 Full flow in MS.

| Time (min) | A (%) | B (%) | Flow (mL/min) |
| --- | --- | --- | --- |
| 0 | 99 | 1 | 0.4 |
| 0.3 | 99 | 1 | 0.4 |
| 3.2 | 0 | 100 | 0.4 |
| 3.25 | 0 | 100 | 0.5 |
| 4 | 0 | 100 | 0.5 |
| 4.1 | 99 | 1 | 0.4 |
| 4.8 | 90 | 1 | 0.4 |

Method 2 for all Analytical LCMS Performed in Acidic Conditions (LCMS Acidic)
 A QDA Waters simple quadrupole mass spectrometer is used for LC-MS analysis.
 This spectrometer is equipped with an ESI source and an UPLC Acquity Hclass with diode array detector (210 to 400 nm).
 Data are acquired in a full MS scan from m/z 50 to 1000 in positive mode with an acidic elution.
 The reverse phase separation is carried out at 45° C. on a Waters Acquity UPLC HSS T3 1.8 μm (2.1×50 mm) column for acidic elution.
Gradient Elution is Performed with:
 Water (solvent A)
 Acetonitrile (solvent B)
 Water/acetonitrile/formic acid 0.5% (solvent C)
Gradient Program:
 HPLC flow rate: 0.6 mL/minute to 0.7 mL/minute
 Injection volume: 1 μL
 Full flow in MS.

| Time (min) | A (%) | B (%) | C (%) | Flow (mL/min) |
| --- | --- | --- | --- | --- |
| 0 | 90 | 0 | 10 | 0.6 |
| 0.3 | 90 | 0 | 10 | 0.6 |
| 3.2 | 0 | 90 | 10 | 0.6 |
| 3.25 | 0 | 90 | 10 | 0.7 |
| 4 | 0 | 90 | 10 | 0.7 |
| 4.1 | 90 | 0 | 10 | 0.6 |
| 5.4 | 90 | 0 | 10 | 0.6 |

It will be apparent to the person skilled in the art that different retention times (RT) may be obtained for LCMS if different analytical conditions are used.
Preparative HPLC-MS
Method 1 (Acidic Preparative LCMS)
 Waters Fraction-Lynx system, with 2545 pump, 2998 PDA, 2767 fraction collector and a
 Waters 3100 MS.
 pH3_35_50 focused gradient, reverse phase.
 Waters XBridge Prep C18 OBD column, 19×100 mm, 5 μm.
 Solvent A: 10 mM ammonium bicarbonate+0.1% formic acid
 Solvent B: acetonitrile+0.1% formic acid

| Time (min) | % A | % B |
| --- | --- | --- |
| 0 | 90 | 10 |
| 2.3 | 65 | 35 |
| 11 | 50 | 50 |
| 11.5 | 5 | 95 |
| 13 | 5 | 95 |
| 13.2 | 90 | 10 |

Flow rate: 19 mL/minute (+1 mL/minute acetonitrile ACD)
Column temperature: ambient
Method 2 (Basic Preparative LCMS)
 Waters Fraction-Lynx system, with 2545 pump, 2998 PDA, 2767 fraction collector and a
 Waters 3100 MS.
 pH10_35_30 focused gradient, reverse phase.
 Waters XBridge Prep C18 OBD column, 19×100 mm, 5 μm.
 Solvent A: 10 mM ammonium bicarbonate+0.1% NH$_4$OH
 Solvent B: acetonitrile+0.1% NH$_4$OH

| Time (min) | % A | % B |
| --- | --- | --- |
| 0 | 90 | 10 |
| 2.3 | 65 | 35 |
| 11 | 50 | 50 |
| 11.5 | 5 | 95 |
| 13 | 5 | 95 |
| 13.2 | 90 | 10 |

Flow rate: 19 mL/minute (+1 mL/minute acetonitrile ACD)
Column temperature: ambient

INTERMEDIATE 1

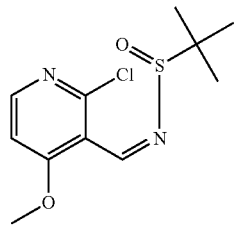

(S)-N-[(1Z)-(2-Chloro-4-methoxypyridin-3-yl)methylidene]-2-methylpropane-2-sulfinamide To a solution of 2-chloro-4-methoxypyridine-3-carbaldehyde (15 g, 87.4 mmol) in THF (180 mL) at 0° C. were added sequentially 2-methylpropane-2-sulfinamide (11.72 g, 96.7 mmol), tripotassium phosphate (56.0 g, 264 mmol) and dipotassium hydrogen phosphate (46.0 g, 264 mmol). The cooling bath was removed and the resultant suspension was stirred at r.t. for 18 h. The reaction mixture was filtered through celite, washing through with EtOAc. The filtrate was diluted with EtOAc (250 mL) and washed with brine (200 mL), then dried over anhydrous sodium sulfate, filtered and evaporated in vacuo. The crude material was purified by flash column chromatography (SiO$_2$, 0-50% EtOAc in heptane) to afford the title compound (22.0 g, 94%) as a pale yellow solid. $\delta_H$ (500 MHz, CDCl$_3$) 8.88 (s, 1H), 8.33 (d, J 5.8 Hz, 1H), 6.88 (d, J 5.8 Hz, 1H), 3.96 (s, 3H), 1.29 (s, 9H). LCMS Method 1 (ES+) RT 1.51 minutes, 275/277 (M+H)$^+$.

INTERMEDIATE 2

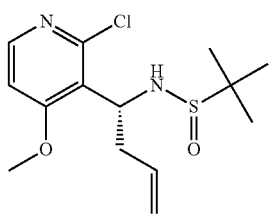

(S)-N-[(1R)-1-(2-chloro-4-methoxypyridin-3-yl)but-3-en-1-yl]-2-methylpropane-2-sulfinamide To a suspension of zinc powder (27.9 g, 369 mmol) in anhydrous THF (100 mL) was added 1,2-dibromoethane (620 µL, 7.20 mmol) and the mixture was heated to 70° C. After 10 minutes at this temperature, the reaction mixture was allowed to cool slowly to r.t. over 20 minutes. Chloro(trimethyl)silane (910 µL, 7.17 mmol) was added dropwise and the reaction mixture was heated at 50° C. for 10 minutes, before being allowed to cool to r.t. 3-Bromoprop-1-ene (18.5 mL, 214 mmol) was added dropwise at r.t. The resultant grey suspension was heated at 70° C. for 15 minutes, then cooled to −40° C. over 30 minutes. Anhydrous THF (350 mL) was added, then a pre-cooled solution of Intermediate 1 (16.9 g, 61.5 mmol) in dry THF (75 mL) was added dropwise whilst maintaining an internal reaction temperature of between −35° C. and −40° C. The resultant mixture was stirred at −40° C. for 1 h, then decanted and filtered through a sinter funnel to remove excess zinc, washing with THF (2×80 mL). The filtrate was poured into saturated aqueous ammonium chloride solution (500 mL), then extracted with EtOAc (2×500 mL). The combined organic layers were washed with brine (500 mL) and dried over anhydrous sodium sulfate, then filtered and evaporated in vacuo. The resulting crude yellow oil was purified by flash column chromatography (SiO$_2$, 0-50% EtOAc in heptane) to afford the title compound (13.4 g, 69%) as an off-white solid. $\delta_H$ (500 MHz, CDCl$_3$) 8.21 (d, J 5.7 Hz, 1H), 6.79 (d, J 5.7 Hz, 1H), 5.75-5.66 (m, 1H), 5.07 (br s, 1H), 5.04-4.96 (m, 2H), 4.19 (d, J 8.9 Hz, 1H), 3.93 (s, 3H), 2.91-2.86 (m, 1H), 2.81-2.72 (m, 1H), 1.13 (s, 9H). LCMS Method 1 (ES+) RT 1.33 minutes, 317/319 (M+H)+.

INTERMEDIATE 3

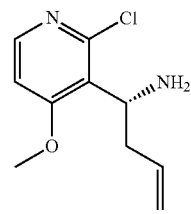

(1R)-1-(2-Chloro-4-methoxypyridin-3-yl)but-3-en-1-amine

Intermediate 2 (13.4 g, 42.3 mmol) was dissolved in diethyl ether (30 mL) and ethanol (15 mL), then 4M HCl in 1,4-dioxane (31 mL) was added. The reaction mixture was stirred for 45 minutes, then partitioned between water (200 mL) and diethyl ether (150 mL). The organic layer was re-extracted with 1M aqueous HCl solution (50 mL). The aqueous layers were combined, basified to pH 10 by addition of 6M aqueous NaOH solution and extracted with EtOAc (3×150 mL). The combined organic layers were dried over anhydrous sodium sulfate, filtered and concentrated to dryness under vacuum to yield the title compound (8.60 g, 95%) as a yellow viscous oil. $\delta_H$ (500 MHz, CDCl$_3$) 8.15 (d, J 5.7 Hz, 1H), 6.77 (d, J 5.7 Hz, 1H), 5.76 (ddt, J 17.2, 10.1, 7.2 Hz, 1H), 5.05-4.97 (m, 2H), 4.50 (t, J 7.6 Hz, 1H), 3.92 (s, 3H), 2.65-2.51 (m, 2H), 1.86 (br s, 2H). LCMS Method 1 (ES+) RT 3.17 minutes, 213/215 (M+H)$^+$.

INTERMEDIATE 4

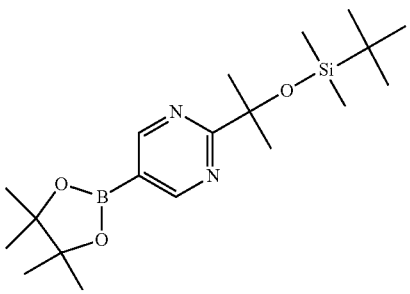

tert-Butyl(dimethyl){1-methyl-1-[5-(4,4,5,5-tetramethyl-1,3,2-dioxaborolan-2-yl)-pyrimidin-2-yl]ethoxy}silane 2-(1-Hydroxy-1-methylethyl)pyrimidine-5-boronic acid pinacol ester (10 g, 37.9 mmol), tert-butyldimethylchlorosilane (11.8 g, 75.7 mmol) and imidazole (7.9 g, 116 mmol) were dissolved in anhydrous DMF (150 mL). The reaction mixture was stirred at 85° C. for 4 days. EtOAc (100 mL) and water (250 mL) were added, then the aqueous layer was extracted with EtOAc (3×50 mL). The combined organic layers were washed with brine (3×50 mL) and dried over anhydrous magnesium sulfate, then filtered and concentrated in vacuo. The residue was purified by chromatography (SiO$_2$, 0-100% EtOAc in heptane) to afford the title compound (12.0 g, 84%) as a transparent oil. $\delta_H$ (400 MHz, CDCl$_3$) 9.04 (s, 2H), 1.70 (s, 6H), 1.40 (s, 12H), 0.94 (s, 9H), 0.01 (s, 6H).

INTERMEDIATE 5

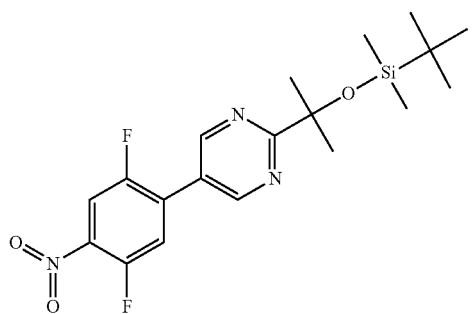

2-{2-[(tert-Butyldimethylsilyl)oxy]propan-2-yl}-5-(2,5-difluoro-4-nitrophenyl)-pyrimidine Can be synthesised from Intermediate 4 (1 eq) and 1-bromo-2,5-difluoro-4-nitro-benzene (1 eq) by a palladium-catalysed Suzuki coupling utilising [1,1'-bis(diphenylphosphino)ferrocene]dichloropalladium(II) (0.05 eq) and cesium carbonate (2 eq) in degassed 1,4-dioxane and water (10:1 mixture). The reaction is performed by heating at 100° C. under an inert atmosphere until reaction is complete by TLC. Aqueous work-up and purification by column chromatography provides the title compound.

INTERMEDIATE 6

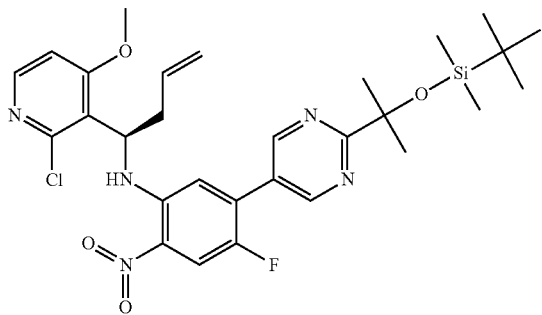

5-(2-{2-[(tert-Butyldimethylsilyl)oxy]propan-2-yl}pyrimidin-5-yl)-N-[(1R)-1-(2-chloro-4-methoxypyridin-3-yl)but-3-en-1-yl]-4-fluoro-2-nitroaniline Intermediate 3 (9.9 g, 46.6 mmol) and Intermediate 5 (21.6 g, 47.5 mmol) were dissolved in acetonitrile (200 mL) and potassium carbonate (19.3 g, 139.7 mmol) was added. The reaction mixture was stirred at 80° C. overnight, then diluted with EtOAc (500 mL) and washed with water (500 mL). The aqueous layer was extracted with EtOAc (2×250 mL), then the combined organic layers were dried over anhydrous sodium sulfate, filtered and concentrated to dryness under vacuum. The crude residue was purified by flash column chromatography (SiO$_2$, 0-30% EtOAc in heptane) to afford the title compound (23.91 g, 85%) as a red-yellow gum. $\delta_H$ (500 MHz, CDCl$_3$) 8.89-8.73 (m, 3H), 8.22 (d, J 5.7 Hz, 1H), 8.01 (d, J 10.6 Hz, 1H), 7.03 (d, J 23.2 Hz, 1H), 6.82 (d, J 5.7 Hz, 1H), 5.79 (ddt, J 17.1, 10.1, 7.1 Hz, 1H), 5.35 (q, J 8.0 Hz, 1H), 5.16 (d, J 17.0 Hz, 1H), 5.11-5.04 (m, 1H), 3.97 (s, 3H), 2.92 (d, J 6.7 Hz, 1H), 2.78 (dt, J 13.9, 7.0 Hz, 1H), 1.70 (d, J 1.3 Hz, 6H), 0.90 (s, 9H), −0.02 (d, J 1.2 Hz, 6H). LCMS Method 1 (ES+) RT 2.61 minutes, 602.1/604.1 (M+H)+.

INTERMEDIATE 7

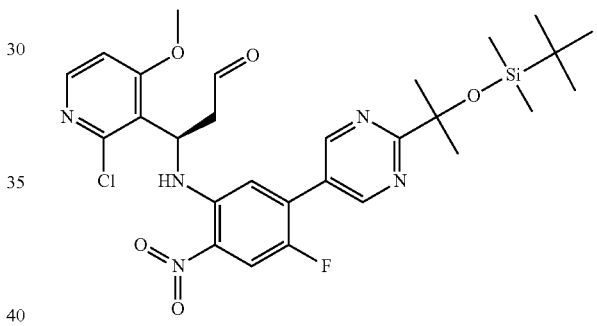

(3R)-3-{[5-(2-{2-[(tert-Butyldimethylsilyl)oxy]propan-2-yl}pyrimidin-5-yl)-4-fluoro-2-nitrophenyl]amino}-3-(2-chloro-4-methoxypyridin-3-yl)propanal To a solution of Intermediate 6 (23.9 g, 39.7 mmol) in THF (180 mL) and water (60 mL) were added sequentially N,N-dimethylpyridinyl-4-amine (9.7 g, 79.4 mmol), sodium periodate (51 g, 238 mmol) and potassium dioxido(dioxo)osmium hydrate (2:1:2) (293 mg, 0.79 mmol). The resultant mixture was stirred at r.t. overnight. Sodium thiosulfate pentahydrate (69 g, 278 mmol) was added and the mixture was stirred at r.t. for 30 minutes. DCM (200 mL) was added and the reaction mixture was stirred at r.t. for 15 minutes, then partitioned between water (500 mL) and DCM (500 mL). The layers were separated and the aqueous phase was extracted with DCM (2×250 mL). The combined organic extracts were washed with brine (500 mL) and dried over anhydrous sodium sulfate, then filtered and evaporated in vacuo. The crude residue was purified by flash column chromatography (SiO$_2$, 0-100% EtOAc in heptane, then 0-20% MeOH/DCM) to give the title compound (6.94 g, 23%). LCMS Method 2 (ES+) RT 2.32 minutes, 604.0/606.0 (M+H)$^+$.

INTERMEDIATE 8

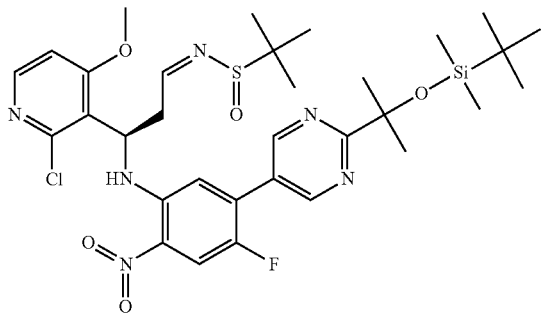

(R)-N-[(1Z,3R)-3-{[5-(2-{2-[(tert-Butyldimethylsilyl)oxy]propan-2-yl}pyrimidin-5-yl)-4-fluoro-2-nitrophenyl]amino}-3-(2-chloro-4-methoxypyridin-3-yl)propylidene]-2-methyl-propane-2-sulfinamide To a solution of Intermediate 7 (6.82 g, 10.16 mmol) and (R)-2-methylpropane-2-sulfinamide (1.24 g, 10.2 mmol) in DCM (80 mL) was added titanium(IV) isopropoxide (6.19 ml, 20.9 mmol) dropwise. The reaction mixture was stirred at 40° C. under nitrogen for 3 h, then diluted with DCM (100 mL) and quenched by the addition of brine (25 mL). The resultant sticky suspension was filtered through a celite pad, washing with further DCM (2×50 mL). The filtrate was partitioned between DCM (100 mL) and brine (100 mL). The organic layer was separated and the aqueous layer was extracted with DCM (3×100 mL). The combined organic layers were dried over anhydrous sodium sulfate, filtered and evaporated in vacuo. The resulting crude orange oil (7.3 g) was purified by chromatography on silica gel (SiO$_2$, 0-25% EtOAc/DCM) to yield the title compound (4.2 g, 54%) as a red-orange gum. $\delta_H$ (500 MHz, CDCl$_3$) 8.84 (d, J 17.8 Hz, 3H), 8.25 (d, J 5.7 Hz, 1H), 8.11 (dd, J 5.3, 3.6 Hz, 1H), 8.00 (d, J 10.5 Hz, 1H), 7.08 (d, J 34.5 Hz, 1H), 6.85 (d, J 5.7 Hz, 1H), 5.86 (td, J 9.4, 4.8 Hz, 1H), 4.01 (s, 3H), 3.57-3.47 (m, 1H), 3.11 (dt, J 16.2, 4.0 Hz, 1H), 1.71 (s, 6H), 1.12 (s, 9H), 0.90 (s, 9H), −0.01 (d, J 1.6 Hz, 6H). LCMS Method 1 (ES+) RT 2.40 minutes, 707.1/709.2 (M+H)$^+$.

INTERMEDIATE 9

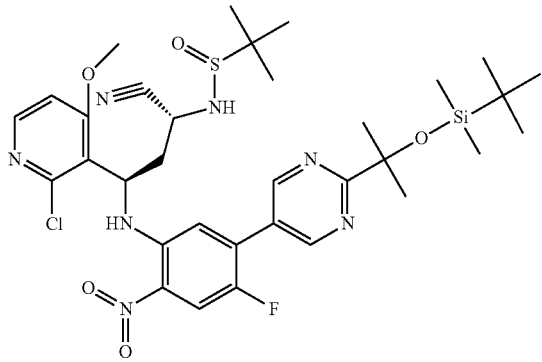

N-[(1R,3R)-3-{[5-(2-{2-[(tert-Butyldimethylsilyl)oxy]propan-2-yl}pyrimidin-5-yl)-4-fluoro-2-nitrophenyl]amino}-3-(2-chloro-4-methoxypyridin-3-yl)-1-cyanopropyl]-2-methylpropane-2-sulfinamide To Intermediate 8 (1.4 g, 1.84 mmol) in THF (25 mL) was added scandium triflate (190 mg, 0.39 mmol), followed by sodium cyanide (100 mg, 2.04 mmol). The reaction mixture was stirred under nitrogen overnight, then partitioned between EtOAc (50 mL) and saturated aqueous sodium bicarbonate solution (50 mL). The organic layer was separated, washed with brine (30 mL) and dried over anhydrous sodium sulfate, then filtered and concentrated to dryness under vacuum. The crude residue was purified by flash column chromatography (SiO$_2$, 20-100% EtOAc in heptane) to yield the title compound (680 mg, 50%) as an orange gum. $\delta_H$ (500 MHz, CDCl$_3$) 8.87 (s, 2H), 8.71 (d, J 10.3 Hz, 1H), 8.25 (d, J 5.6 Hz, 1H), 8.03 (d, J 10.4 Hz, 1H), 7.19 (s, 1H), 6.85 (d, J 5.7 Hz, 1H), 5.67 (s, 1H), 4.44 (s, 1H), 4.01 (s, 3H), 3.87 (d, J 9.4 Hz, 1H), 2.99-2.84 (m, 1H), 2.34 (s, 1H), 1.70 (s, 6H), 1.20 (s, 9H), 0.90 (s, 9H), −0.02 (d, J 2.2 Hz, 6H). LCMS Method 1 (ES+) RT 2.25 minutes, 734.1/736.2 (M+H)$^+$.

INTERMEDIATE 10

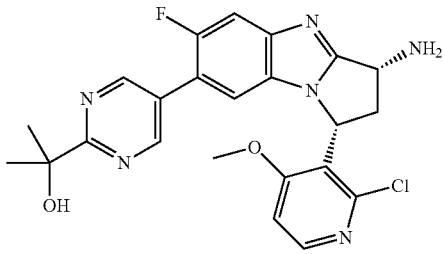

2-{5-[(1R,3R)-3-Amino-1-(2-chloro-4-methoxypyridin-3-yl)-6-fluoro-2,3-dihydro-1H-pyrrolo[1,2-a]benzimidazol-7-yl]pyrimidin-2-yl}propan-2-ol To a solution of Intermediate 9 (766 mg, 1.05 mmol) in absolute ethanol (10 mL) was added tin(II) chloride (1.03 g, 5.44 mmol), followed by concentrated HCl (605 µL). The mixture was stirred at 80° C. for 3 h, then taken up in DCM (20 mL) and water (5 mL). The pH was adjusted to 10 by the addition of 2M aqueous sodium hydroxide solution (~3 mL). The mixture was diluted with 10% aqueous potassium fluoride solution (50 mL) and stirred for 5 minutes. The resultant beige precipitate was filtered, then washed with water (5 mL) and DCM (10 mL). The phases were separated, then the aqueous phase was extracted with DCM (3×100 mL). The combined organic phases were dried over anhydrous sodium sulfate, filtered and evaporated. The crude residue was purified by flash column chromatography (SiO$_2$, 0-5% MeOH in DCM) to yield the title compound (290 mg, 68%) as a pale yellow gum. $\delta_H$ (500 MHz, CDCl$_3$) 8.73 (d, J 1.3 Hz, 2H), 8.34-8.32 (m, 1H), 7.55 (d, J 11.1 Hz, 1H), 6.75 (d, J 5.7 Hz, 1H), 6.72 (d, J 6.5 Hz, 1H), 6.18-6.03 (m, 1H), 4.74-4.70 (m, 1H), 4.61 (s, 1H), 4.06 (s, 1H), 3.63-3.55 (m, 1H), 3.52 (s, 2H), 2.58 (dt, J 13.8, 7.0 Hz, 1H), 2.00 (s, 2H), 1.63 (s, 6H). 3:1 mixture of atropisomers. LCMS Method 2 (ES$^+$) RT 0.96 minutes, 469.0, 471.0 (M+H)$^+$.

Examples 1 & 2

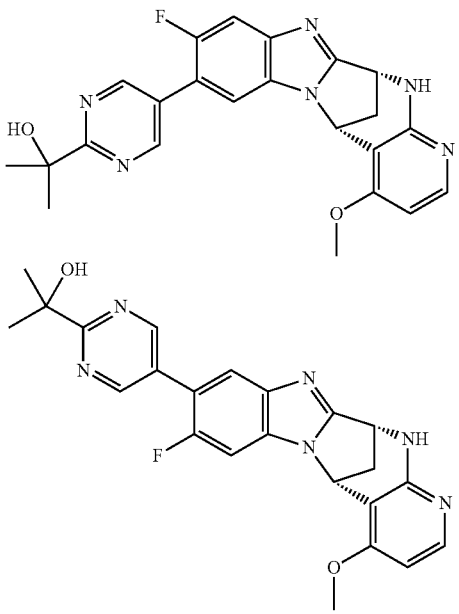

Example 1

2-{5-[(6R,12R)-3-Fluoro-11-methoxy-7,12-dihydro-6H-6,12-methanopyrido [2',3':5,6]-[1,4]diazepino [1,2-a]benzimidazol-2-yl]pyrimidin-2-yl}propan-2-ol

Example 2

2-{5-[(6R,12R)-2-Fluoro-11-methoxy-7,12-dihydro-6H-6,12-methanopyrido [2',3':5,6]-[1,4]diazepino[1,2-a]benzimidazol-3-yl]pyrimidin-2-yl}propan-2-ol A mixture of Intermediate 10 (64 mg, 0.14 mmol), potassium carbonate (47.2 mg, 0.34 mmol) and 4,5-bis(diphenylphosphino)-9,9-dimethylxanthene (7.9 mg, 0.01 mmol) in 1,4-dioxane (1 mL) was degassed by bubbling nitrogen through for 10 minutes prior to the addition of palladium(II) acetate (3.1 mg, 0.01 mmol). The reaction mixture was stirred at 100° C. in a sealed tube for 18 h, then cooled, diluted with EtOAc (10 mL) and filtered through celite. The filter cake was rinsed with EtOAc (3×5 mL), then the filtrate was partitioned between brine (25 mL) and EtOAc (25 mL). The phases were separated and the aqueous phase was extracted with EtOAc (2×25 mL). The combined organic phases were dried over anhydrous sodium sulfate, filtered and evaporated in vacuo. The residue was purified by preparative HPLC-MS.

Example 1 (5 mg, 8%) was obtained as an off-white powder. $\delta_H$ (500 MHz, CD$_3$OD) 8.99 (d, J 1.5 Hz, 2H), 7.80 (d, J 6.1 Hz, 1H), 7.67 (d, J 6.7 Hz, 1H), 7.52 (d, J 11.0 Hz, 1H), 6.44 (d, J 6.1 Hz, 1H), 6.10 (d, J 4.0 Hz, 1H), 5.03 (d, J 4.0 Hz, 1H), 4.01 (s, 3H), 3.04 (dt, J 11.3, 4.0 Hz, 1H), 2.49 (d, J 11.0 Hz, 1H), 1.68 (s, 6H). LCMS Method 4 (ES+) RT 3.48 minutes, 433 (M+H)+.

Example 2 (5 mg, 8%) was obtained as an off-white powder. $\delta_H$ (500 MHz, CD$_3$OD) 8.97 (d, J 1.6 Hz, 2H), 7.81 (d, J 6.1 Hz, 1H), 7.79 (d, J 6.7 Hz, 1H), 7.42 (d, J 10.1 Hz, 1H), 6.46 (d, J 6.1 Hz, 1H), 6.07 (d, J 4.0 Hz, 1H), 5.02 (d, J 3.5 Hz, 1H), 4.04 (s, 3H), 3.03 (dt, J 11.4, 4.0 Hz, 1H), 2.49 (d, J 11.4 Hz, 1H), 1.66 (s, 6H). LCMS Method 4 (ES+) RT 3.57 minutes, 433 (M+H)+.

Example 3

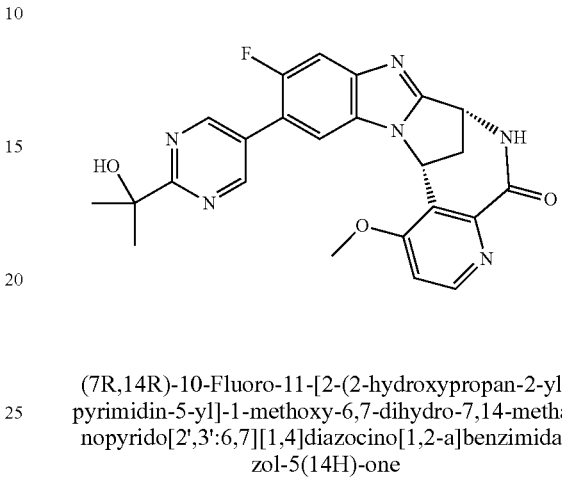

(7R,14R)-10-Fluoro-11-[2-(2-hydroxypropan-2-yl)pyrimidin-5-yl]-1-methoxy-6,7-dihydro-7,14-methanopyrido[2',3':6,7][1,4]diazocino[1,2-a]benzimidazol-5(14H)-one Intermediate 10 (50 mg, 0.107 mmol), dichloro[1,3-bis(dicyclohexylphosphino)-propane]palladium(II) (6.6 mg, 0.0107 mmol), phenol (1.00 mg, 0.0107 mmol) and potassium carbonate (22.3 mg, 0.16 mmol) were placed in a dry 5 mL vial, filled with nitrogen, before addition of 1,4-dioxane (1.1 mL) and stirred for 5 minutes at r.t. in order to obtain a homogeneous slurry. The vial was degassed and filled with CO four times. The reaction vial was placed in a high pressure reactor. The reactor was charged with 0.6 atmospheres of CO and heated at 100° C. for 18 h. The crude mixture was filtered and the solids were rinsed with EtOAc (3×5 mL), then the filtrate was evaporated. The crude residue was solubilized in DMSO and purified by preparative basic LCMS, yielding the title compound (4 mg, 8%) as an off-white solid. $\delta_H$ (400 MHz, CD$_3$OD) 8.99 (d, J 2.5 Hz, 2H), 8.56 (d, J 3.9 Hz, 1H), 7.63 (d, J 6.7 Hz, 1H), 7.54 (d, J 11.6 Hz, 1H), 7.35 (d, J 4.2 Hz, 1H), 6.57 (d, J 6.8 Hz, 1H), 5.04 (d, J 5.3 Hz, 1H), 4.24 (s, 3H), 3.56 (dq, J 13.9, 6.8, 6.1 Hz, 1H), 2.80 (d, J 13.5, 1H), 1.65 (s, 6H). LCMS Method 1 (ES+) RT 3.00 minutes, 461 (M+H)+. LCMS Method 2 (ES+) RT 2.73 minutes, 461 (M+H)+.

The invention claimed is:

1. A compound of formula (I) or an N-oxide thereof, or a pharmaceutically acceptable salt thereof:

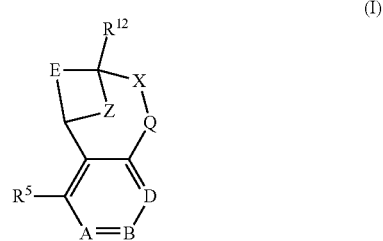

wherein
A represents C—R⁶;
B represents C—R⁷; and
D represents N;
—X-Q- represents —O—, —O—C(O)—, —O—C(=CH—CN)—, —S—, —SO—, —SO₂—, —N(Rᵍ)—, —N(Rᶠ)—CON(Rᶠ)—SO₂—, N(Rᶠ)—C(S)—, —N=S(O)(CH₃)—, —O—C(=CH₂)— or —S(=N—CN)—; or —X-Q- represents O—CH₂—, —CH₂—S—, —CH₂—SO—, —CH₂—SO₂—, —N(Rᵍ)—CH₂—, any of which groups may be optionally substituted by one or more substituents selected from halogen, C₁₋₆ alkyl, hydroxy(C₁₋₆) alkyl, trifluoromethyl, C₂₋₆ alkylcarbonyl, carboxy and C₂₋₆ alkoxycarbonyl
Z represents methylene;
E represents a fused heteroaromatic ring system of formula (Ea):

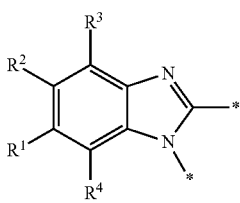

(Ea)

wherein the asterisks (*) represent the site of attachment of E to the remainder of the molecule;
R¹ represents hydrogen or halogen or —C₃₋₇ heterocycloalkyl, heteroaryl, (C₃₋₇)cycloalkyl-heteroaryl-, (C₃₋₇)heterocycloalkyl-heteroaryl-, or (C₄₋₉)heterobicycloalkyl-heteroaryl, any of which groups may be optionally substituted by one or more substituents selected from halogen, cyano, C₁₋₆ alkyl, difluoromethyl, hydroxy(C₁₋₆)alkyl, oxo, amino and amino(C₁₋₆)alkyl;
R² represents halogen, or R² represents heteroaryl, either of which groups may be optionally substituted by one or more substituents selected from hydroxy(C₁₋₆)alkyl and C₂₋₆ alkoxycarbonyl;
R³ and R⁴ independently represent hydrogen, halogen or or C₁₋₆ alkyl,
R⁵ represents difluoro-methoxy, or —ORᵃ ;
R⁶ represents hydrogen, halogen or trifluoromethyl;
R⁷ represents hydrogen or trifluoromethyl;
R⁸ represents hydrogen or trifluoromethyl;
R¹² represents hydrogen or C₁₋₆ alkyl;
Rᵃ represents C₁₋₆ alkyl, aryl(C₁₋₆)alkyl, or heteroaryl(C₁₋₆)alkyl, any of which groups may be optionally substituted by one or more substituents selected from C₁₋₆ alkoxy and oxo;
Rᶠ represents hydrogen or C₁₋₆ alkyl;
Rᵍ represents hydrogen, —SO₂Rᵃ, —CORᵈ or —CO₂Rᵈ; or Rᵍ represents C₁₋₆ alkyl, or heteroaryl, any of which groups may be optionally substituted by one or more substituents selected from halogen, trifluoromethyl, C₁₋₆ alkyl, C₄₋₉ heterobicycloalkyl, hydroxy, C₁₋₆ alkoxy, C₁₋₆ alkylsulphonyl, carboxy and C₂₋₆ alkoxycarbonyl; and
Rᵈ represents hydrogen; or Rᵈ represents C₁₋₆ alkyl, C₃₋₇ cycloalkyl, aryl, C₃₋₇ heterocycloalkyl or heteroaryl, any of which groups may be optionally substituted by one or more substituents selected from halogen, C₁₋₆ alkyl, C₁₋₆ alkoxy, oxo, C₂₋₆ alkylcarbonyl and di(C₁₋₆)alkylamino.

2. The compound as claimed in claim 1 represented by formula (IIA) or an N-oxide thereof, or a pharmaceutically acceptable salt thereof:

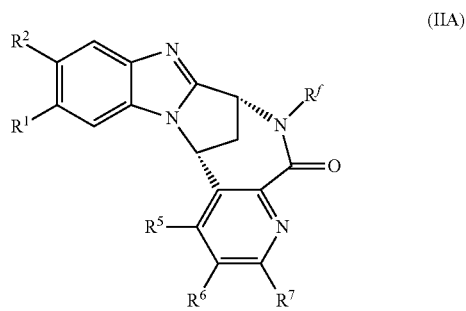

(IIA)

wherein R¹, R², R⁵, R⁶, R⁷ and Rᶠ are as defined in claim 1.

3. The compound as claimed in claim 1 represented by formula (IIB) or an N-oxide thereof, or a pharmaceutically acceptable salt thereof:

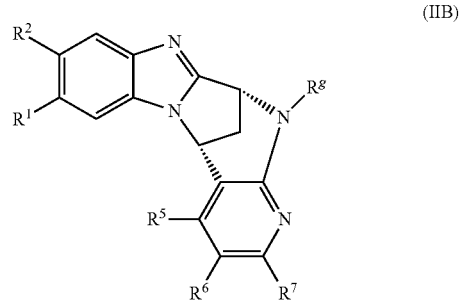

(IIB)

wherein R¹, R², R⁵, R⁶, R⁷ and Rᵍ are as defined in claim 1.

4. The compound as claimed in claim 1 which is selected from the group consisting of
2-{5-[(6R,12R)-3-Fluoro-11-methoxy-7,12-dihydro-6H-6,12-methanopyrido[2',3':5,6]-[1,4]diazepino[1,2-a]benzimidazol-2-yl]pyrimidin-2-yl}propan-2-ol;
2-{5-[(6R,12R)-2-Fluoro-11-methoxy-7,12-dihydro-6H-6,12-methanopyrido[2',3':5,6]-[1,4]diazepino[1,2-a]benzimidazol-3-yl]pyrimidin-2-yl}propan-2-ol; and
(7R,14R)-10-Fluoro-11-[2-(2-hydroxypropan-2-yl)pyrimidin-5-yl]-1-methoxy-6,7-dihydro-7,14-methanopyrido[2',3':6,7][1,4]diazocino[1,2-a]benzimidazol-5(14H)-one.

5. A pharmaceutical composition comprising a compound of formula (I) as defined in claim 1 or an N-oxide thereof, or a pharmaceutically acceptable salt thereof, in association with a pharmaceutically acceptable carrier.

6. The pharmaceutical composition as claimed in claim 5 further comprising an additional pharmaceutically active ingredient.

7. The compound as claimed in claim 1 wherein R¹ represents heteroaryl, which group may be optionally substituted by one or more substituents selected from halogen, cyano, C₁₋₆ alkyl, difluoromethyl, hydroxy(C₁₋₆)alkyl, oxo, amino and amino(C₁₋₆) alkyl.

8. The compound as claimed in claim 1 wherein -X-Q- represents —N($R^g$)— or —N($R^f$)—CO—.

9. The compound as claimed in claim 1 wherein $R^2$ represents halogen.

10. The compound as claimed in claim 1 wherein $R^g$ represents hydrogen or methyl.

* * * * *

UNITED STATES PATENT AND TRADEMARK OFFICE
CERTIFICATE OF CORRECTION

PATENT NO.         : 10,669,286 B2
APPLICATION NO.    : 16/086418
DATED              : June 2, 2020
INVENTOR(S)        : Michael Louis Robert Deligny Page 1 of 1

It is certified that error appears in the above-identified patent and that said Letters Patent is hereby corrected as shown below:

In the Claims

Claim 1, Column 57, Line 7, delete "-N($R^f$)-CON($R^f$)-SO2-" and insert -- -N($R^f$)-CO-, -N($R^f$)-SO$_2$- --

Signed and Sealed this
First Day of September, 2020

Andrei Iancu
*Director of the United States Patent and Trademark Office*